(12) United States Patent
Tanaka et al.

(10) Patent No.: US 10,219,916 B2
(45) Date of Patent: Mar. 5, 2019

(54) METHOD FOR FUSING SPINAL VERTEBRAE

(71) Applicant: SPINE WAVE, INC., Shelton, CT (US)

(72) Inventors: Shigeru Tanaka, Half Moon Bay, CA (US); Edward Liou, Pleasanton, CA (US)

(73) Assignee: SPINE WAVE, INC., Shelton, CT (US)

( * ) Notice: Subject to any disclaimer, the term of this patent is extended or adjusted under 35 U.S.C. 154(b) by 0 days.

(21) Appl. No.: 15/975,267

(22) Filed: May 9, 2018

(65) Prior Publication Data

US 2018/0256354 A1   Sep. 13, 2018

Related U.S. Application Data

(62) Division of application No. 14/599,250, filed on Jan. 16, 2015, now Pat. No. 9,968,464.

(Continued)

(51) Int. Cl.
*A61F 2/44* (2006.01)
*A61F 2/30* (2006.01)
(Continued)

(52) U.S. Cl.
CPC ............ *A61F 2/447* (2013.01); *A61F 2/4455* (2013.01); *A61F 2/4611* (2013.01); *A61F 2/4657* (2013.01); *A61F 2/4684* (2013.01); *A61B 17/86* (2013.01); *A61F 2/30749* (2013.01); *A61F 2002/30507* (2013.01); *A61F 2002/30578* (2013.01); *A61F 2002/30579* (2013.01); *A61F 2002/4623* (2013.01); *A61F 2002/4627* (2013.01)

(58) Field of Classification Search
CPC .................... A61F 2/4684; A61F 2002/30578
See application file for complete search history.

(56) References Cited

U.S. PATENT DOCUMENTS 2,998,007 A   8/1961   Herzog
3,574,381 A   4/1971   Ocheltree et al.
(Continued)

FOREIGN PATENT DOCUMENTS

EP   0 064 724 A2   11/1982
FR   2827156 A1   1/2003

*Primary Examiner* — Nicholas Woodall
(74) *Attorney, Agent, or Firm* — Hoffmann & Baron, LLP

(57) ABSTRACT

A spinal fusion system may include an interbody fusion cage, a fixation plate, and an implanter. The interbody fusion cage may include a proximal region, a distal region opposite the proximal region, a superior region, an inferior region opposite the superior region, and an open volume between the proximal and distal regions. The superior and inferior regions are located between the proximal and distal regions and are configured such that, when the interbody fusion cage is implanted in the disc space, the superior region contracts the inferior end plate and the inferior region contacts the superior end plate. The fixation plate is receivable in the open volume of the interbody fusion cage and includes a superior blade and an inferior blade. At least one of the blades includes a first opening defined therein. The fixation plate is displaceable between a non-deployed state and a deployed state.

8 Claims, 48 Drawing Sheets

Related U.S. Application Data

(60) Provisional application No. 61/969,695, filed on Mar. 24, 2014, provisional application No. 61/949,015, filed on Mar. 6, 2014, provisional application No. 61/928,799, filed on Jan. 17, 2014.

(51) Int. Cl.
*A61F 2/46* (2006.01)
*A61B 17/86* (2006.01)

(56) References Cited

U.S. PATENT DOCUMENTS

| | | |
|---|---|---|
| 3,814,089 A | 6/1974 | Deyerle |
| 4,275,717 A | 6/1981 | Bolesky |
| 4,519,100 A | 5/1985 | Wills et al. |
| 4,667,664 A | 5/1987 | Taylor et al. |
| 4,848,327 A | 7/1989 | Perdue |
| 4,892,545 A | 1/1990 | Day et al. |
| 5,057,103 A | 10/1991 | Davis |
| 5,397,364 A | 3/1995 | Kozak et al. |
| 5,522,899 A | 6/1996 | Michelson |
| 5,534,004 A | 7/1996 | Santangelo |
| 5,601,550 A | 2/1997 | Esser |
| 5,782,830 A | 7/1998 | Farris |
| 5,800,550 A | 9/1998 | Sertich |
| 5,810,820 A | 9/1998 | Santori et al. |
| 5,971,986 A | 10/1999 | Santori et al. |
| 5,976,139 A | 11/1999 | Bramlet |
| 6,030,401 A | 2/2000 | Marino |
| 6,077,264 A | 6/2000 | Chemello |
| 6,099,531 A | 8/2000 | Bonutti |
| 6,120,503 A | 9/2000 | Michelson |
| 6,174,311 B1 | 1/2001 | Branch et al. |
| 6,179,873 B1 | 1/2001 | Zientek |
| 6,183,474 B1 | 2/2001 | Bramlet et al. |
| 6,235,059 B1 | 5/2001 | Benezech et al. |
| 6,342,057 B1 | 1/2002 | Brace et al. |
| 6,342,074 B1 | 1/2002 | Simpson |
| 6,379,364 B1 | 4/2002 | Brace et al. |
| 6,409,768 B1 | 6/2002 | Tepic et al. |
| 6,443,954 B1 | 9/2002 | Bramlet et al. |
| 6,447,546 B1 | 9/2002 | Bramlet et al. |
| 6,468,311 B2 | 10/2002 | Boyd et al. |
| 6,527,803 B1 | 3/2003 | Crozet et al. |
| 6,558,388 B1 | 5/2003 | Bartsch et al. |
| 6,558,423 B1 | 5/2003 | Michelson |
| 6,648,889 B2 | 11/2003 | Bramlet et al. |
| 6,770,096 B2 | 8/2004 | Bolger et al. |
| 7,056,344 B2 | 6/2006 | Huppert et al. |
| 7,223,289 B2 * | 5/2007 | Trieu ............... A61B 17/70 606/151 |
| 7,232,464 B2 | 6/2007 | Mathieu et al. |
| 7,235,082 B2 | 6/2007 | Bartish et al. |
| 7,416,553 B2 | 8/2008 | Patel et al. |
| 7,594,931 B2 | 9/2009 | Louis et al. |
| 7,674,287 B2 | 3/2010 | Alferness et al. |
| 7,695,516 B2 | 4/2010 | Zeegers |
| 7,776,047 B2 | 8/2010 | Fanger et al. |
| 7,842,088 B2 | 11/2010 | Rashbaum et al. |
| 7,846,207 B2 | 12/2010 | Lechmann et al. |
| 7,909,829 B2 | 3/2011 | Patel et al. |
| 7,909,848 B2 | 3/2011 | Patel et al. |
| 7,935,123 B2 | 5/2011 | Fanger et al. |
| 7,988,693 B2 | 8/2011 | Martz et al. |
| 8,002,776 B2 | 8/2011 | Liu et al. |
| 8,062,303 B2 | 11/2011 | Berry et al. |
| 8,080,062 B2 | 12/2011 | Armstrong et al. |
| 8,147,556 B2 | 4/2012 | Louis et al. |
| 8,257,439 B2 | 9/2012 | Zeegers |
| 8,267,997 B2 | 9/2012 | Colleran |
| 8,268,000 B2 | 9/2012 | Waugh et al. |
| 8,273,127 B2 | 9/2012 | Jones et al. |
| 8,282,682 B2 | 10/2012 | Kirschman |
| 8,292,958 B1 * | 10/2012 | Bruffey ............ A61F 2/442 606/246 |
| 8,313,528 B1 | 11/2012 | Wensel |
| 8,328,870 B2 | 12/2012 | Patel et al. |
| 8,328,872 B2 | 12/2012 | Duffield et al. |
| 8,343,219 B2 | 1/2013 | Allain et al. |
| 8,377,133 B2 | 2/2013 | Yuan et al. |
| 8,394,107 B2 | 3/2013 | Fanger et al. |
| 8,409,285 B2 | 4/2013 | Keller |
| 8,454,700 B2 | 6/2013 | Lemoine et al. |
| 8,460,388 B2 | 6/2013 | Kirwan et al. |
| 8,523,946 B1 | 9/2013 | Swann |
| 8,617,245 B2 | 12/2013 | Brett |
| 8,641,766 B2 | 2/2014 | Donner et al. |
| 8,685,104 B2 | 4/2014 | Lee et al. |
| 8,709,083 B2 | 4/2014 | Duffield et al. |
| 8,728,165 B2 | 5/2014 | Parry et al. |
| 8,840,651 B2 | 9/2014 | Reiley |
| 8,864,830 B2 | 10/2014 | Malandain |
| 8,906,101 B2 | 12/2014 | Lee et al. |
| 8,932,359 B2 | 1/2015 | Brett |
| 8,968,405 B2 | 3/2015 | Kirwan et al. |
| 9,033,993 B2 | 5/2015 | Bae et al. |
| 9,039,774 B2 | 5/2015 | Chataigner et al. |
| 9,044,337 B2 | 6/2015 | Dinville et al. |
| 9,078,765 B2 | 7/2015 | Louis et al. |
| 9,101,489 B2 | 8/2015 | Protopsaltis et al. |
| 9,155,631 B2 | 10/2015 | Seifert et al. |
| 9,161,841 B2 | 10/2015 | Kana et al. |
| 9,241,809 B2 | 1/2016 | McDonough et al. |
| 9,358,134 B2 | 6/2016 | Malandain |
| 9,402,740 B1 | 8/2016 | Donaldson |
| 9,402,741 B1 | 8/2016 | Donaldson |
| 9,572,685 B2 | 2/2017 | Perry |
| 2004/0082955 A1 | 4/2004 | Zirkle, Jr. |
| 2007/0239168 A1 | 10/2007 | Kuenzi et al. |
| 2007/0250167 A1 | 10/2007 | Bray et al. |
| 2008/0249569 A1 | 10/2008 | Waugh et al. |
| 2008/0281425 A1 | 11/2008 | Thalgott et al. |
| 2009/0099601 A1 * | 4/2009 | Aferzon ............ A61F 2/4455 606/246 |
| 2009/0164020 A1 | 6/2009 | Janowski et al. |
| 2010/0016968 A1 | 1/2010 | Moore |
| 2010/0145459 A1 | 6/2010 | McDonough et al. |
| 2010/0185289 A1 | 7/2010 | Kirwan et al. |
| 2011/0098747 A1 | 4/2011 | Donner et al. |
| 2011/0208311 A1 | 8/2011 | Janowski |
| 2012/0078373 A1 | 3/2012 | Gamache et al. |
| 2012/0116466 A1 | 5/2012 | Dinville et al. |
| 2012/0191196 A1 | 7/2012 | Louis et al. |
| 2012/0197401 A1 | 8/2012 | Duncan et al. |
| 2012/0253406 A1 | 10/2012 | Bae et al. |
| 2012/0277872 A1 | 11/2012 | Kana et al. |
| 2012/0277873 A1 | 11/2012 | Kana et al. |
| 2013/0110242 A1 * | 5/2013 | Kirwan ............ A61F 2/4455 623/17.16 |
| 2013/0150968 A1 | 6/2013 | Dinville et al. |
| 2013/0226300 A1 * | 8/2013 | Chataigner ........ A61F 2/442 623/17.16 |
| 2014/0088711 A1 | 3/2014 | Chin |
| 2014/0114413 A1 | 4/2014 | Allain et al. |
| 2014/0142619 A1 | 5/2014 | Serina et al. |
| 2014/0156010 A1 | 6/2014 | Lee et al. |
| 2014/0163684 A1 | 6/2014 | Donner et al. |
| 2014/0277456 A1 | 9/2014 | Kirschman |
| 2015/0051702 A1 | 2/2015 | Chataigner et al. |
| 2015/0051704 A1 | 2/2015 | Duffield et al. |
| 2015/0057754 A1 | 2/2015 | Reed et al. |
| 2015/0127107 A1 | 5/2015 | Kim et al. |
| 2015/0127109 A1 | 5/2015 | Brett |
| 2015/0202051 A1 | 7/2015 | Tanaka et al. |
| 2015/0209089 A1 | 7/2015 | Chataigner et al. |
| 2015/0305883 A1 | 10/2015 | Garber et al. |
| 2015/0305887 A1 | 10/2015 | McAtamney et al. |
| 2016/0015523 A1 | 1/2016 | Lewis et al. |
| 2016/0151166 A1 | 6/2016 | Morris et al. |

\* cited by examiner

METHOD FOR FUSING SPINAL VERTEBRAE

CROSS-REFERENCE TO RELATED APPLICATIONS

This application is a divisional application of U.S. patent application Ser. No. 14/599,250, entitled "SPINAL FUSION SYSTEM," filed Jan. 16, 2015, now U.S. Pat. No. 9,968,464, which claims the benefit of U.S. Provisional Patent Application Ser. Nos. 61/928,799, entitled "STAND-ALONE CAGE SYSTEM: INTEGRATED ANCHOR/SCREW DESIGN," filed on Jan. 17, 2014; 61/949,015, entitled "SYSTEM AND METHOD OF IMPLANTING A SPINAL IMPLANT," filed on Mar. 6, 2014; and 61/969,695 entitled "SPINAL FUSION SYSTEM," filed Mar. 24, 2014. The full disclosures of the above-listed patent applications are hereby incorporated by reference herein.

FIELD

Aspects of the present disclosure related to systems and methods for the treatment of spinal conditions. More specifically, the present disclosure relates to spinal implants and delivery systems for, and methods of, delivering and implanting spinal implants in a spinal column in the treatment of a spinal condition, including spinal fusion treatments.

BACKGROUND

Spinal fusions are commonly performed on patients suffering from pain and dysfunction stemming from spinal trauma, degenerative diseases, birth defects, etc. Spinal fusions can be time intensive to perform, and surgical outcomes for patients are not always as desired or hoped for.

There exists a need in the art for improved spinal fusion systems and methods.

BRIEF SUMMARY

Disclosed herein is a spinal fusion system and method for fusing together a superior vertebra and an inferior vertebra. The superior vertebra includes an inferior endplate and a vertebral body, and the inferior vertebra includes a superior endplate and a vertebral body. The superior and inferior endplates define a disc space.

In one embodiment, the spinal fusion system includes an interbody fusion cage, a fixation plate, and an implanter. The interbody fusion cage includes a proximal region, a distal region opposite the proximal region, a superior region, an inferior region opposite the superior region, and an open volume between the proximal and distal regions. The superior and inferior regions are located between the proximal and distal regions and are configured such that, when the interbody fusion cage is implanted in the disc space, the superior region contacts the inferior end plate, and the inferior region contacts the superior end plate. The fixation plate is receivable in the open volume of the interbody fusion cage and includes a superior blade and an inferior blade. At least one of the blades includes a first opening defined therein. The fixation plate is displaceable between a non-deployed state and a deployed state, wherein, when the fixation plate is received in the open volume and the fixation plate is in the non-deployed state, the superior and inferior blades extend generally parallel to each other. And, when the fixation plate is received in the open volume and the fixation plate is in the deployed state, the superior and inferior blades extend oppositely from each other.

The implanter includes a distal end configured for releasable coupling with the proximal region of the interbody fusion cage. The implanter further includes a first guide system configured to guide a first delivery trajectory of a first bone screw. The first delivery trajectory includes a first axis that extends along the first guide system and through the first opening when the distal end is coupled to the proximal end and the blades are in the deployed state.

In one embodiment, the superior and inferior blades in a deployed state may extend generally perpendicular to a direction the blades extended when in a non-deployed state. In another embodiment, the superior and inferior blades may extend generally parallel to each other, pointing proximally and being substantially within the open volume.

In another embodiment, the superior blade includes the first opening, and the inferior blade includes a second opening. Further, the implanter includes a second guide system that is configured to guide a second delivery trajectory of a second bone screw. The second delivery trajectory includes a second axis that extends along the second guide system and through the second opening when the distal end is coupled to the proximal end and the blades are in the deployed state.

In another embodiment, the first guide system includes a distal component and a proximal component proximally offset from the distal component. Each component acts to at least partially confine the first axis of the first delivery trajectory to pass through the first opening when the distal end is coupled to the proximal end and the blades are in the deployed state. The embodiment may also include where the distal component restricts the first delivery trajectory in four directions along two axes perpendicular to the first axis. This embodiment may additionally include where the proximal component restricts the first delivery trajectory in three directions along two axes perpendicular to the first axis.

Moreover, this embodiment may also include where the distal component includes a fully enclosed opening in a structure near the distal end, and the implanter further includes a proximal handle comprising a groove extending longitudinally along the handle, the groove comprising the proximal component.

In another embodiment, the system further includes a screw driver. The screw driver includes a distal end adapted to mechanically engage a distal end of the first screw. Additionally, the screw driver is further adapted to interact with the first guide system in delivering the first screw through the first opening along the first trajectory.

In another embodiment, the fixation plate includes a drive mechanism that drives the fixation plate from the non-deployed state to the deployed state. Additionally, the implanter further includes a drive component that interacts with the drive mechanism to cause the drive mechanism to drive the fixation plate. In this version, the drive mechanism may include a drive nut threadably supported on a threaded drive shaft, the drive nut being coupled to the fixation plate. And, the drive component may include a member rotatable to the implanter and including a distal end that engages the threaded drive shaft to transmit rotation of the member to the threaded drive shaft. This version may also include where the drive nut proximally displacing along the threaded drive shaft causes the fixation plate to transition from the non-deployed state to the deployed state.

In another embodiment, the implanter includes a ramp distally projecting from the distal end of the implanter. The blades abut against sloped surfaces of the ramp, where the abutting causing the blades to divert from the non-deployed state to the deployed state.

In another embodiment, the distal end includes distally projecting members that are received in the proximal region of the interbody fusion cage to couple the cage to the distal end in a releasable manner. In this embodiment, the projecting members may include at least one of smooth pins for an interference fit, threaded pins for a threaded engagement, or hook-latches for a hooked engagement.

In another embodiment, the proximal region of the interbody fusion cage includes an open configuration through which the fixation plate can be delivered.

In another embodiment, the interbody fusion cage and the fixation plate are configured to interact with each other when the fixation plate is located in the open volume and in the deployed state such that the fixation plate and interbody fusion cage become locked together to prevent anterior-posterior and lateral displacement relative to each other. In this version, the interbody fusion cage may include a slot or notch that receives a portion of one of the blades when the fixation plate is located in the open volume and in the deployed state.

Also disclosed herein is a method of fusing a superior vertebra to an inferior vertebra. In one embodiment, the method includes inserting an interbody fusion cage into a disc space defined by an inferior endplate of the superior vertebra and a superior endplate of the inferior vertebra (step a). The method further includes causing an inferior blade of a fixation plate located in an open volume of the interbody fusion cage to penetrate the superior endplate and extend at least half a vertical distance of a vertebral body of the inferior vertebrae into the vertebral body of the interior vertebrae (step b). The method further includes causing a superior blade of the fixation plate to penetrate the inferior endplate and extend at least half a vertical distance of a vertebral body of the superior vertebra into the vertebral body of the superior vertebra (step c). The method also includes causing a first bone screw to penetrate an anterior face of the vertebral body of the inferior vertebra and extend into the vertebral body of the inferior vertebra to be received in an opening defined in the inferior blade embedded in the vertebral body of the inferior vertebra (step d). The method also includes causing a second bone screw to penetrate an anterior face of the vertebral body of the superior vertebra and extend into the vertebral body to the superior vertebra to be received in an opening defined in the superior blade embedded in the vertebral body of the superior vertebra (step ce).

In one embodiment, steps d) and ce) are brought about via a blind delivery of the bone screws via an implanter coupled to a proximal region of the interbody fusion cage. In this version, the implanter may include inferior and superior trajectory guides that respectively have inferior and superior axes that respectively extend through the opening defined in the inferior blade and the opening in the superior blade when the blades are embedded in the respective vertebral bodies.

While multiple embodiments are disclosed herein, the various embodiments as described in the disclosure are capable of modifications in various aspects, all without departing from the spirit and scope of the present disclosure. Accordingly, the drawings and detailed description are to be regarded as illustrative in nature and not restrictive.

These and other aspects and embodiments, will be described in further detail below, in reference to the attached drawing figures.

BRIEF DESCRIPTION OF DRAWINGS

Corresponding reference characters and labels indicate corresponding elements among the views of the drawings. The headings used in the figures should not be interpreted to limit the scope of the claims.

DETAILED DESCRIPTION

Figure 1:
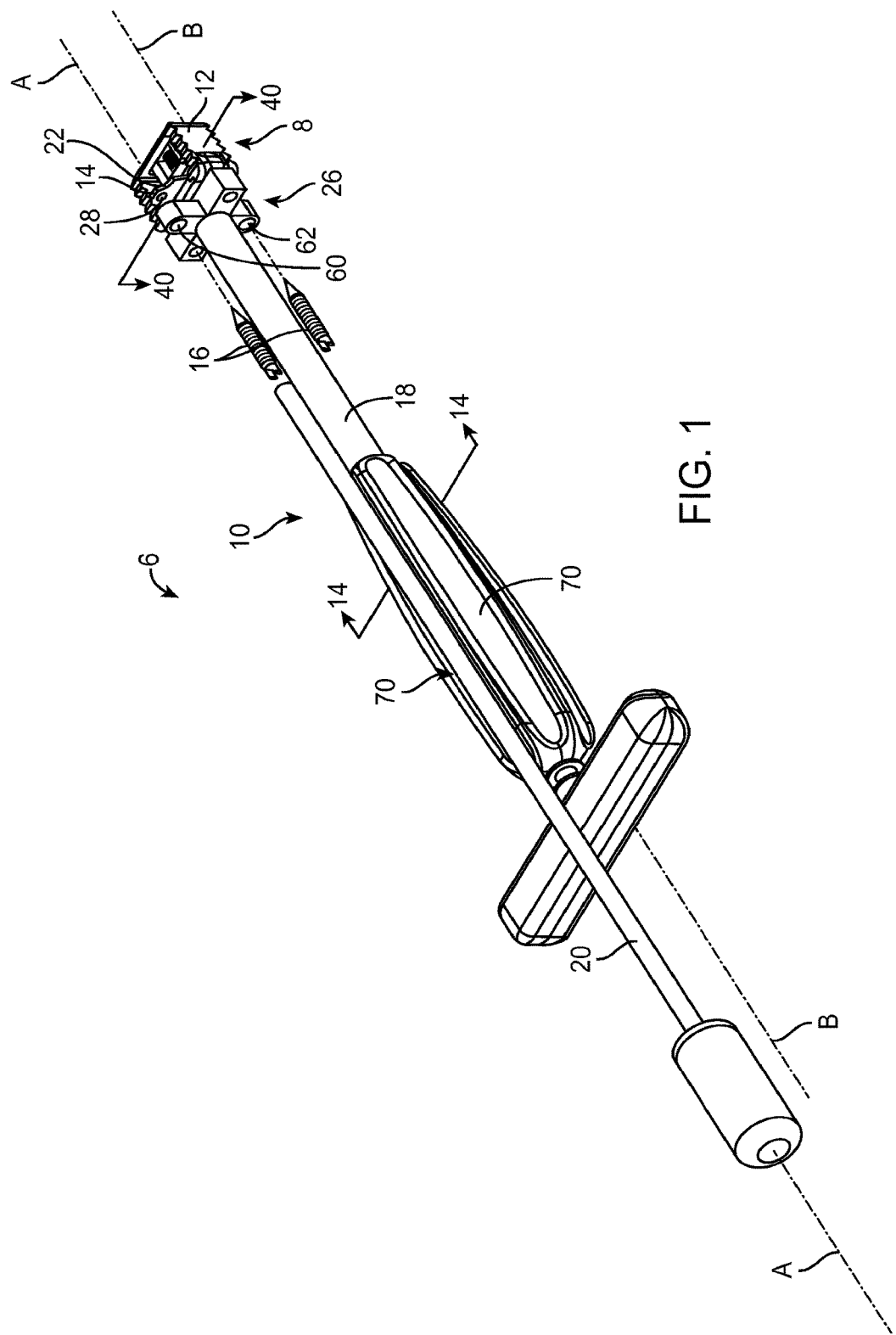
FIG. 1 is a proximal isometric view of a spinal fusion system with the spinal implant supported on a distal end of the implanter, the anterior fixation plate deployed, and the screw driver interfaced with the implanter, so as to be properly aligned to guide the first of two bone screws through corresponding receiving openings of the plate, according to one embodiment.
Figure 2:
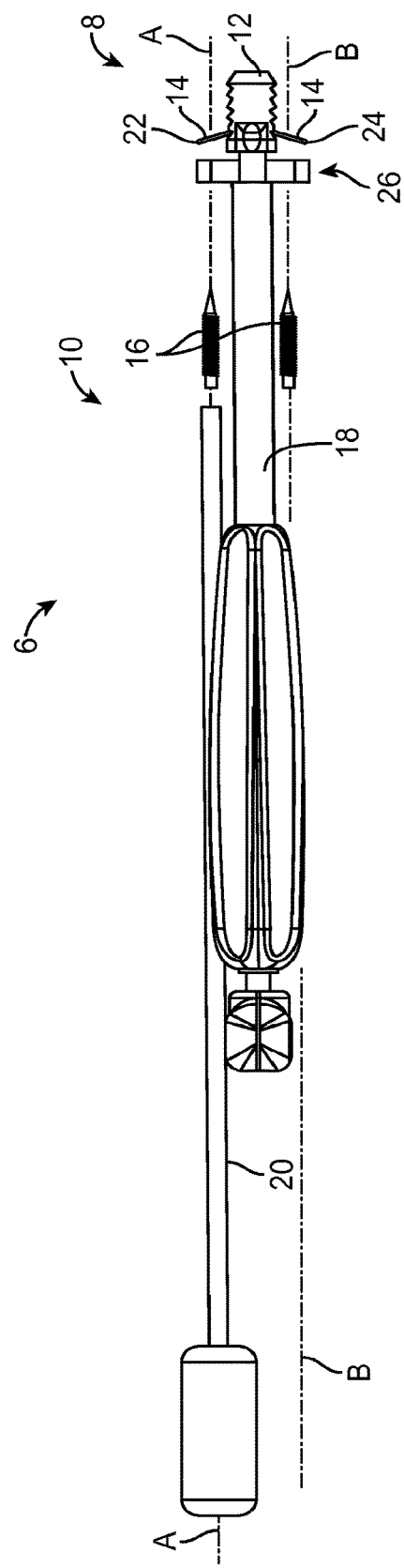
FIG. 2 is a longitudinal side elevation of the spinal fusion system and relationships depicted in FIG. 1.
Figure 3:
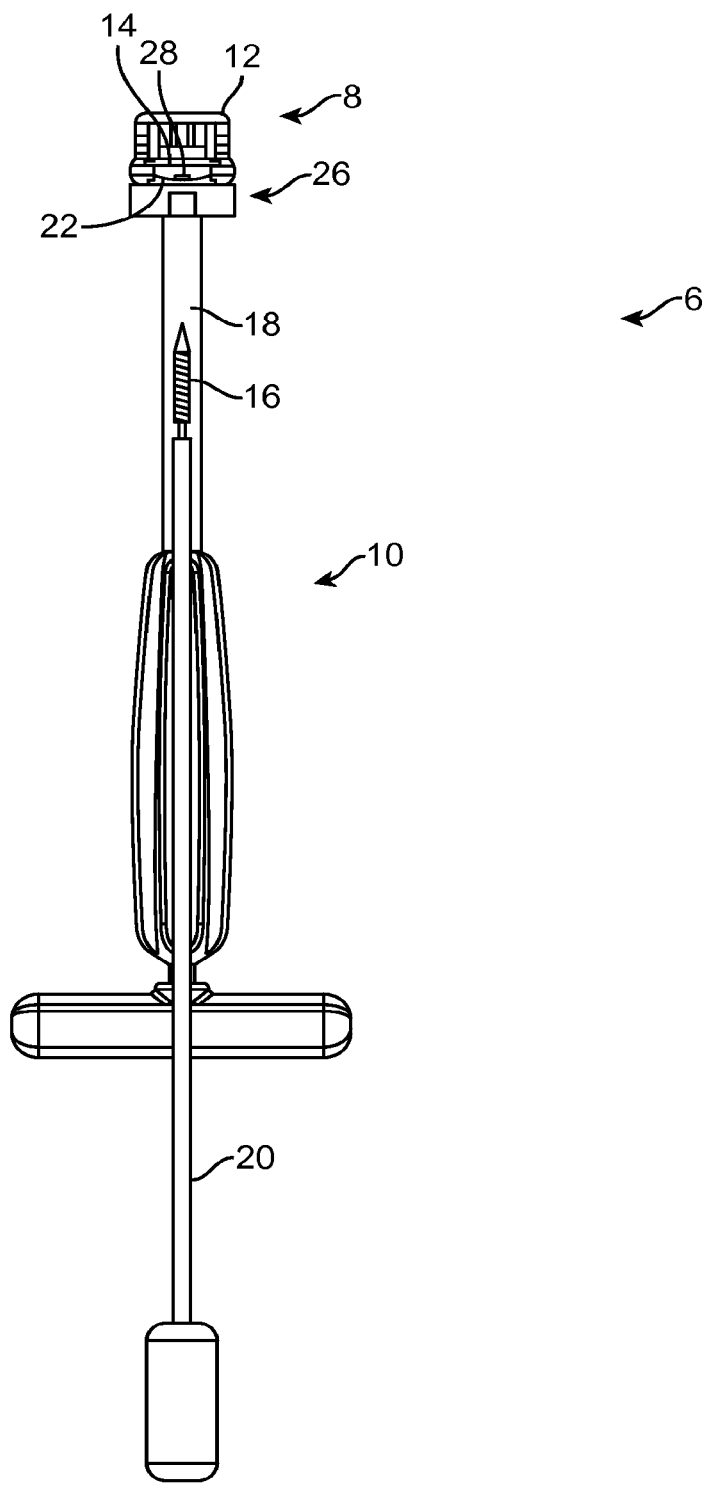
FIG. 3 is a longitudinal top plan view of the spinal fusion system and relationships depicted in FIG. 1.
Figure 4:
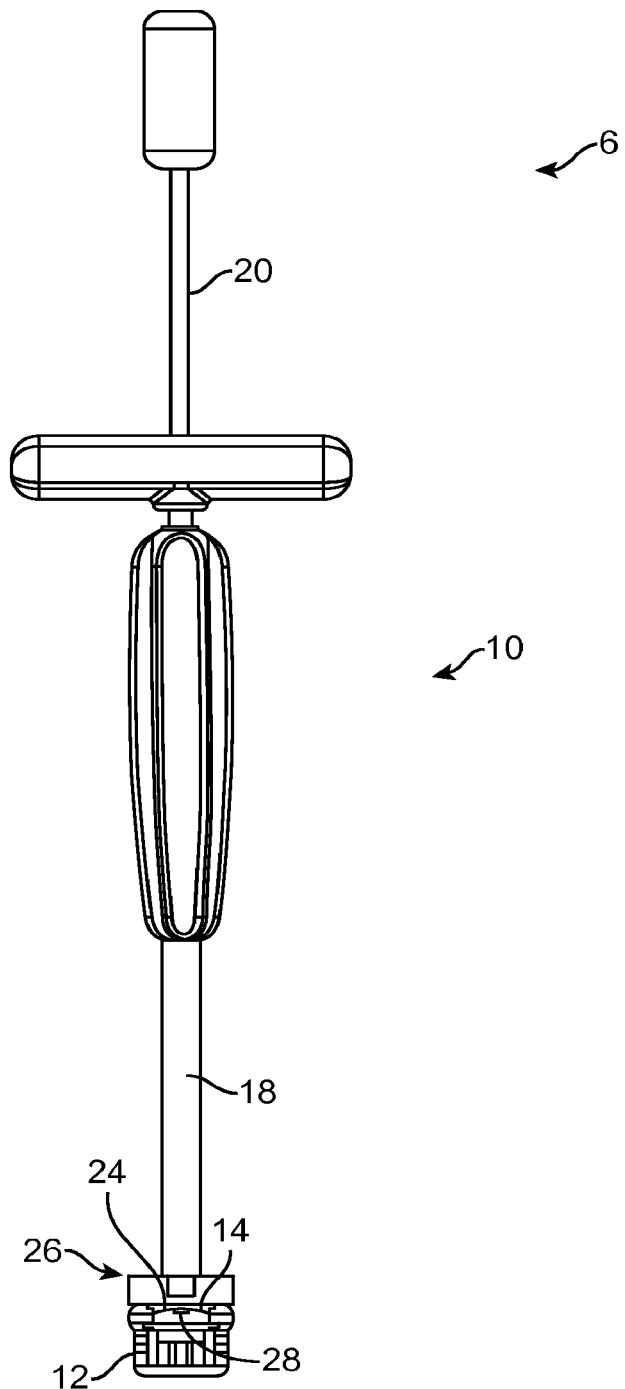
FIG. 4 is a longitudinal bottom plan view of the spinal fusion system and relationships depicted in FIG. 1.
Figure 5:
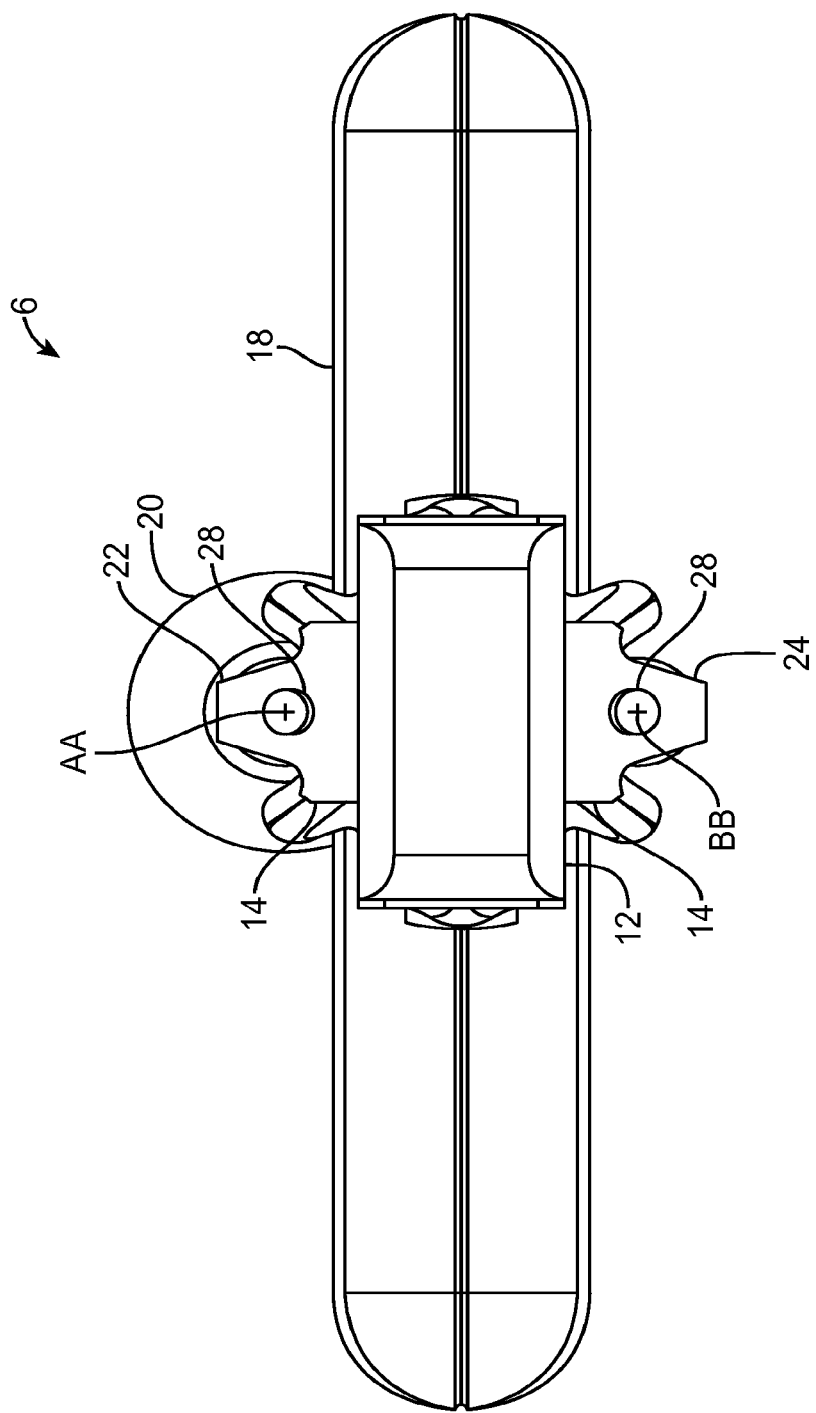
FIG. 5 is a distal end elevation of the spinal fusion system and relationships depicted in FIG. 1.
Figure 6:
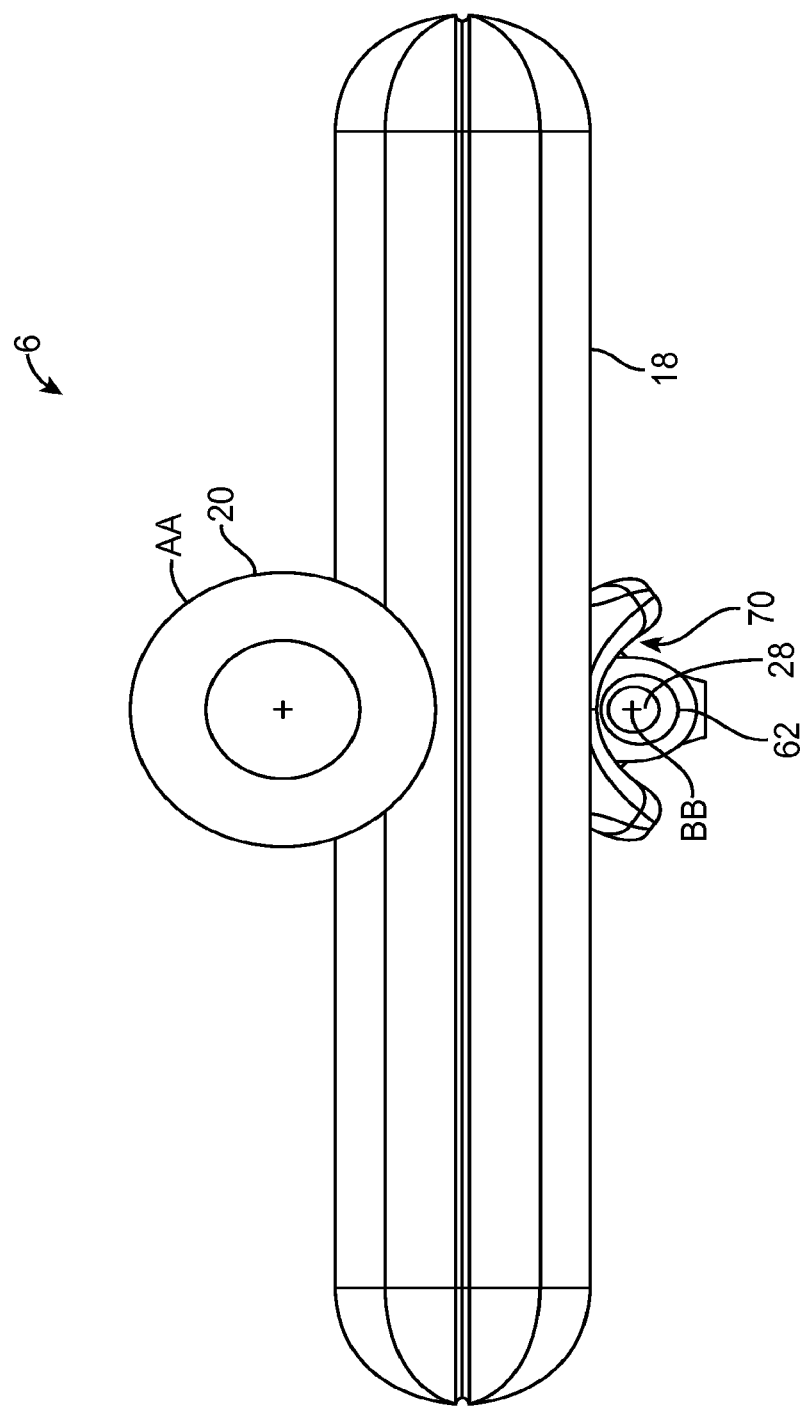
FIG. 6 is a proximal end elevation of the spinal fusion system and relationships depicted in FIG. 1.

Referring to FIG. 1, in one embodiment, a spinal fusion system 6 may include a spinal implant 8 and an implantation tool set 10 for delivering and implanting spinal implants in a spinal column to treat a spinal condition. In one embodiment, the spinal implant 8 includes an interbody fusion cage 12, an anterior fixation plate 14, and bone screws 16 that are received by the fixation plate. The implantation tool set 10 includes an implanter 18 and a screw driver 20.

The cage 12 is designed to be implanted in a disc space between a superior vertebra and an inferior vertebra and to act as a fusion cage system to fix and fuse the superior and inferior vertebrae together. The cage 14 is delivered to the disc space via the implanter 18. When implanted in the disc space, the cage 12 abuts against the superior plate of the inferior vertebra and the inferior plate of the superior vertebra The plate 14 includes a superior blade 22 and an inferior blade 24. The plate 14 is designed to be located within the boundaries of the cage 12 and delivered into the disc space with the cage 1 via the implanter 18. When located both within the boundaries of the cage 12 and the confines of the disc space, the plate 14 is deployed via action of the implanter 18 to penetrate from the disc space into the superior and inferior vertebrae, thereby spanning the two vertebral sections bordering the disc space in which the cage is implanted and preventing the cage from displacing in an anterior-posterior direction or a medial-lateral direction. When the plate 14 is deployed to extend into the superior and inferior vertebrae, the superior blade 22 and the inferior blade 24, respectively, extend superiorly and inferiorly from the boundaries of the cage 12 to respectively penetrate the superior and inferior vertebrae.

The implanter 18 is configured to deliver the fusion cage 12 and the fixation plate 14 positioned within the boundaries of the cage 12 into the disc space. Upon both the cage 12 and plate 14 being implanted in the disc space, the implanter 18 may be used to cause the plate 14 to deploy such that the plate 14 extends into the superior and inferior vertebrae. The screw driver 20, which is guided in its displacement and alignment via the implanter 18, is used to deliver a superior bone screw 16 through an anterior body face of the superior vertebra such that the superior bone screw 16 is received by the superior blade 22. Similarly, the screw driver 20 is used to deliver an inferior bone screw 16 through an anterior body face of the inferior vertebra such that the inferior bone screw 16 is received by the inferior blade 24. Once the bone screws are so received by the plate 14, which extends into the vertebrae bordering the disc space in which the cage 12 is implanted, the implanter 18 ay be decoupled from the implanted cate 12, the interaction of the cage 12, plate 14 and bone screws 16 acting as an implant that fuses the superior and inferior vertebra together.

a) The Spinal Fusion System

To begin a detailed discussion of the spinal fusion system 6, reference is now made to FIGS. 1-6. FIG. 1 is a proximal isometric view of the spinal fusion system 6 with the spinal implant 8 supported on a distal end 26 of the implanter 18, the anterior fixation plate 14 deployed, and the screw driver 20 interfaced with the implanter 18, so as to be properly aligned to guide the first of two bone screws 16 through corresponding receiving openings 28 of the plate 14. FIGS. 2-6 are, respectively, a longitudinal side elevation, a longitudinal top plan view, a longitudinal bottom plan view, a distal end elevation, and a proximal end elevation of the same system 6 and relationships illustrated in FIG. 1. The implantation tool set 10 includes the implanter 18 and a screw driver 20, and the spinal implant 8 includes the interbody fusion cage 12, the anterior fixation plate 14 and bone screws 16. The distal end 26 of the implanter 18 is configured to support the interbody fusion cage 12 and the fixation plate 14 as an integral unit during the implantation of the cage 12 and plate 14 into a disc space located between upper and lower vertebrae defining the disc space. Further, the implanter 18 is used to actuate the fixation plate 14 from a non-deployed state (shown in FIG. 7), where the plate 14 is substantially, if not entirely, located within the confines of the exterior boundaries of the cage 12, to a deployed state (shown in FIGS. 8-9), where the plate 14 extends so as to project substantially past the confines of the exterior boundaries of the cage 12 so as to be capable of penetrating the plates of the immediately adjacent vertebrae and thereby extend into the bodies of said vertebrae.

Figure 10:
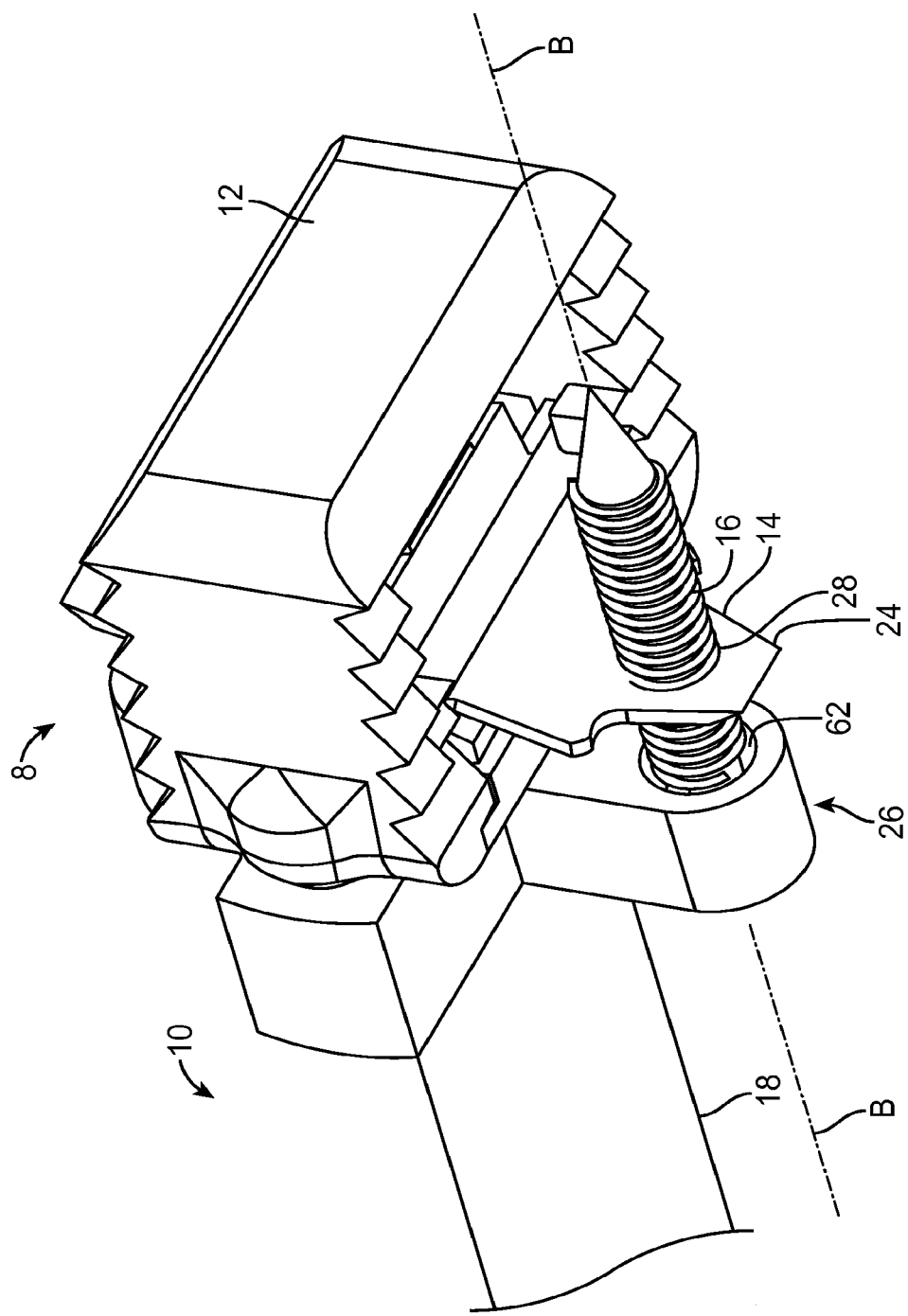
FIG. 10 is an enlarged distal isometric view of the distal end of the spinal fusion system of FIG. 1, showing the spinal implant supported on the distal end of the implanter, with the anterior fixation plate in a deployed state and a bone screw received through an opening in the inferior blade of the fixation plate.

As indicated in FIGS. 1-6, the screwdriver 20 and the implanter 18 are configured to interface in a manner that automatically causes the screwdriver 20 to distally displace along a superior axis A-A that is coaxial with a superior opening 28 in a superior blade 22 of the deployed plate 14, such that a superior screw 16 can be driven "blind" through the superior vertebral body to be received in the superior opening 28 in the superior blade 22 projecting into the superior vertebral body, thereby greatly enhancing the fixation of the superior blade 22 in the superior vertebral body. Similarly, the screwdriver 20 and the implanter 18 are configured to interface in a manner that automatically causes the screwdriver 20 to distally displace along an inferior axis BB that is coaxial with an inferior opening 28 in an inferior blade 24 of the deployed plate 14, such that an inferior screw 16 can be driven "blind" through the inferior vertebral body to be received, as illustrated in FIG. 10, in the inferior opening 28 in the inferior blade 24 projecting into the inferior vertebral body, thereby greatly enhancing the fixation of the inferior blade 24 in the inferior vertebral body. One of the ways in which the spinal fusion system 6 disclosed herein is advantageous is that it facilitates superior fixation that is easily and quickly achieved, resulting in cost savings and a better outcome for the patient.

b) The Implantation Tool Set

Figure 11:
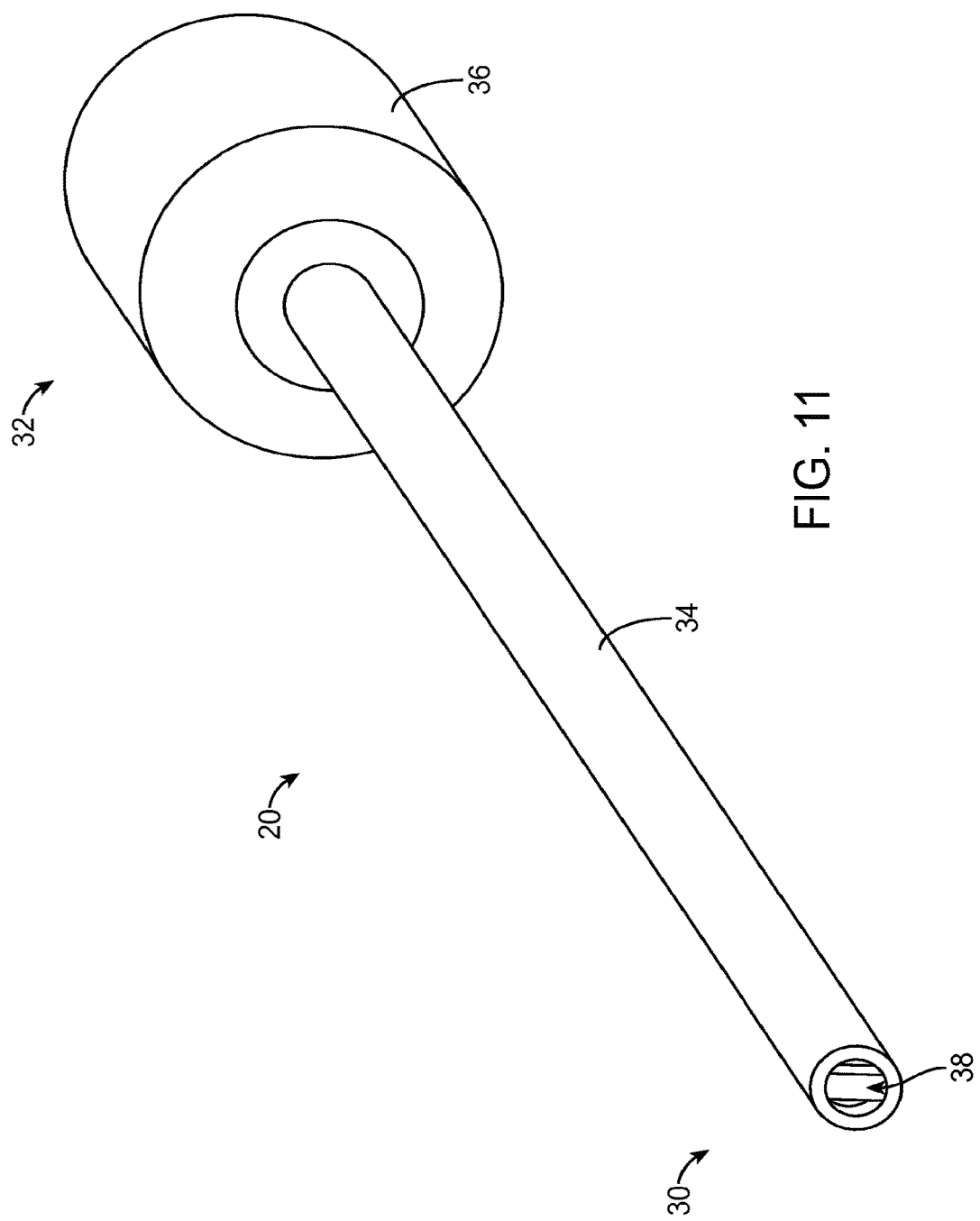
FIG. 11 is a distal isometric view of a screwdriver of an implantation set, according to one embodiment.

To begin a discussion of the details of the components of the implantation tool set 10, reference is made to FIG. 11, which is a distal isometric view of the screwdriver 20. As shown in FIG. 11, the screwdriver 20 includes a distal end 30, a proximal end 32 opposite the distal end 30, an elongated shaft 34 that extends between the ends 30, 32, a gripping handle 36 on the proximal end of the shaft 34, and a screw engagement feature 38 defined in the distal end of the shaft 34. The screw engagement feature 38 may be of any male or female configuration that will allow the screw engagement feature 38 to mechanically engage a proximal region of the bone screw 16, which may be in the formed of a screw head, to allow the screwdriver to be used to drive the bone screw 16 into bone tissue.

Figure 12:
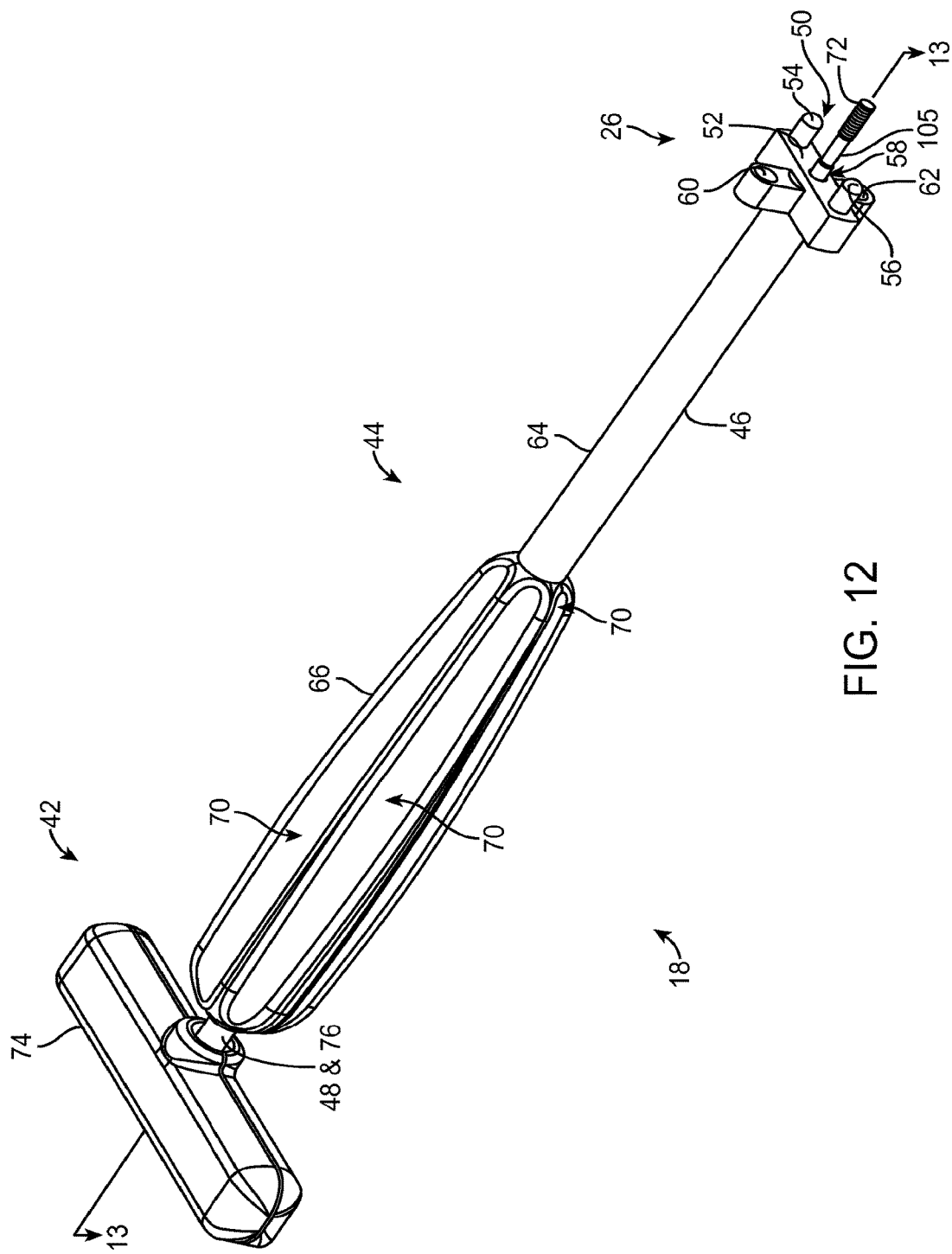
FIG. 12 is a distal isometric view of an implanter of an implantation set, according to one embodiment.

Turning now to another component of the implantation tool set 10, reference is now made to FIG. 12, which is a distal isometric view of the implanter 18. As illustrated in FIG. 12, the implanter 18 includes a distal end 26, a proximal end 42, and an elongated body 44 extending between the distal and proximal ends. As discussed in greater detail below, the distal end 26 is configured to engage the interbody fusion cage 12 and deploy the anterior fixation plate 14, a proximal region of the elongated body 44 is configured for gripping by a first hand, and the proximal end 42 is configured for gripping by a second hand in bringing about the deployment of the fixation plate 14.

Figure 13:
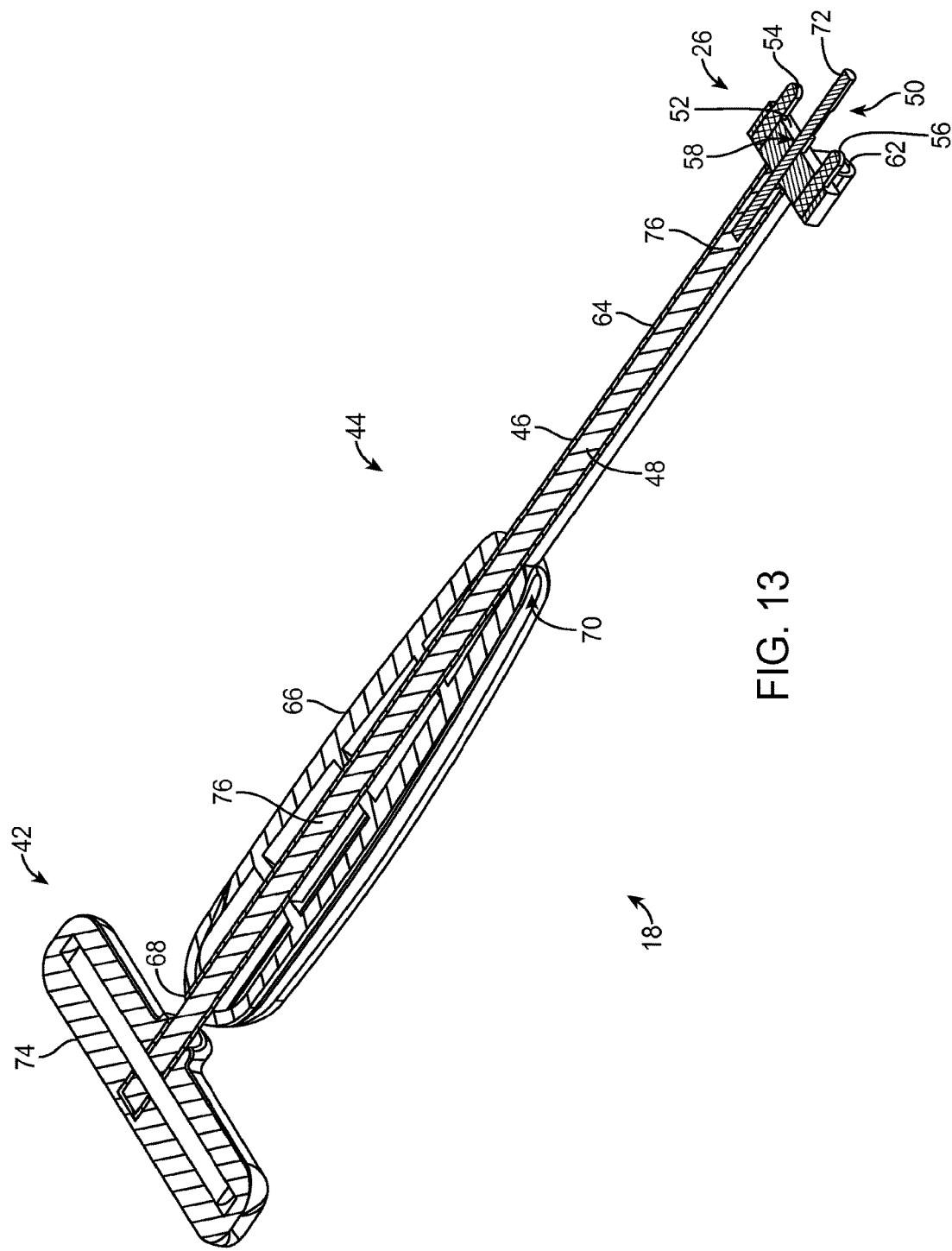
FIG. 13 is a longitudinal cross-sectional view of the implanter of FIG. 12, as taken along section line 13-13 of FIG. 12.

As depicted in FIG. 13, which is the same view of the implanter 18 of FIG. 12, except the implanter 18 is shown in a longitudinal cross section as taken along section line 13-13 in FIG. 12, the implanter 18 includes an outer assembly 46 and an inner assembly 48 coaxially positioned within the outer assembly 46 and rotationally displaceable within the outer assembly 46 about a common longitudinal axis of the outer and inner assemblies 46, 48. As can be understood from FIGS. 12 and 13, the outer assembly 46 at the distal end 26 includes a cage interface 50 adapted for coupling with fusion cage 12 in securing the fusion cage 12 to the distal end 26 of the implanter 18. The cage interface 50 includes a generally planar distal face 52, a first projection 54 distally projecting from the distal face 52, a second projection 56 distally projecting from the distal face and laterally offset from the first projection 54, a center opening 58 generally centered between the first and second projections 54, 56, a superior guide channel or opening 60, and an inferior guide channel or opening 62. The respective center axes of the first projection 54, the second projection 56, and the center opening 58 are positioned along a single lateral line with the center opening 58 located half-way between the first and second projections 54, 56. The superior guide 60, the inferior guide 62, and the center opening 58 are positioned along a single superior-inferior line that is perpendicular to the signal lateral line associated with the projections 54, 56, and the center opening 58 located half-way between the superior and inferior guides 60, 62.

As illustrated in FIGS. 1, 2, and 8-10, the superior and inferior guides 60, 62 guide the respective bone screws 16 along the respective axes AA and BB as the screwdriver 20 is used to distally drive the screws 16 into the openings 28 of the respective superior and inferior blades 22, 24 of the deployed fixation plate 14. The projections 54, 56 are received in the fusion cage 12 near the extreme lateral boundaries of the cage 12.

Figure 14:
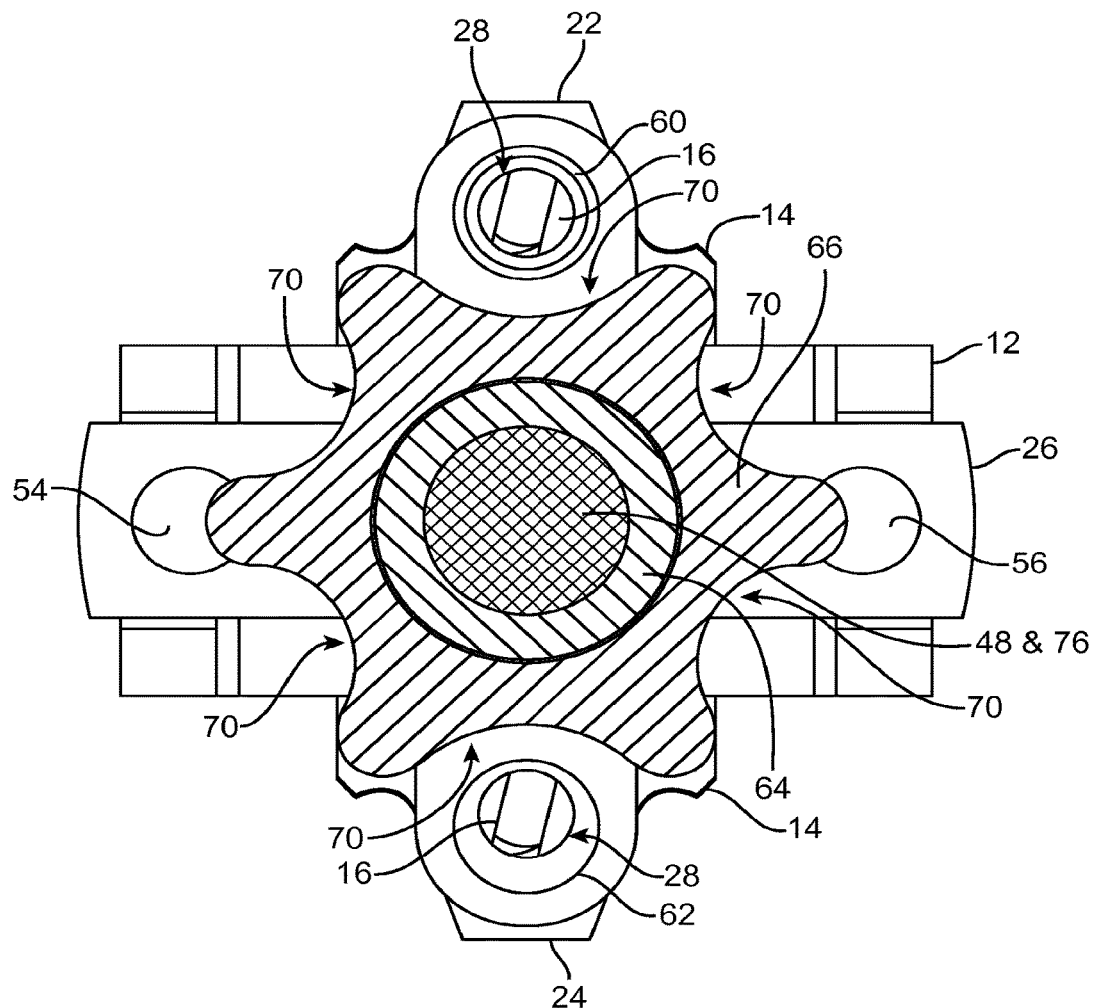
FIG. 14 is a lateral or transverse cross section of the implanter, as taken along section lines 14-14 in FIG. 1.

As indicated in FIGS. 12 and 13, outer assembly 46 further includes an elongated tubular body 64 and a grasping handle 66. The tubular body 64 extends proximally from the cage interface 50 and the distal end 26 towards a proximal end 68 of the tubular body 64. The grasping handle 66 extends about a proximal region of the tubular body 64. The handle 66 includes six channels, slots, grooves or other features 70 longitudinally extending along the handle 66 and evenly circumferentially distributed about the handle 66. In some embodiments, the number of grooves 70 may be more or less than six. As illustrated in FIG. 14, which is a lateral or transverse cross section of the implanter 18 as taken along section lines 14-14 in FIG. 1, regardless of the number of grooves 70 in the handle 66, one groove 70 will be axially aligned with the superior guide 60 and one groove 70 will be axially aligned with the inferior guide 62. As a result and as can be understood from FIGS. 1-3, the groove 70 guides the screwdriver 20 as the screwdriver shaft 34 distally displaces along the groove 70 to drive the bone screw 16 through the guide 60, 62 and blade opening 28 with which screwdriver 20 and screw 16 are aligned via the groove 70 and applicable guide 60, 62. Thus, the handle grooves 70 in combination with the guides 60, 62 interact with the screwdriver 20 to guide the screwdriver distal displacement along the applicable axes AA, BB to allow for "blind" delivery of the screws 16 into the openings 28 of the blades 22, 24 of the fixation plate 14 that has been deployed in the respective vertebrae bordering the disc space occupied by the cage 12 delivered via the implanter 18.

As depicted in FIGS. 12 and 13, the inner assembly 48 includes a threaded distal termination 72, a proximal T-handle 74 and an elongated shaft 76 that extends between the T-handle 74 and the threaded distal termination 72.

The elongated shaft 76 extends longitudinally through, and coaxially with, the outer assembly tubular body 64. A proximal portion of the shaft 76 projects proximally from the tubular body 64 to extend into the T-handle 74, and a distal portion of the shaft 76 projects distally through the central opening 58 to transition into the threaded distal termination 72. The elongated shaft 76 is rotationally displaceable within the outer assembly tubular body 64 about a common longitudinal axis of the outer and inner assemblies 46, 48. Thus, the T-handle 74 and grasping handle 66 can each be gripped, and the T-handle 74 can be used to cause the inner assembly 48 to rotationally displace within the outer assembly 46 to thread the threaded distal termination 72 in a threaded engagement with a drive nut of the fixation plate 14 to cause the fixation plate to deploy or un-deploy as needed within the confines of the cage 12 coupled to the distal end of the outer assembly 46.

In one embodiment, the screw driver 20 and the implanter 18 are separate devices. In another embodiment, one or more screw drivers 20 and the implanter 18 may be integrated together to form a single integrated structure or device.

Figure 15:
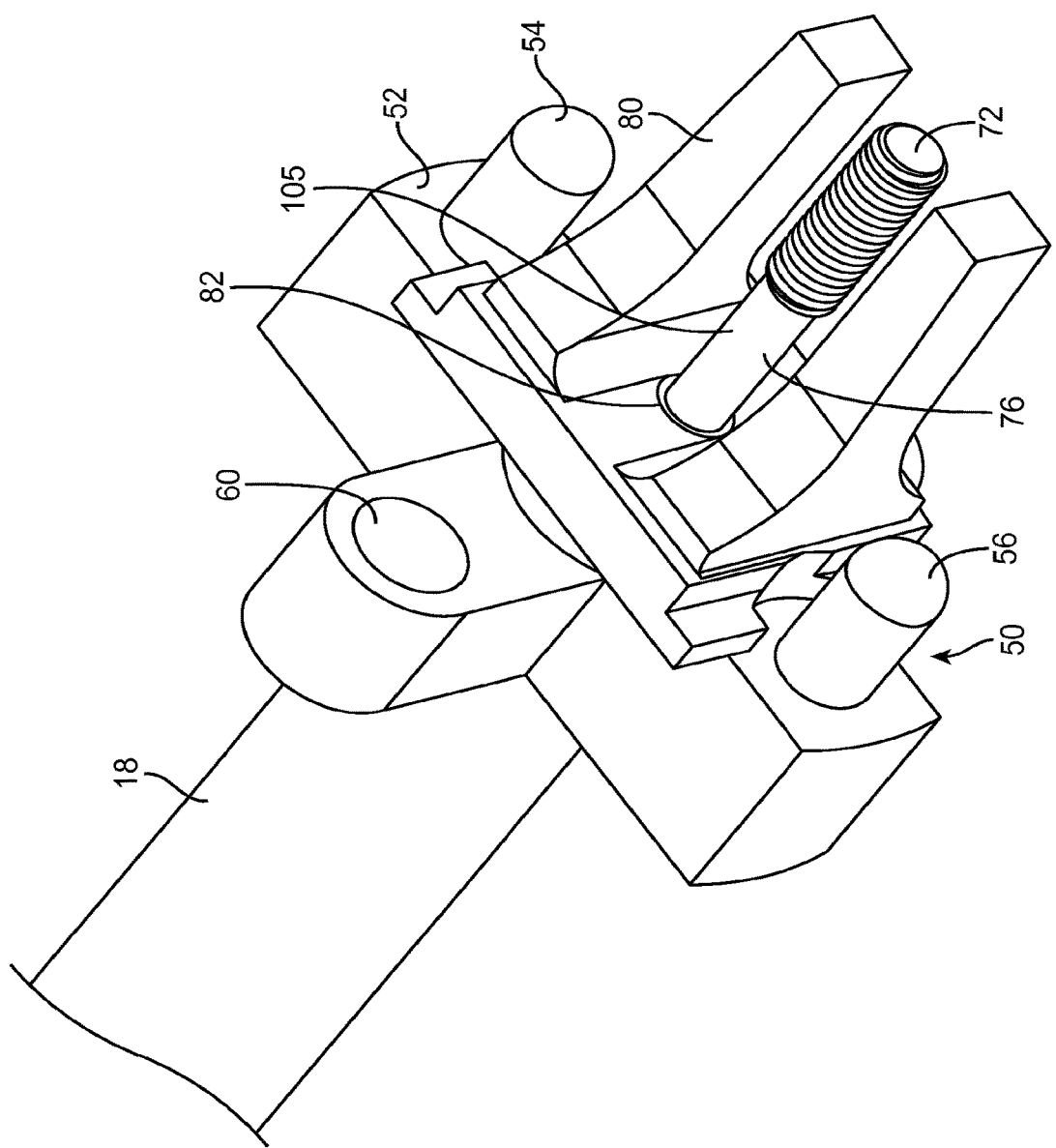
FIG. 15 is an enlarged distal isometric view of the implanter distal end, wherein a deployment ramp extends distally from the distal face of the cage interface of the implanter.
Figure 16:
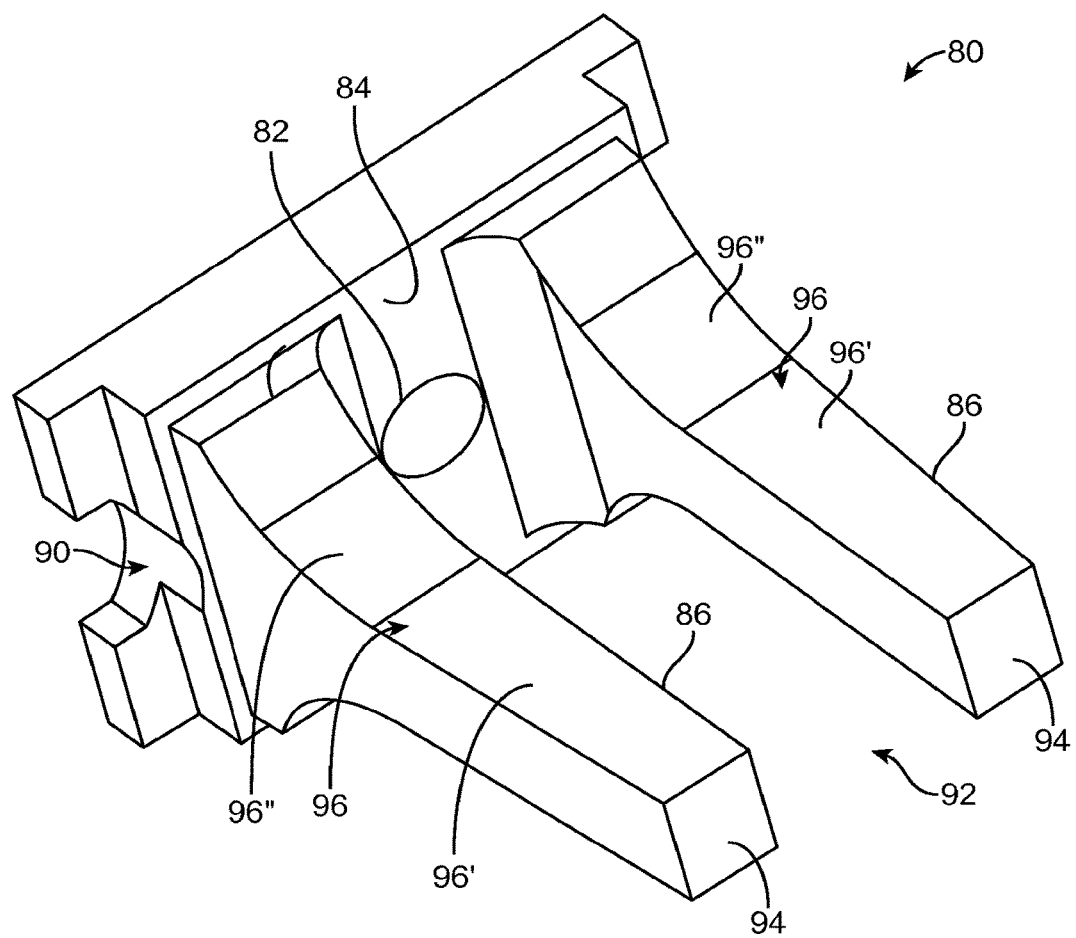
FIG. 16 is a distal isometric view of the deployment ramp depicted in FIG. 15.
Figure 17:
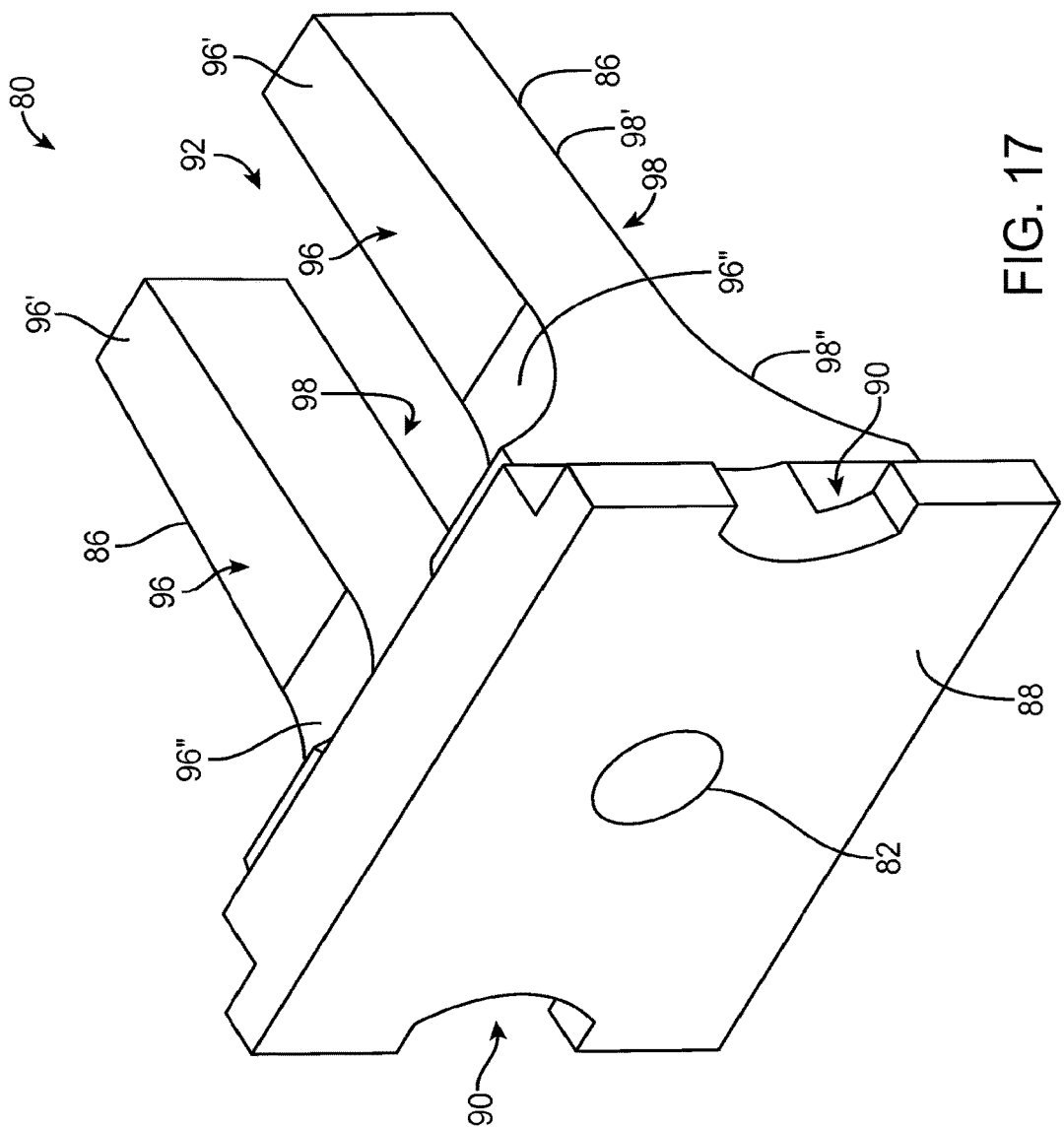
FIG. 17 is a proximal isometric view of the deployment ramp.
Figure 18:
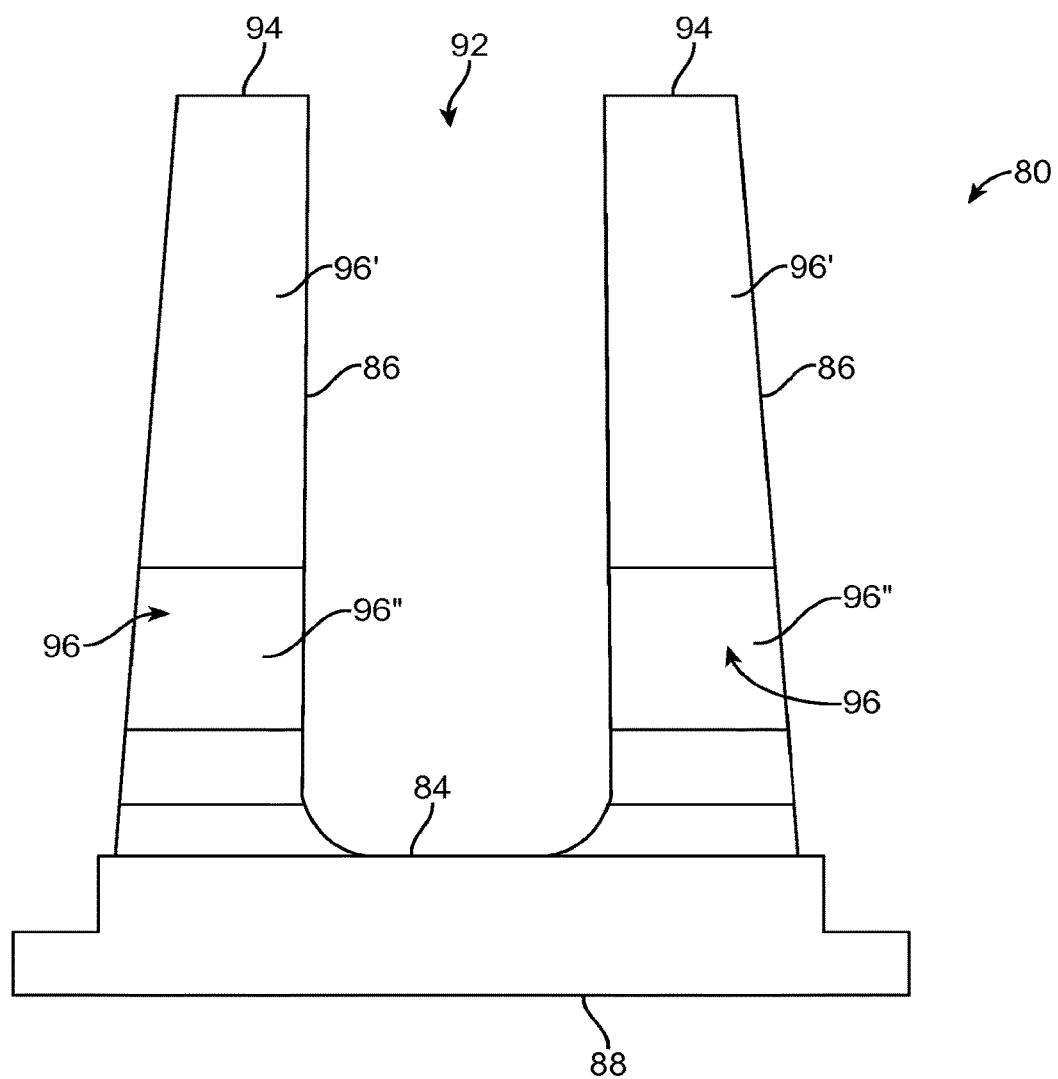
FIG. 18 is a superior plan view of the deployment ramp, the superior plan view being identical to what would be an inferior plan view.
Figure 19:
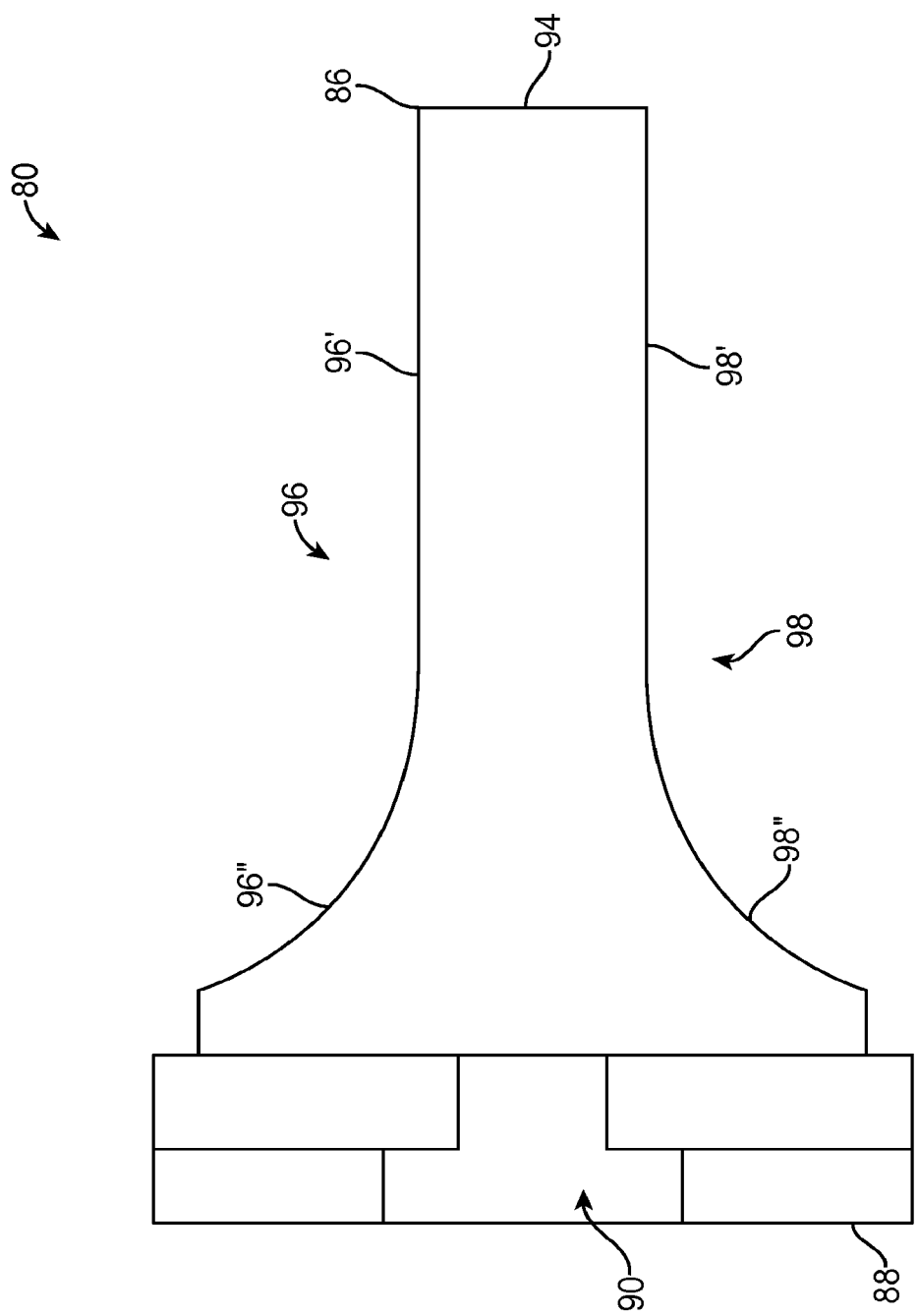
FIG. 19 is a lateral side elevation of the deployment ramp, the deployment ramp having the identical appearance if view from an opposite side of the ramp.
Figure 20:
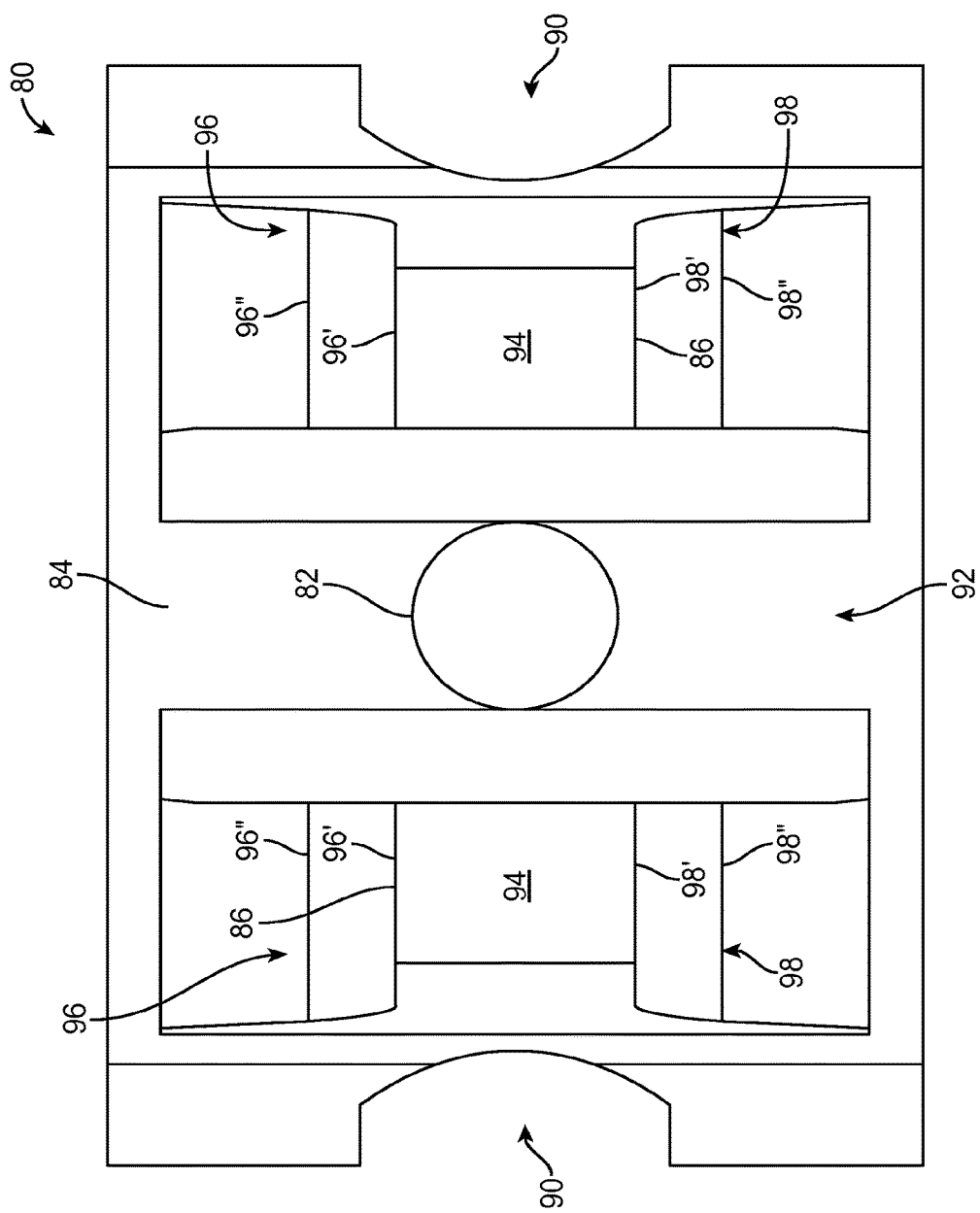
FIG. 20 is a distal elevation of the deployment ramp.
Figure 21:
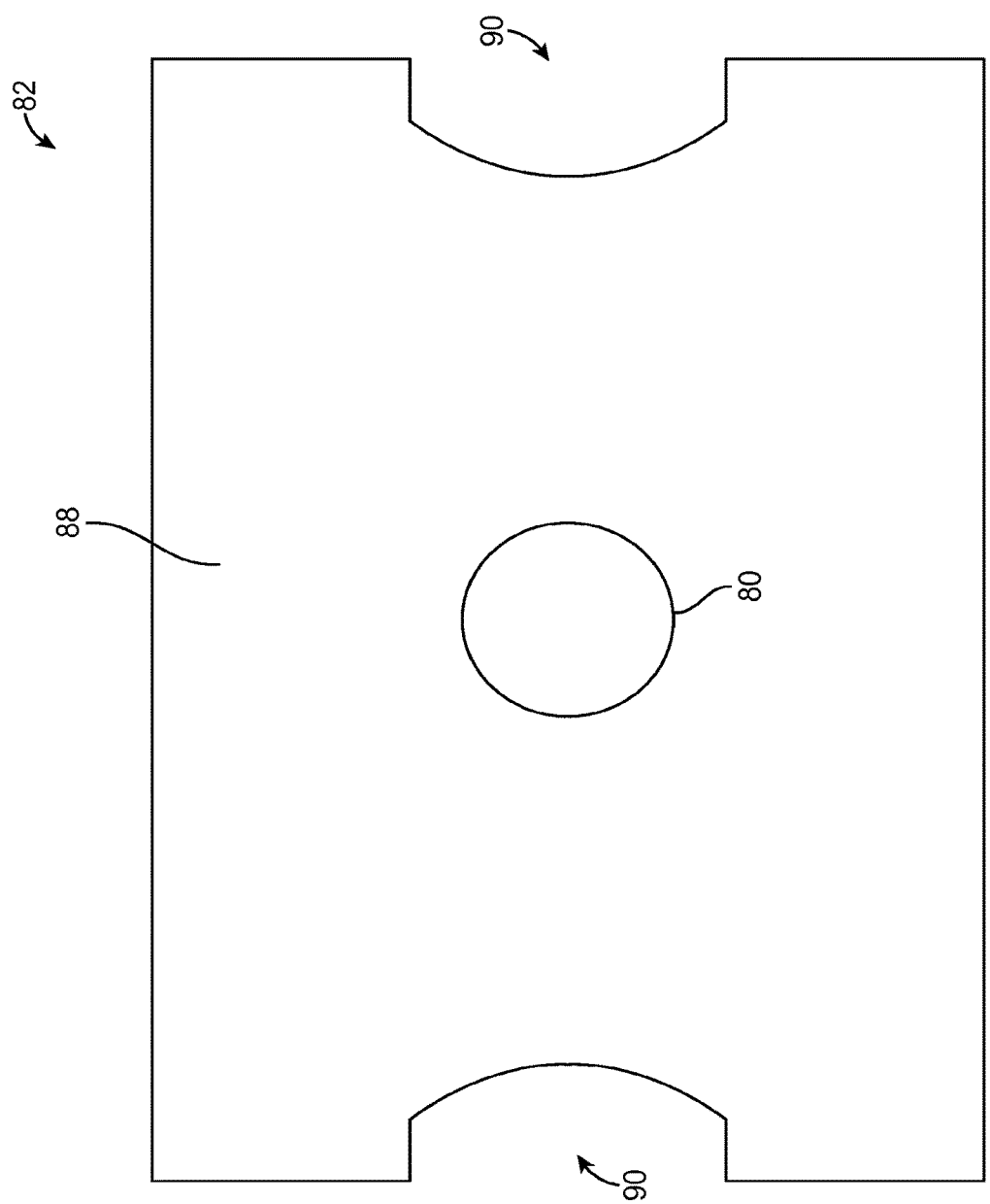
FIG. 21 is a proximal elevation of the deployment ramp.
Figure 22:
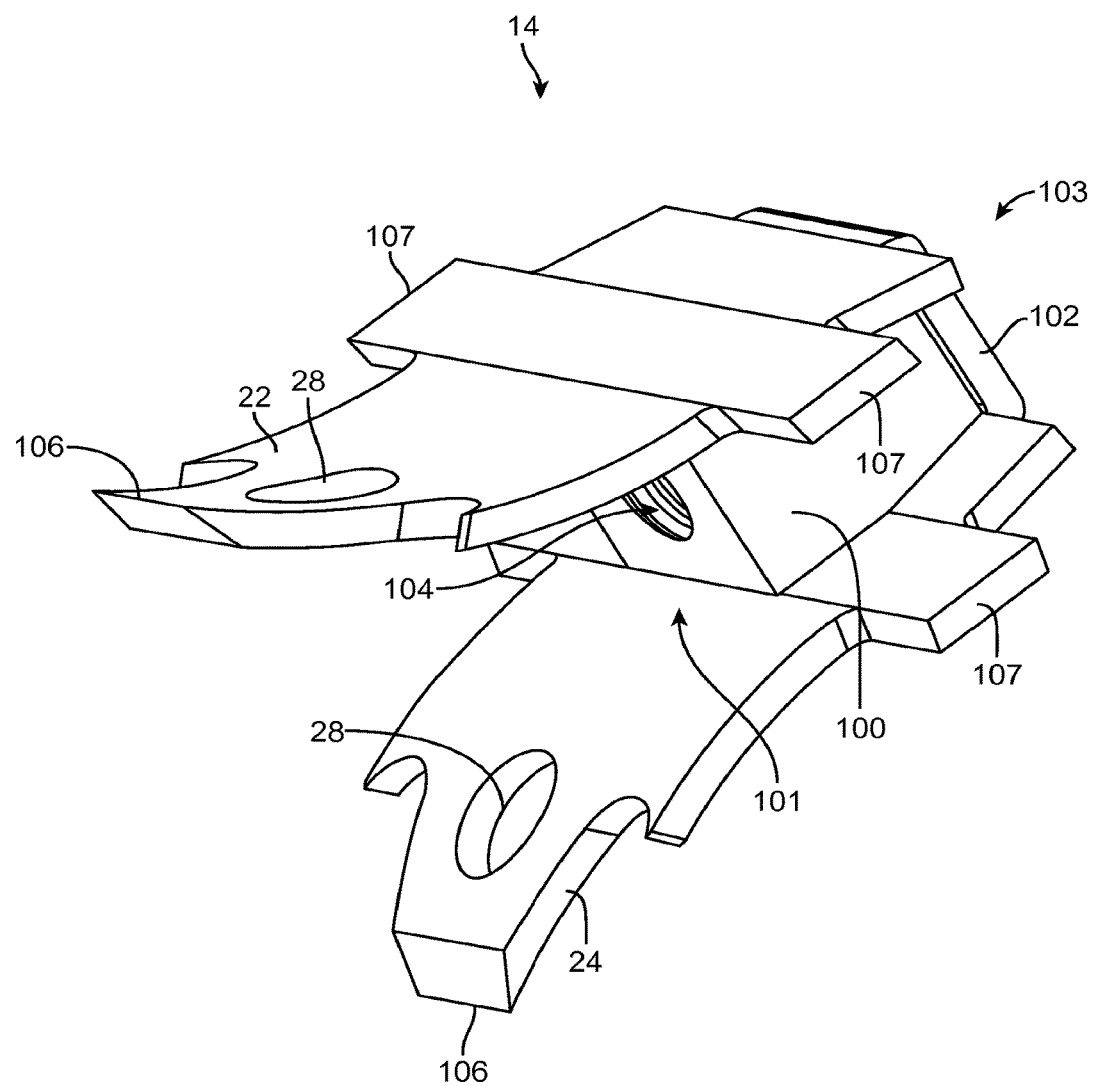
FIG. 22 is a proximal isometric view of an anterior fixation plate in a non-deployed state, according to one embodiment.
Figure 23:
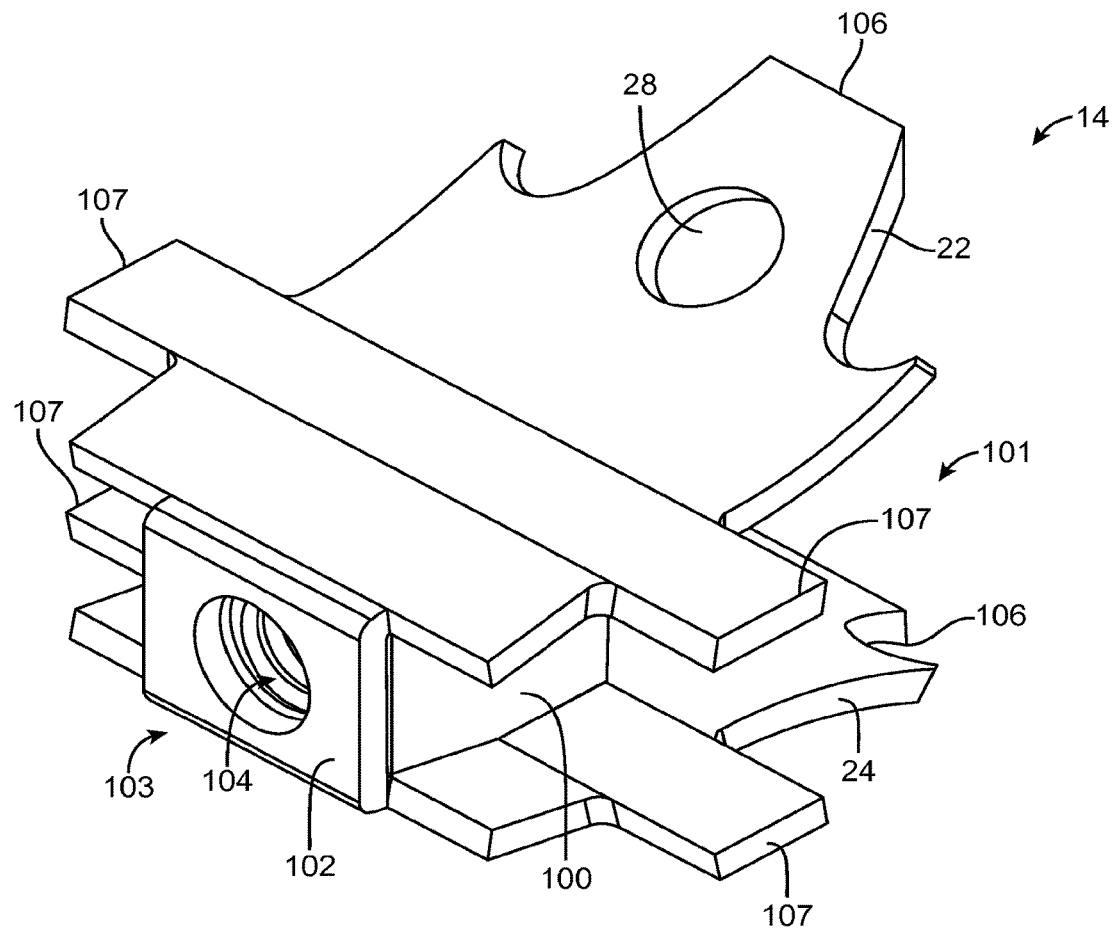
FIG. 23 is a distal isometric view of the anterior fixation plate in the non-deployed state.

Turning now to the yet another component of the implantation tool set 10, reference is now made to FIG. 15, which is an enlarged distal isometric view of the implanter distal end 26, wherein a deployment ramp 80 extends distally from the distal face 52 of the cage interface 50 of the implanter 18. As shown in FIG. 15, the deployment ramp 80 abuts up against the distal face 52 of the cage interface 50, is positioned between the pair of projections 54, 56 and the pair or guides 60, 62, and the elongated shaft 76 distally projects through a center opening 82 in the ramp 80 that is axially aligned with the central opening 58 of the cage interface 50 of the implanter 18. The ramp 80 spreads the blades 22, 24 of the plate 14 apart into the deployed state depicted in FIGS. 1, 2, 8 and 9 when the threaded distal termination 72 is rotated so as to draw the plate 14 against the ramp 80, as described in greater detail below.

As shown in FIGS. 16-21, which are, respectively, a distal isometric view, a proximal isometric view, a superior plan view, a lateral side elevation, a distal elevation, and a proximal elevation of the deployment ramp 80, in one embodiment, the deployment ramp 80 includes the central opening 82, a distal face 84 from which laterally space-apart projections or arms 86 distally project, a generally planar proximal face 88, and lateral notches 90 opening in opposite directions from each other and located between the distal face 84 and the proximal face 88. The central opening 80 extends proximal-distal to daylight in the two faces 84, 88. The two arms 86 are laterally spaced apart from each other evenly on each side of the central opening 82 to define a gap 92 through which the threaded distal termination 72 of the elongated shaft 76 projects, as indicated in FIG. 15. Also, as indicate in FIG. 15, the notches 90 are generally axially aligned with the projections 54, 56 such that the projections 54, 56 extend through said notches 90.

As depicted in FIGS. 16-20, each arm 86 distally terminates in a distal end face 94 and includes a superior surface 96 and an inferior surface 98 opposite the superior surface 96 in a superior-inferior direction, and the arms 86 have generally identical configurations to each other. As best understood from FIG. 19, each said surface 96, 98 includes a level region 96', 98' that is parallel to the level region 96', 98' opposite the arm 86 in a superior-inferior direction.

Additionally, each said surface 96, 98 also includes a sloped region 96", 98" that curves oppositely to the sloped region 96", 98" opposite the arm 86 in a superior-inferior direction. As can be understood from FIGS. 7-9 and discussed more fully below, the ramping or deployment surfaces 96, 98 of the deployment ramp 80 are acted against by the inside surfaces of the blades 22, 24 of the fixation plate 14 as the plate 14 is proximally driven against the ramp 80 when the threaded distal termination 72 threadably draws a threaded drive but 100 of the plate 14 proximally within the cage 12 and between the arms 86.

c. The Spinal Implant

Figure 24:
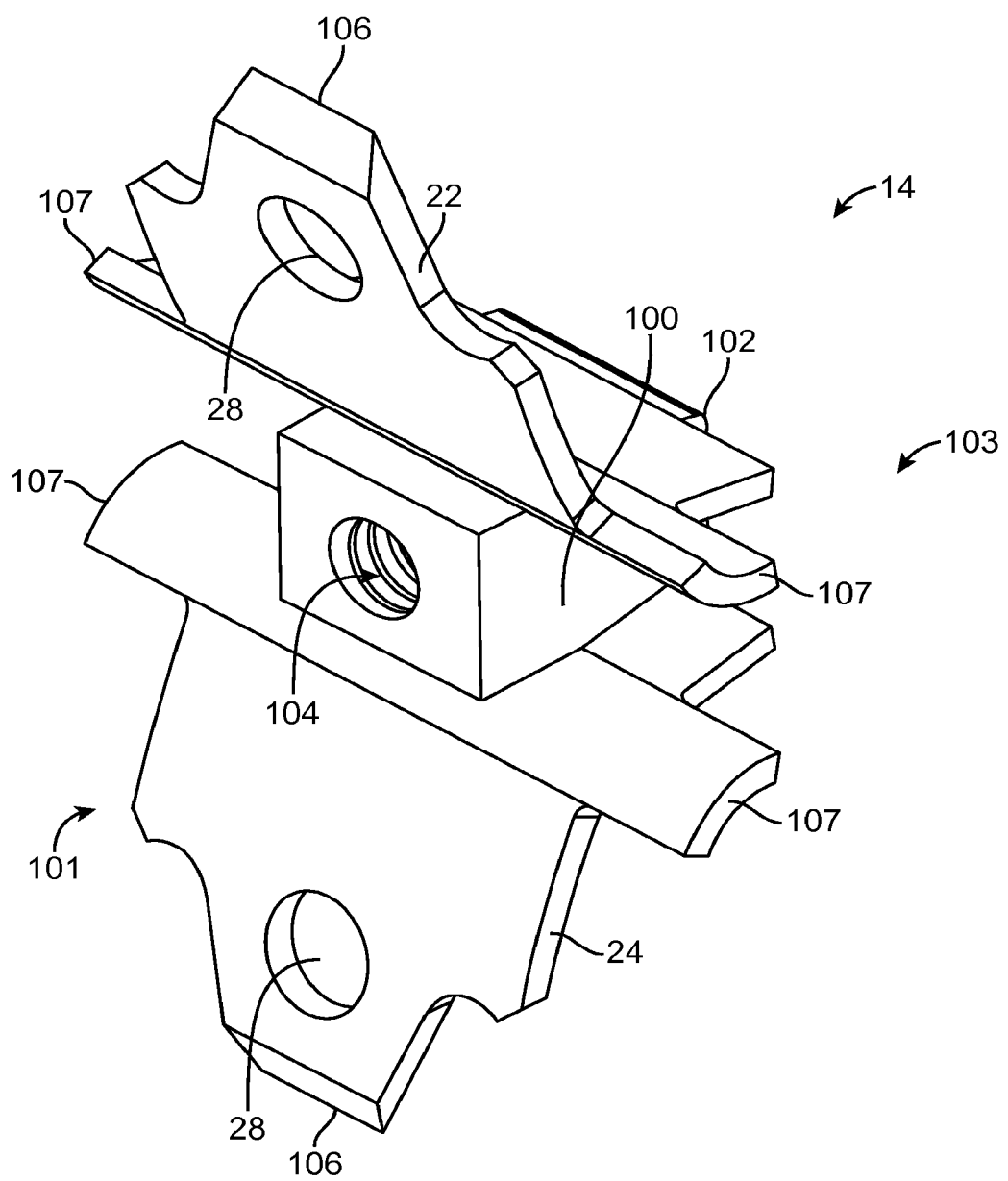
FIG. 24 is a proximal isometric view of the anterior fixation plate in a deployed state.
Figure 25:
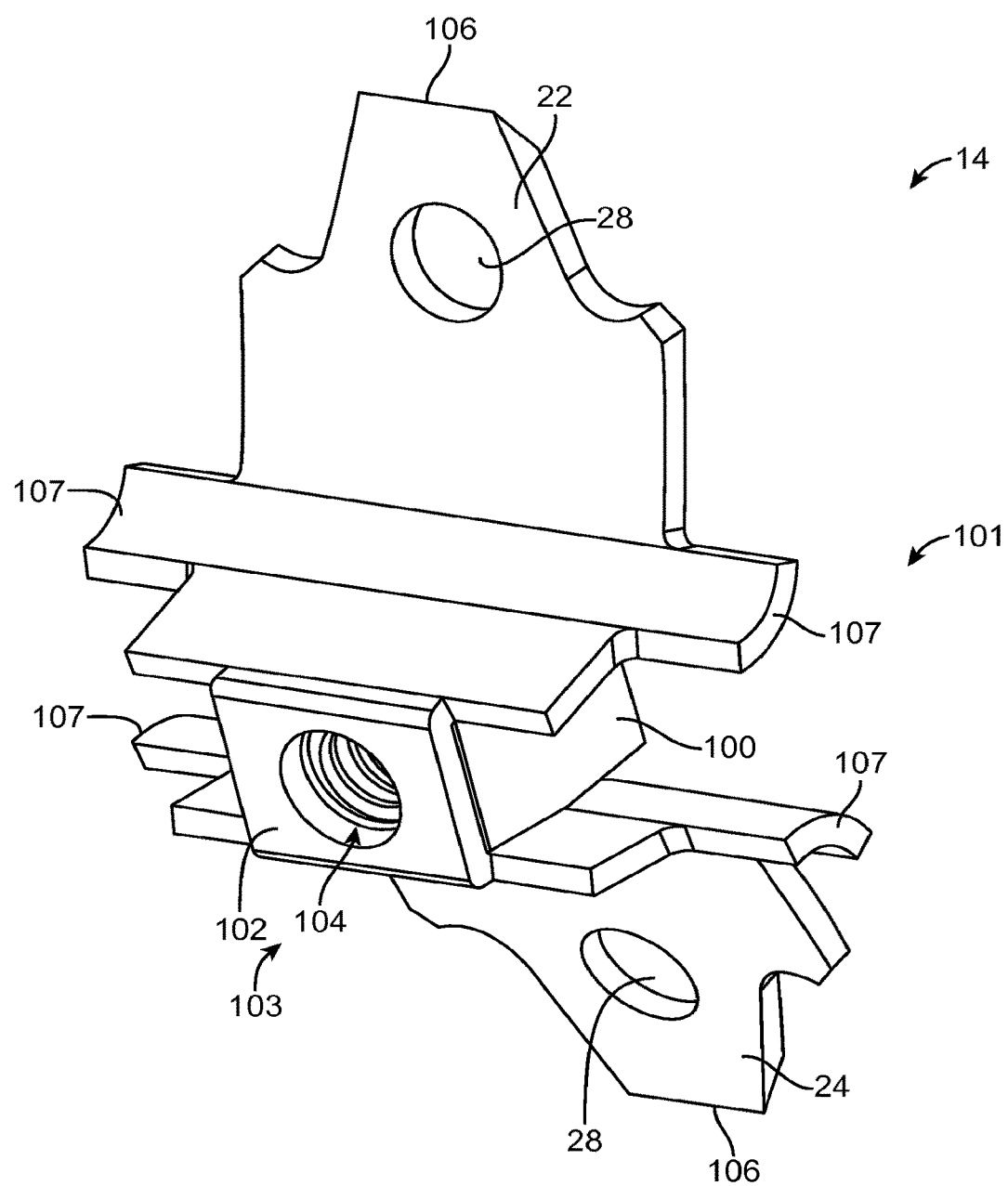
FIG. 25 is a distal isometric view of the anterior fixation plate in a deployed state.

To begin a discussion of the details of the components of the spinal implant 8, reference a made to FIGS. 22-25 are, respectively, a proximal isometric view and a distal isometric view of the anterior fixation plate 14 in the non-deployed state. FIGS. 24-25 are, respectively, a proximal isometric view and a distal isometric view of the anterior fixation plate 14 in the deployed state. As shown in FIGS. 22-25, the fixation plate 14 includes a superior blade 22, an inferior blade 24, a proximal side 101, an intermediate or joining portion 102, a distal side 103, and a threaded drive nut 100. The distal side 103 is opposite the proximal side 101, which faces the implanter 18 when coupled to the implanter 18.

In some embodiments, the blades 22, 24 and the intermediate portion 102 can be a one-piece, unitary structure formed from a signal sheet piece of biocompatible material such as, e.g., stainless steel, titanium, etc., that is bent or otherwise formed into a one-piece, unitary structure plate 14. In other embodiments, the blade 14 is a multi-element construction formed of one or more separate sheet pieces of biocompatible material that is joined together via, e.g., any of a variety of welding procedures (e.g., laser, chemical, resistance, cold, etc.) or mechanically fastened together (e.g., crimping, etc.). The threaded drive nut 100 may be permanently joined to the intermediate portion 102 via any of the aforementioned methods, or the threaded drive nut 100 may even be an unitary structure with the intermediate portion 102 or even the blades 22, 24, depending on the embodiment.

As illustrated in FIGS. 22-25, each blade 22, 24 includes a sharp extreme free edge 106 that has sufficient sharpness and rigidity to allow the blade to penetrate the end plate of an adjacent vertebral body. Also, each blade 22, 24 includes an opening 28 through which a bone screw 16 is received via "blind" delivery of the bone screw when the blade 22, 24 extends into the vertebral body, as discussed above with respect to FIGS. 1-3 and 8-10. Further, each blade 22, 24 includes a pair of extreme lateral wings 107 that interact with features of the cage 12 as described below to prevent anterior-posterior and lateral displacement of the cage 1 and fixation plate 14 when the plate 14 is in the deployed state.

Figure 8:
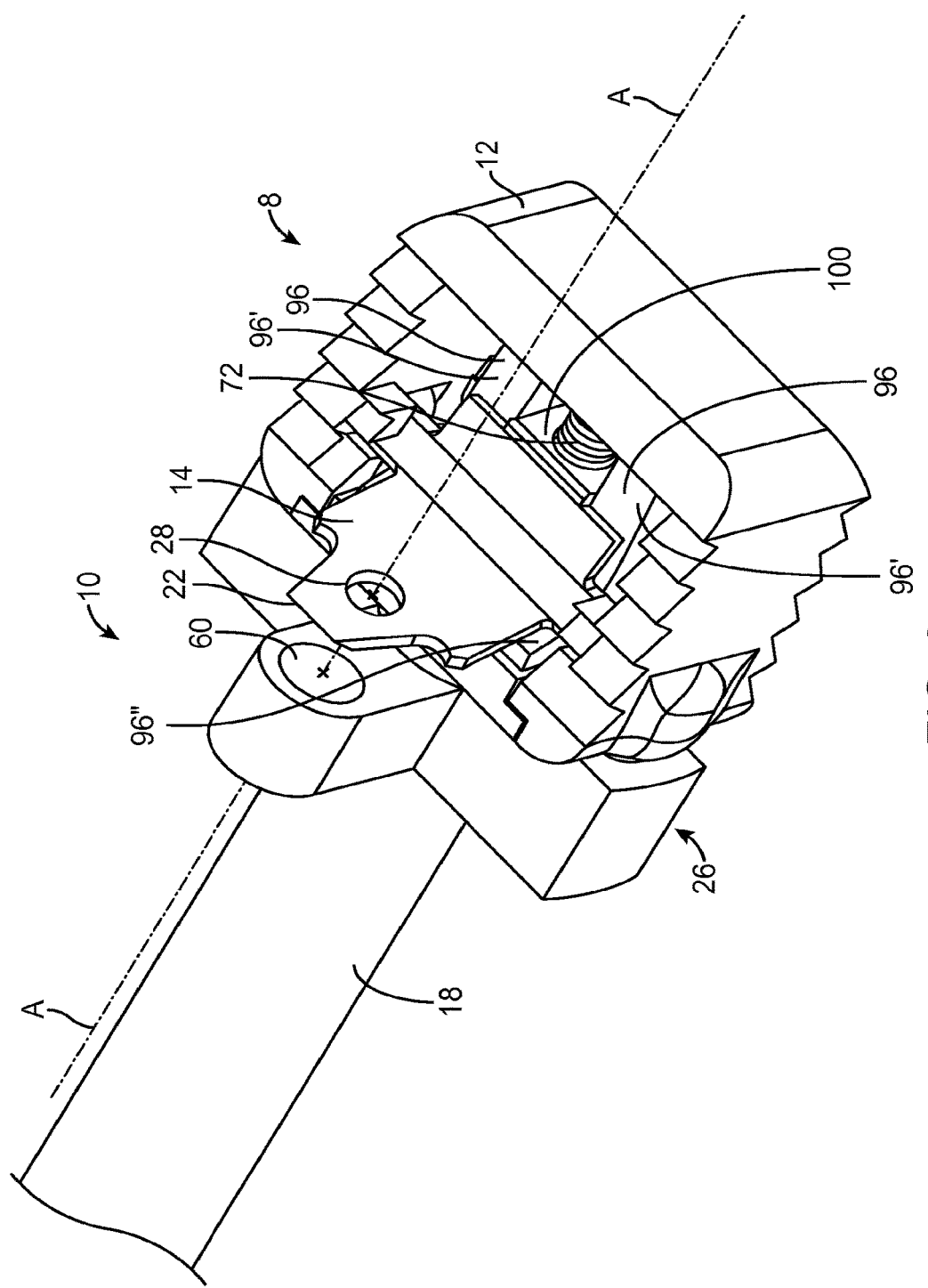
FIG. 8 is the same enlarged distal isometric view of FIG. 7, except the anterior fixation plate is in a deployed state, such that the fixation plate extends so as to project substantially past the confines of the exterior boundaries of the interbody fusion cage, so as to be capable of penetrating the end plates of the immediately adjacent vertebrae and thereby extend into the bodies of said vertebrae.
Figure 26:
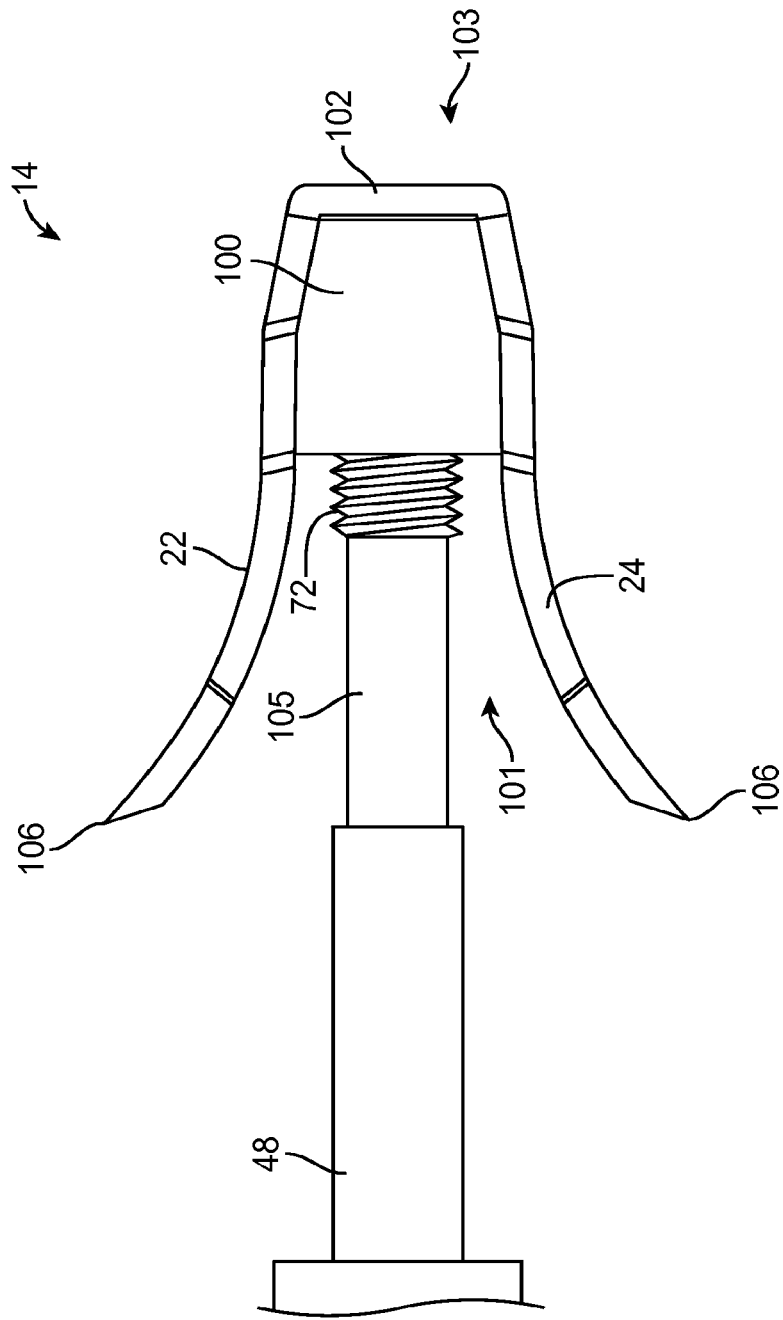
FIG. 26 is a lateral side elevation of the fixation plate threadably engaged with the threaded distal termination of the implanter in the non-deployed state, according to one embodiment.
Figure 27:
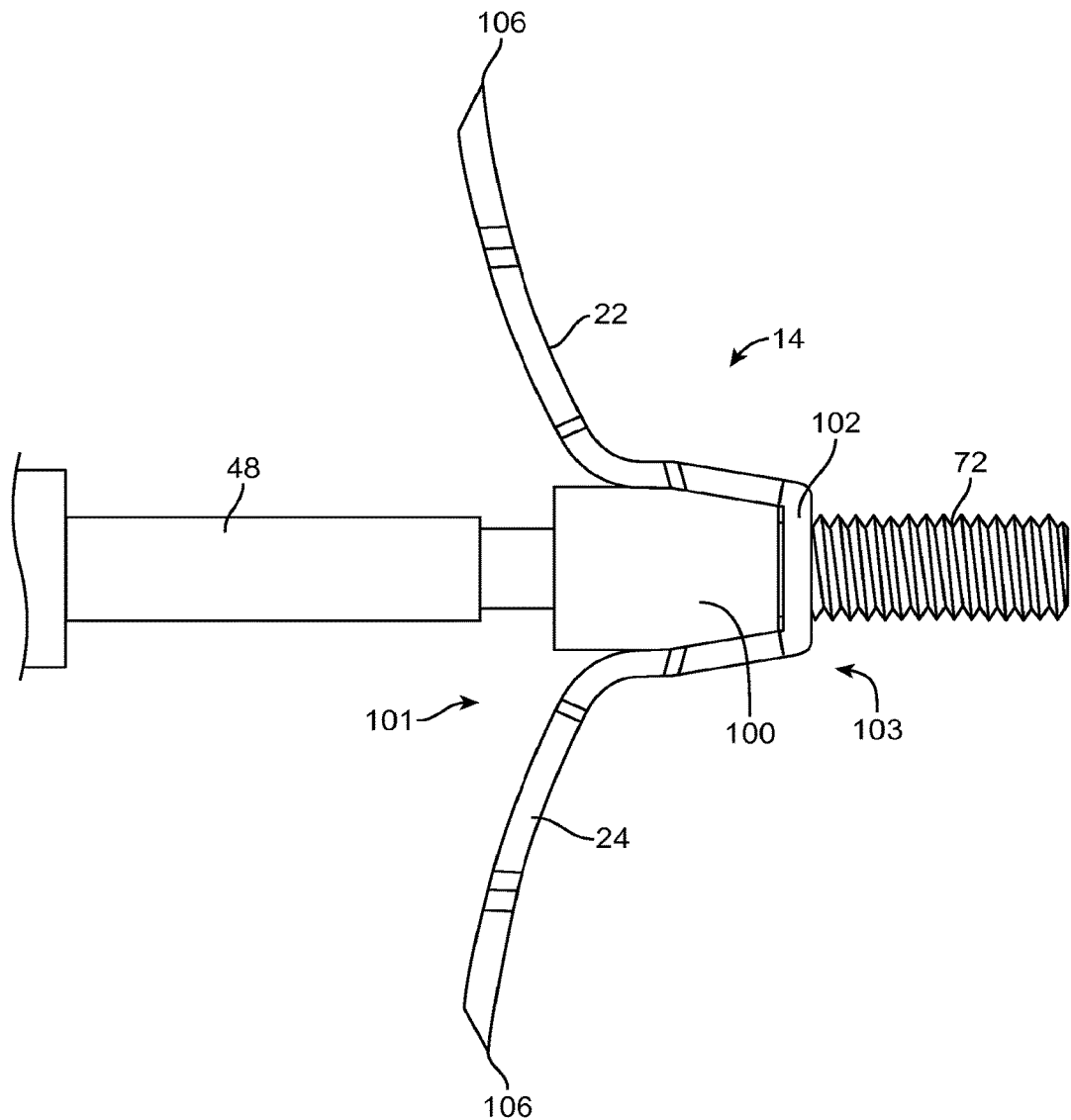
FIG. 27 is the same view as FIG. 26, except the fixation plate is in the deployed state.

The drive nut 100 includes a threaded hole 104 that is threadably engaged by the threaded distal termination 72 of the inner assembly 48 of the implanter 18, as can be understood from FIG. 8. As illustrated in FIGS. 26 and 27, which are lateral side elevations of the fixation plate 14 threadably engaged with the threaded distal termination 72 in the non-deployed and deployed states, respectively, threading of the threaded distal termination 72 within the threaded hole 104 of the drive nut 100 in a first direction causes the drive nut 100 to displace proximally along the length of the threaded distal termination 72, thereby driving the fixation plate 14 proximally. Reversing the threading direction may cause the drive nut 100 to displace distally along the length of the threaded distal termination 72, thereby driving the fixation plate 14 distally. Alternatively, reversing the threading direction may cause decoupling of the threaded distal termination 72 and the drive nut 100, thus, decoupling the implanter 18 from the implant 8.

Referring to FIG. 26, in one embodiment, a non-threaded portion 105 of the inner assembly 48 of the insertion tool 18 is immediately proximal of the threaded distal termination 72, thereby providing a limit to further proximal displacement of the drive nut 100 and, as a result, a limit on further proximal displacement of the plate 14. This limit 105 provides a tactile feedback to the user that the plate 14 has deployed completely.

Figure 28:
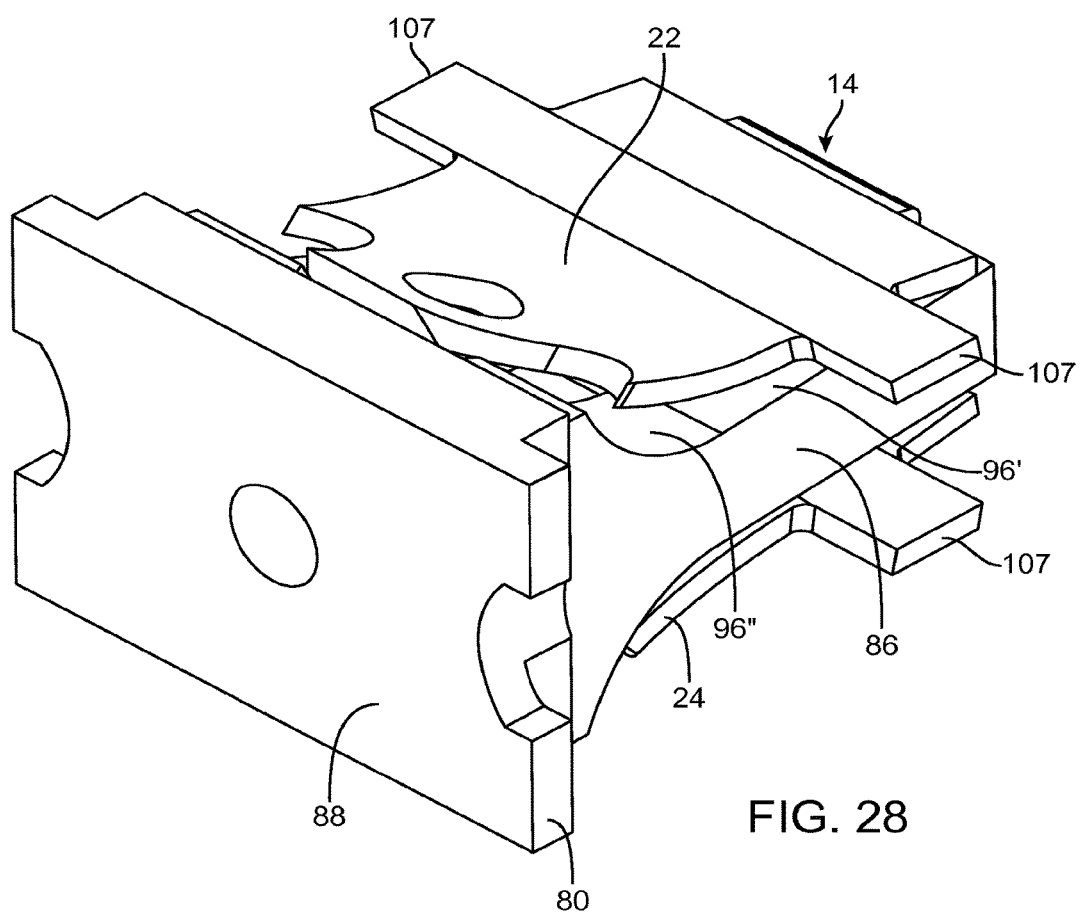
FIG. 28 is a proximal isometric view of the interaction of the plate and ramp when the plate is in the non-deployed state of FIG. 26.
Figure 29:
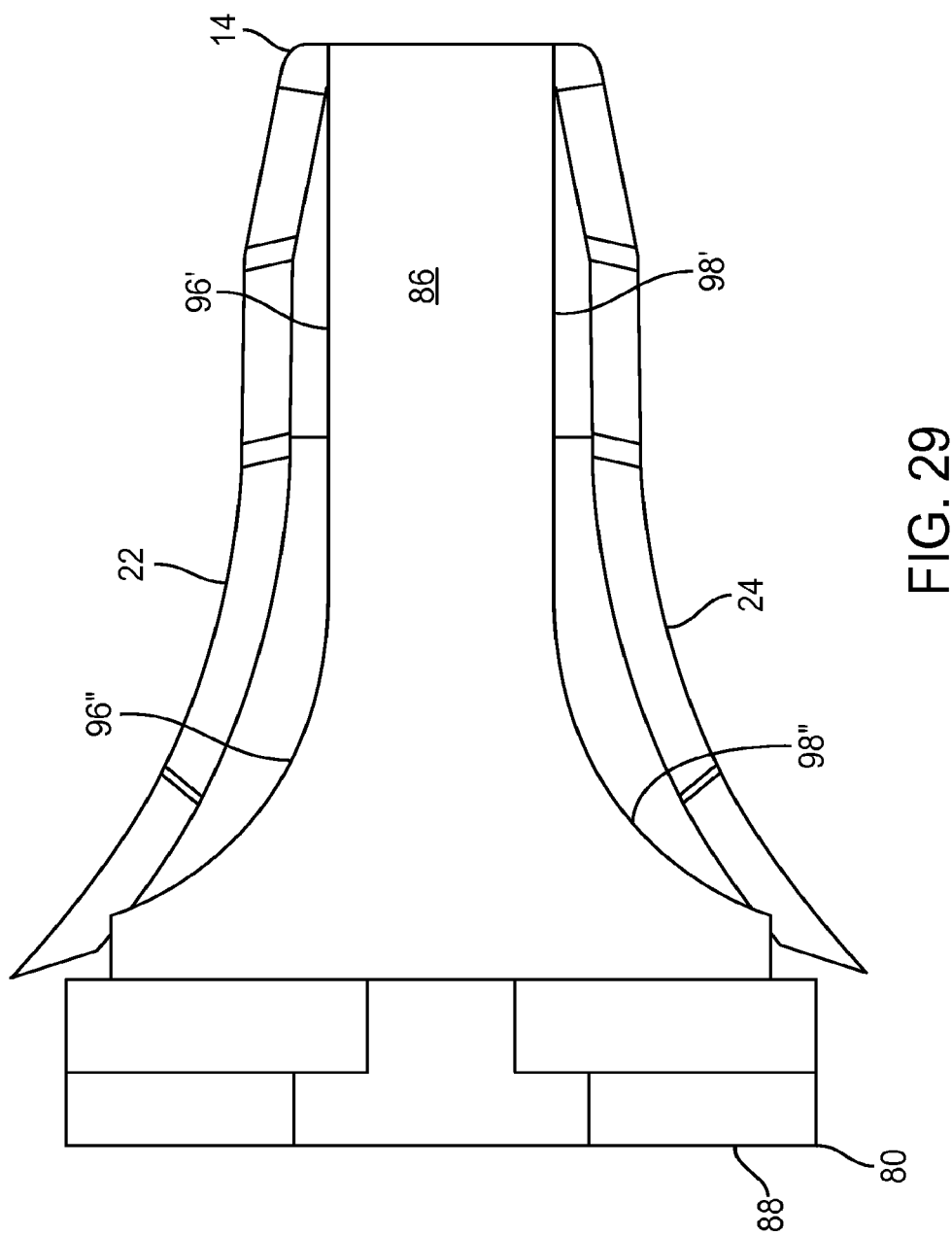
FIG. 29 is a lateral side elevation of the interaction of the plate and ramp when the plate is in the non-deployed state of FIG. 26.
Figure 30:
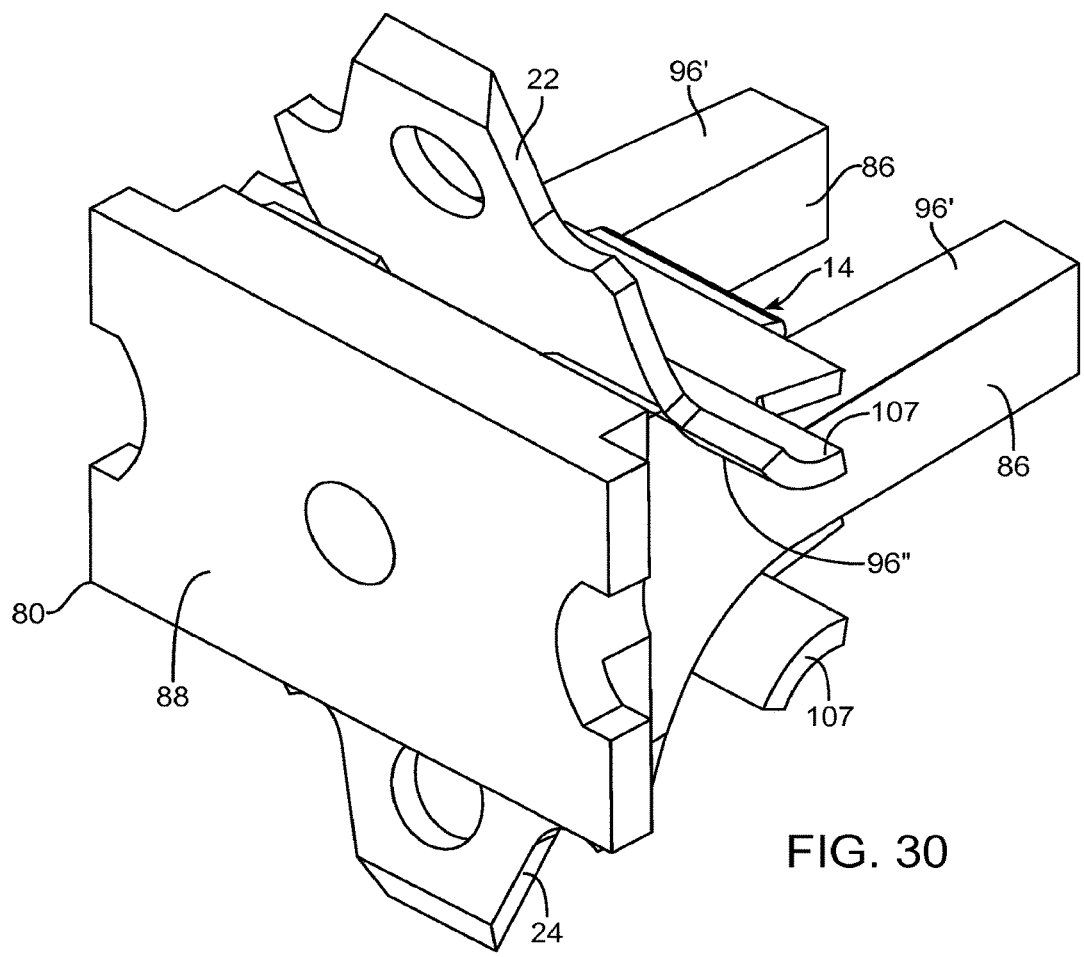
FIG. 30 is a proximal isometric view of the interaction of the plate and ramp when the plate is in the deployed state of FIG. 27.
Figure 31:
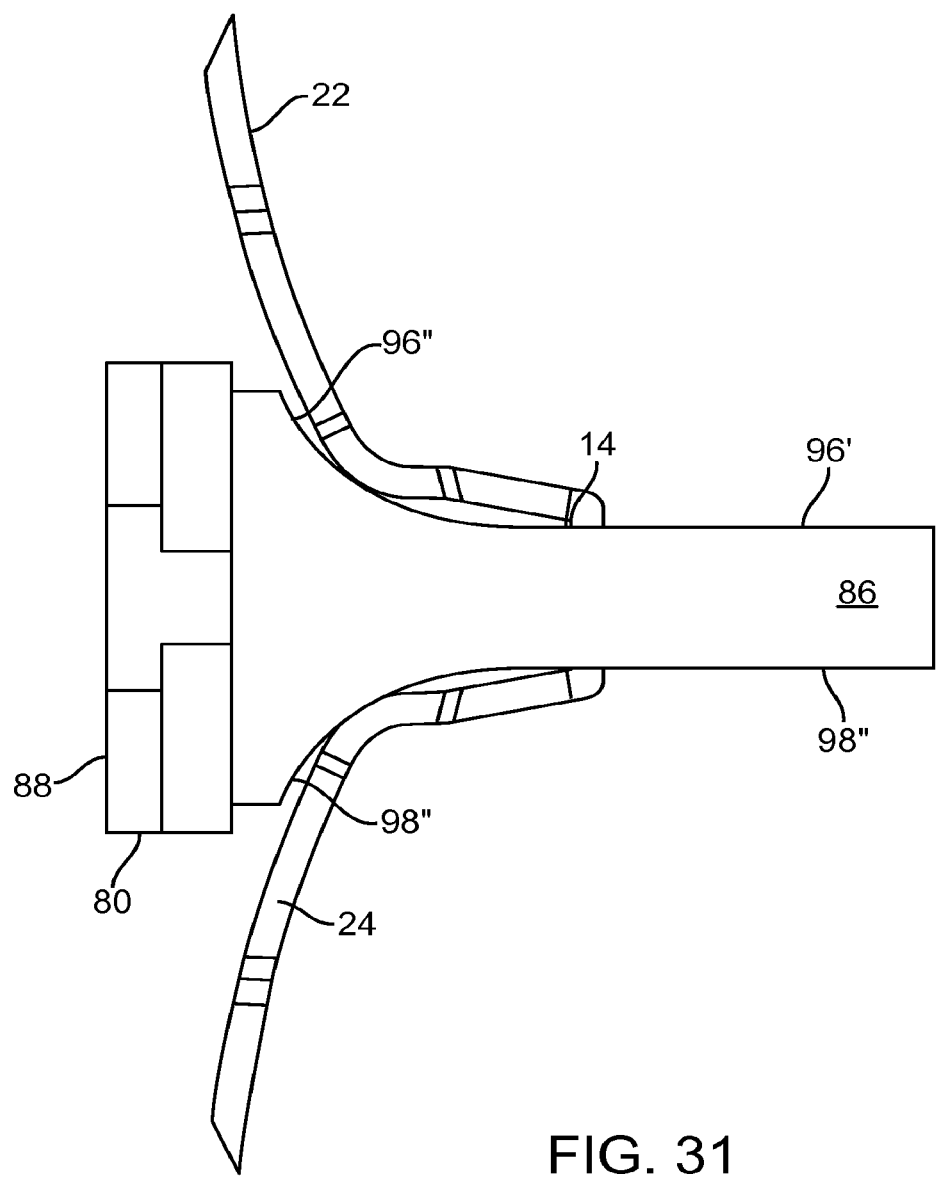
FIG. 31 is a lateral side elevation of the interaction of the plate and ramp when the plate is in the deployed state of FIG. 27.

The deployment of the fixation plate 14 is illustrated in FIGS. 28-31, wherein FIGS. 28-29 are, respectively, a proximal isometric view and a lateral side elevation of the interaction of the plate 14 and ramp 80 when the plate 14 is in the non-deployed state of FIG. 26, and FIGS. 30-31 are, respectively, a proximal isometric view and a lateral side elevation of the interaction of the plate 14 and ramp 80 when the plate is in the deployed state of FIG. 27. As indicated in FIGS. 28-31, proximal displacement of the plate 14 causes the inner surfaces of the blades 22, 24 to abut against and ride along the ramp surfaces 96, 98. Accordingly, the sloped regions 96", 98" drive the blades 22, 24 increasingly outwardly as the drive nut 100, and as a result, the plate 14 displaces increasingly proximal until the blade 14 reaches the deployed state illustrated in FIGS. 24-25, 27, and 30-31.

In one embodiment, the blades 22, 24 may be pre-curved to help them to deploy in a curved path into the vertebral bodies. Also, the plate 14 may change shape during deployment, guided by the ramp surfaces 96, 98 of the ramp 80, which is part of the implanter 18 of the implant tool set 10. The holes 28 may include physical features to prevent backout of the bond screws 16 received therein.

The extreme free ends of the blades 22, 24 that terminate in the sharp, rigid edges 106 may have the tri-tip configuration depicted in FIGS. 22-25, where the tri-tip configuration includes a central, flat blade section at a most proximal end of the plate 14 that is positioned between a pair of recessed outer tips. The tri-tip configuration may also include semi-circular blade section positioned between each of the recessed outer tips and the central flat blade section as well as a pair of side edges that extend from the respective sides of the extreme lateral wings 107 to the recessed outer tips. In one embodiment, all portions of the tri-tip configuration may be sharp, rigid edges 106 being meant to improve their ability to cut into cortical bone. In one embodiment, the blades 22, 24 and the intermediate portion 102 may be a contiguous titanium sheet bent into shape. In one embodiment, the drive nut 100 is fabricated separated and welded into the contiguous bent plate 14. The fixation plate 14 is configured to span two vertebral sections upon reaching the deployed state.

Figure 32:
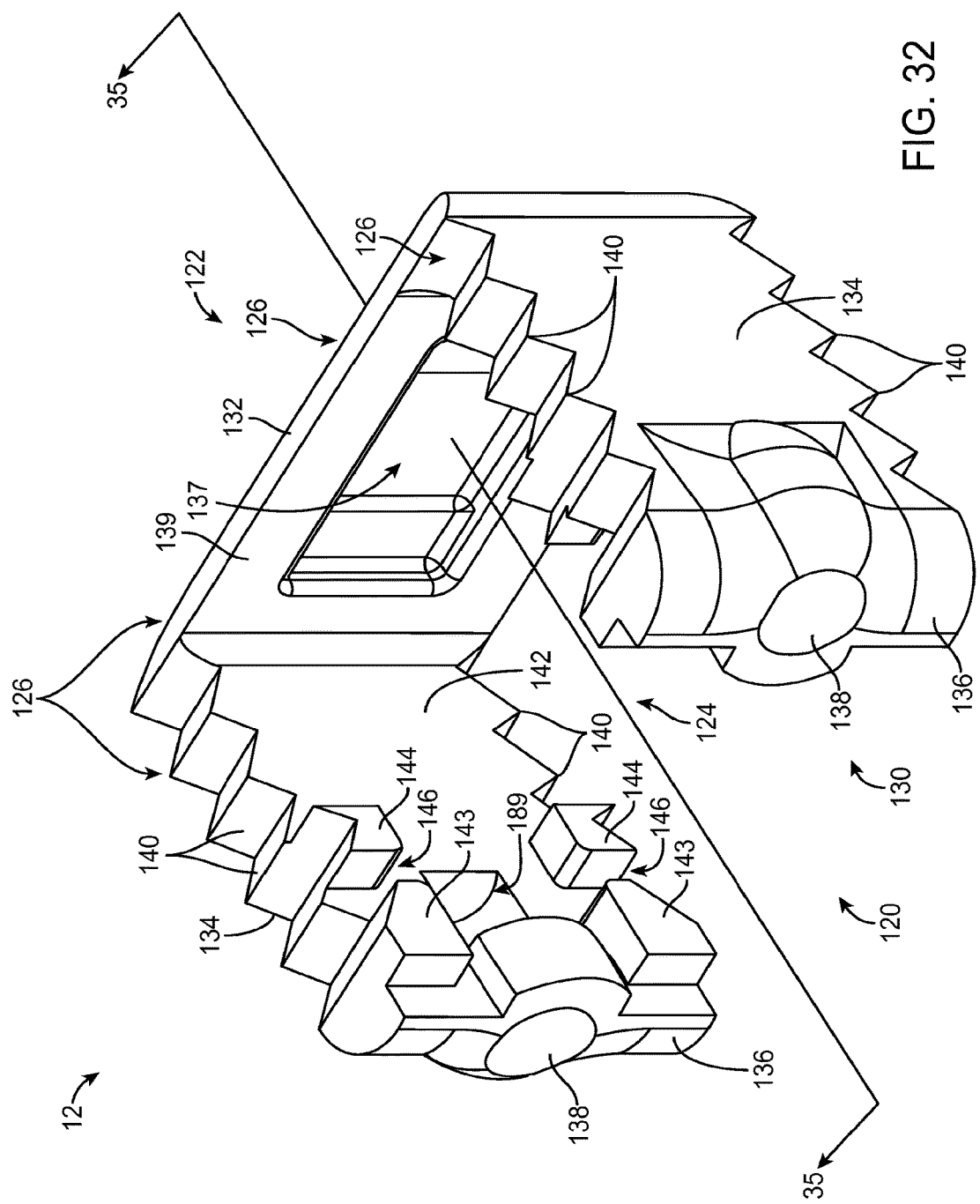
FIG. 32 is a proximal isometric view of an interbody fusion cage, according to one embodiment.
Figure 33:
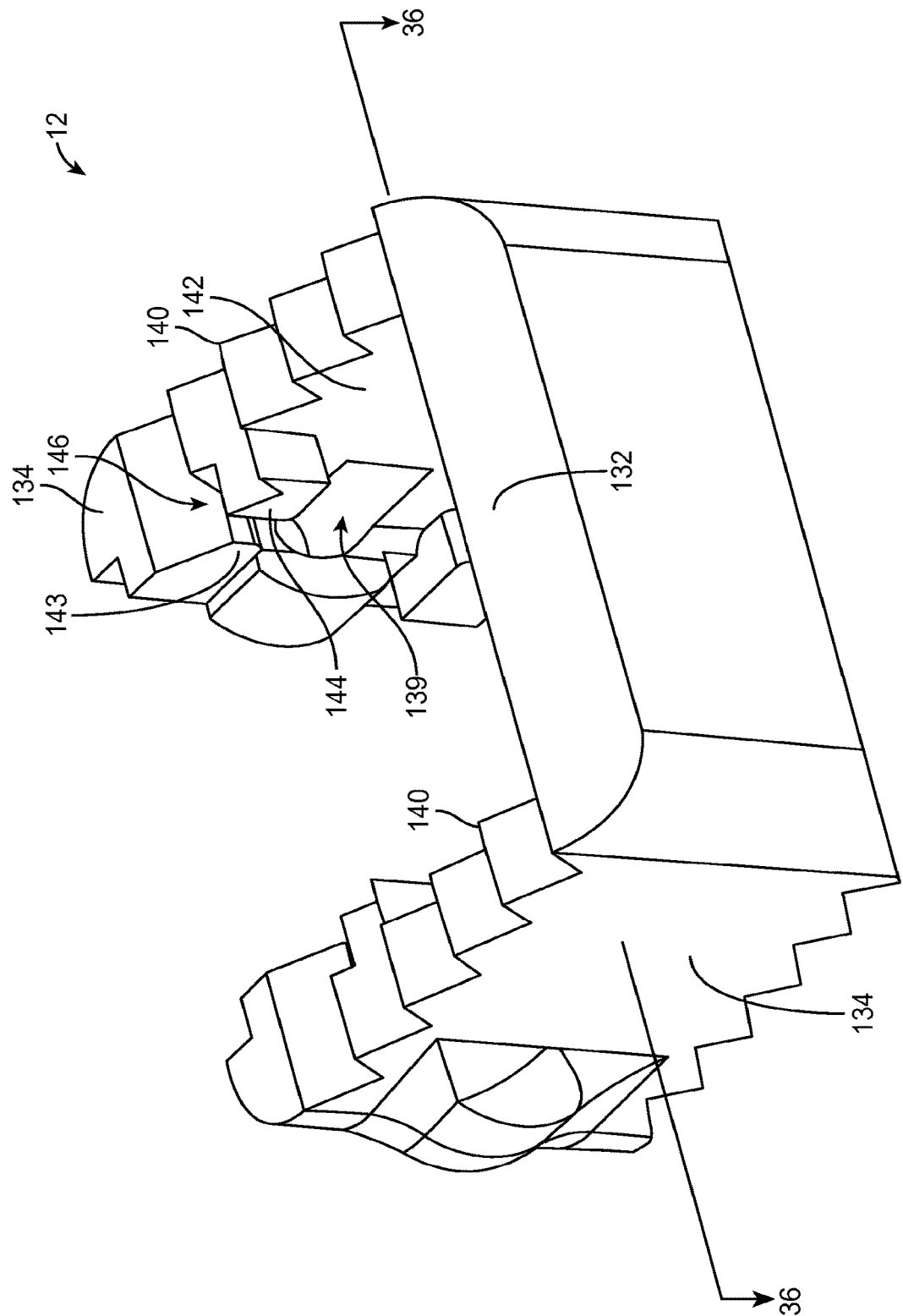
FIG. 33 is a distal isometric view of the interbody fusion cage.

Turning now to another component of the spinal implant 8, reference is now made to FIGS. 32 and 33, which are, respectively, a proximal isometric view and a distal isometric view of the interbody fusion cage 12. As shown in FIGS. 32 and 33, the cage 12 includes a proximal end 120, a distal end 122, an interior open volume 124, and an outer wall 126 that defines outer peripheral boundaries of the cage 12 and the interior open volume 124 and separate the volume 124 from the outer boundaries. The wall 126 is incomplete or open on the proximal end 120 of the cage 12 such that the cage 12 has a C-cross section or shape as can be best understood from FIG. 34, which is a superior plan view of the cage 12. Thus, the proximal end 120 of the cage 12 has an opening 130 that allows the plate 14 and ramp 80 to be inserted into the open volume 124 of the cage 12.

Figure 34:
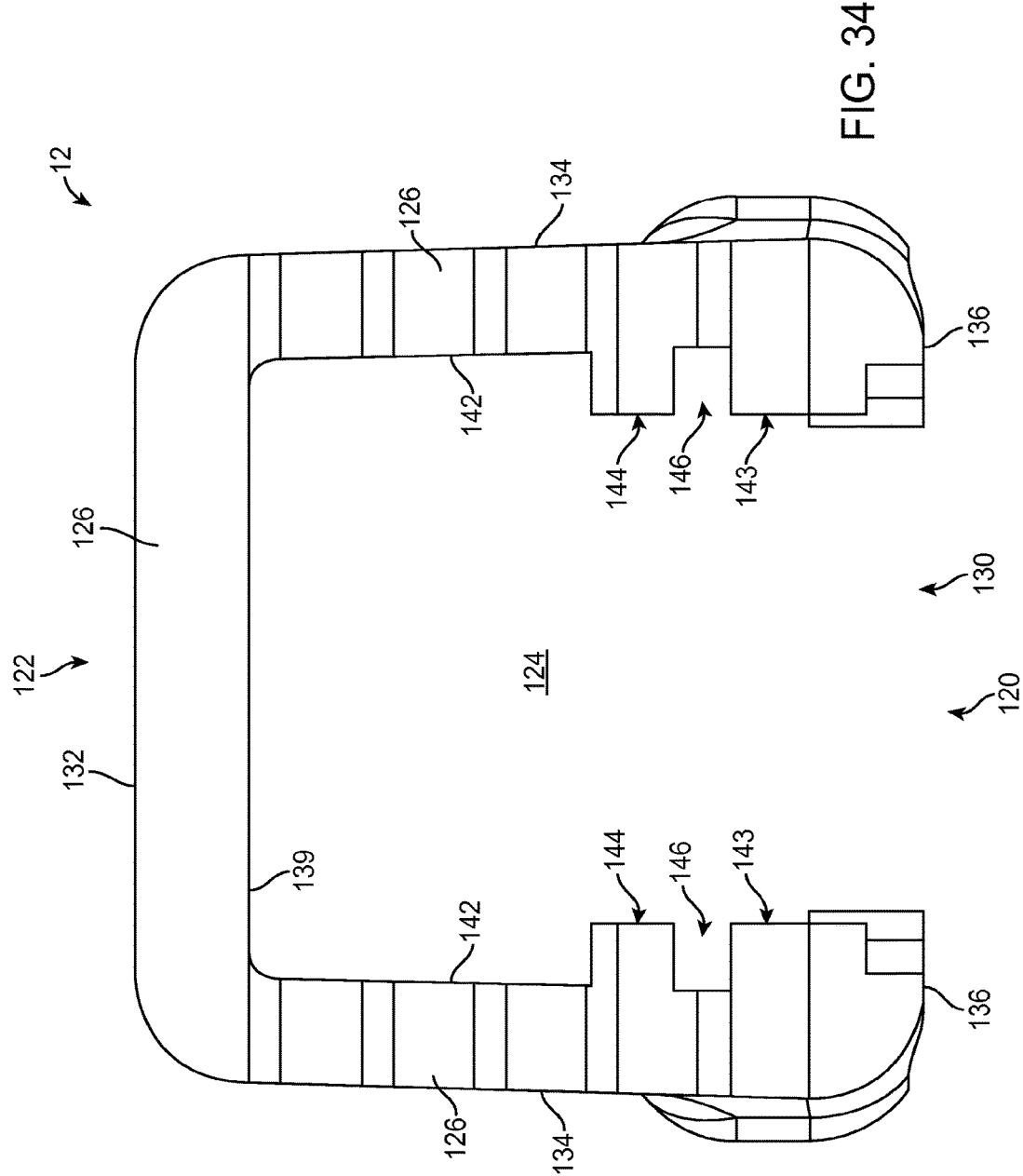
FIG. 34 is a superior plan view of the cage, the inferior plan view being identical to the superior plan view.

As indicated in FIGS. 32-34, the wall 126 includes a distal enclosed section 132 and a pair of side walls 134. A proximal termination 136 of each side wall 134 includes a pin receiving hole 138 that projects distally into the interior of each side wall 134 from the proximal termination 136, as best understood from FIGS. 36 and 37, which are, respectively, lateral cross sections of the cage 12 in plan view and distal isometric view as taken along section line 36-36 in FIG. 33. Each hole 138 daylights in an interior surface 142 of the respective sidewall 134 to define a pocket or recess 189 in the sidewall 134.

Figure 35:
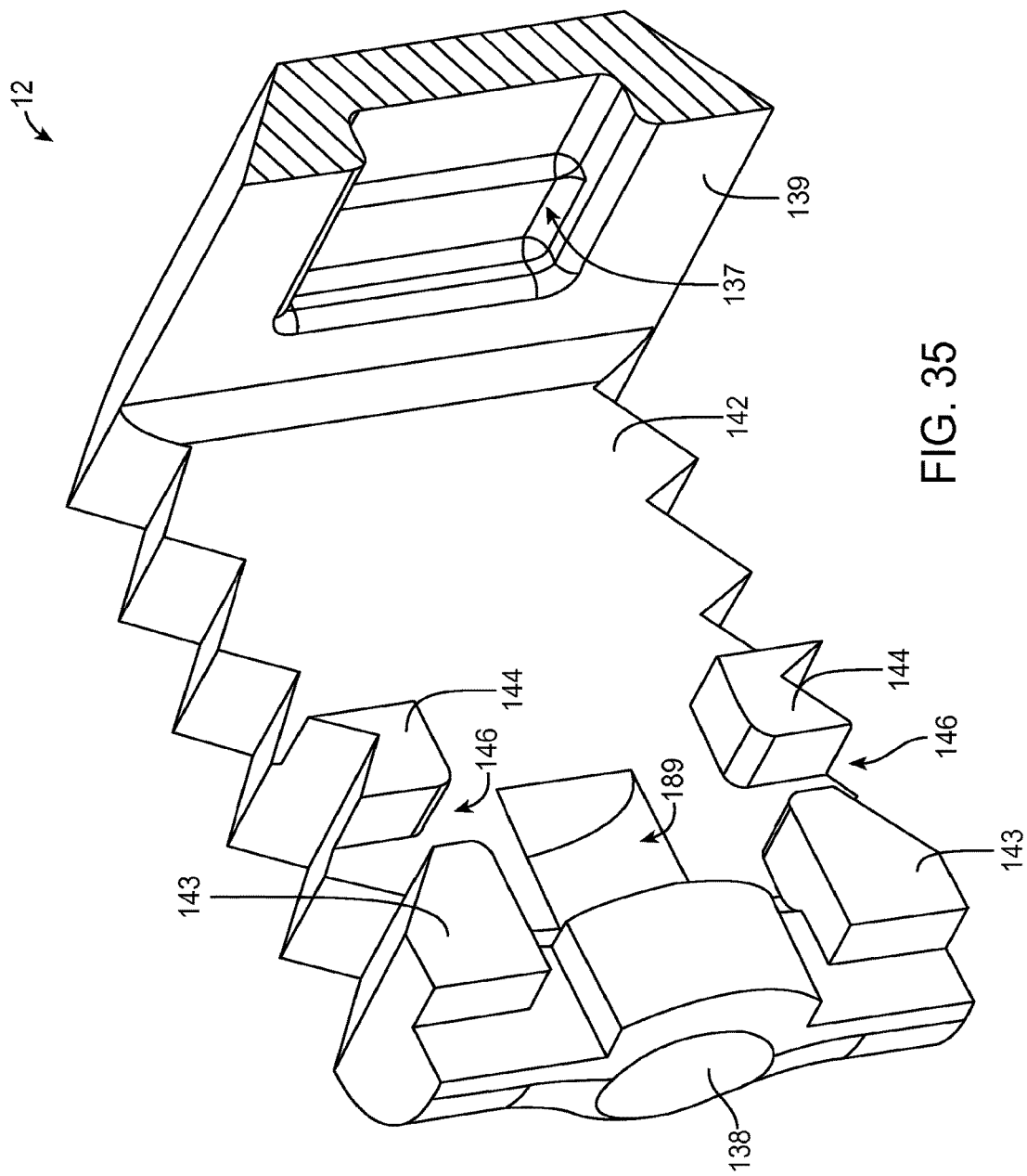
FIG. 35 is a longitudinal cross section of the cage in a proximal isometric view, as taken along section line 35-35 in FIG. 32.
Figure 36:
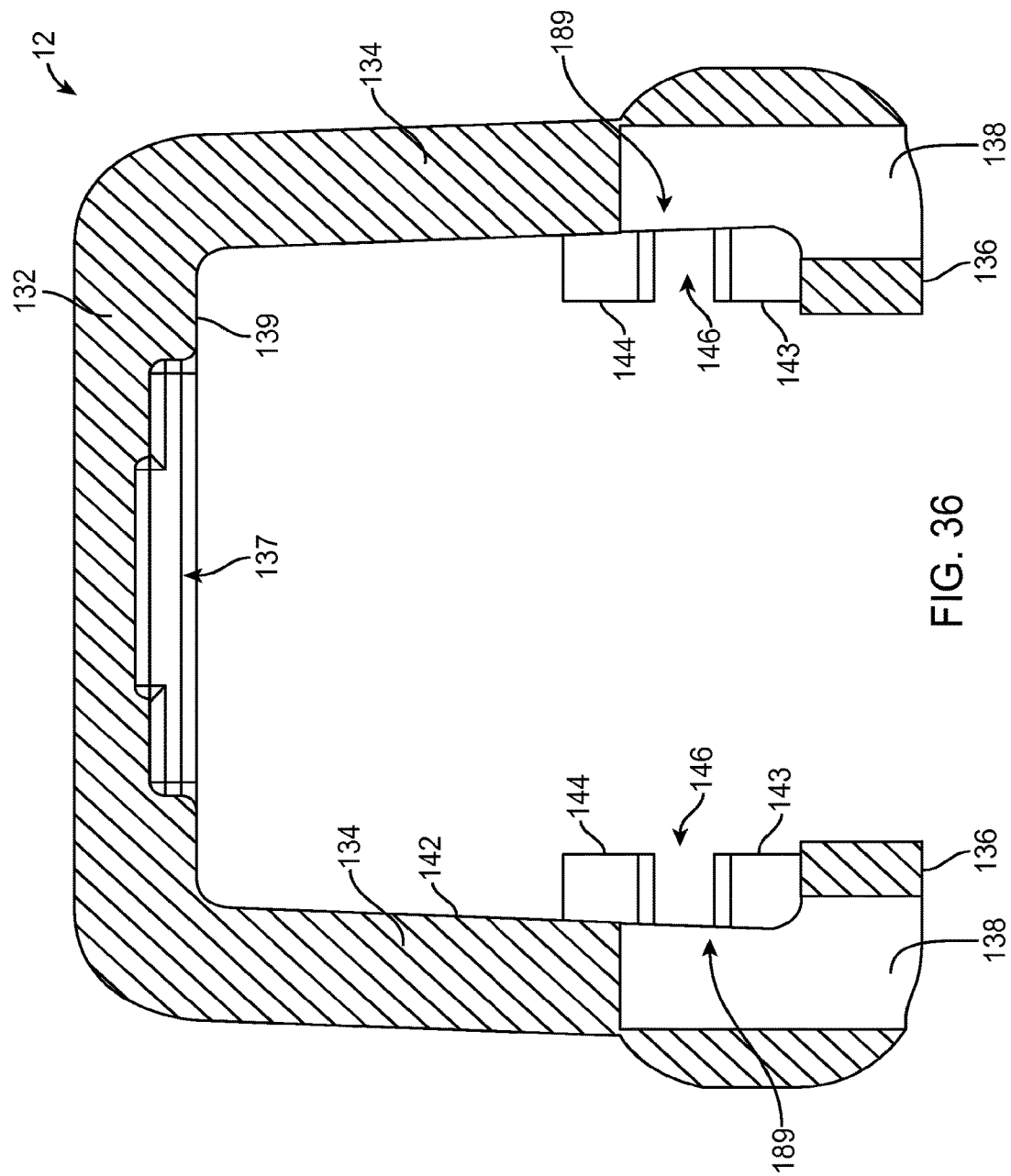
FIG. 36 is a lateral cross section of the cage in plan view, as taken along section line 36-36 in FIG. 33.
Figure 37:
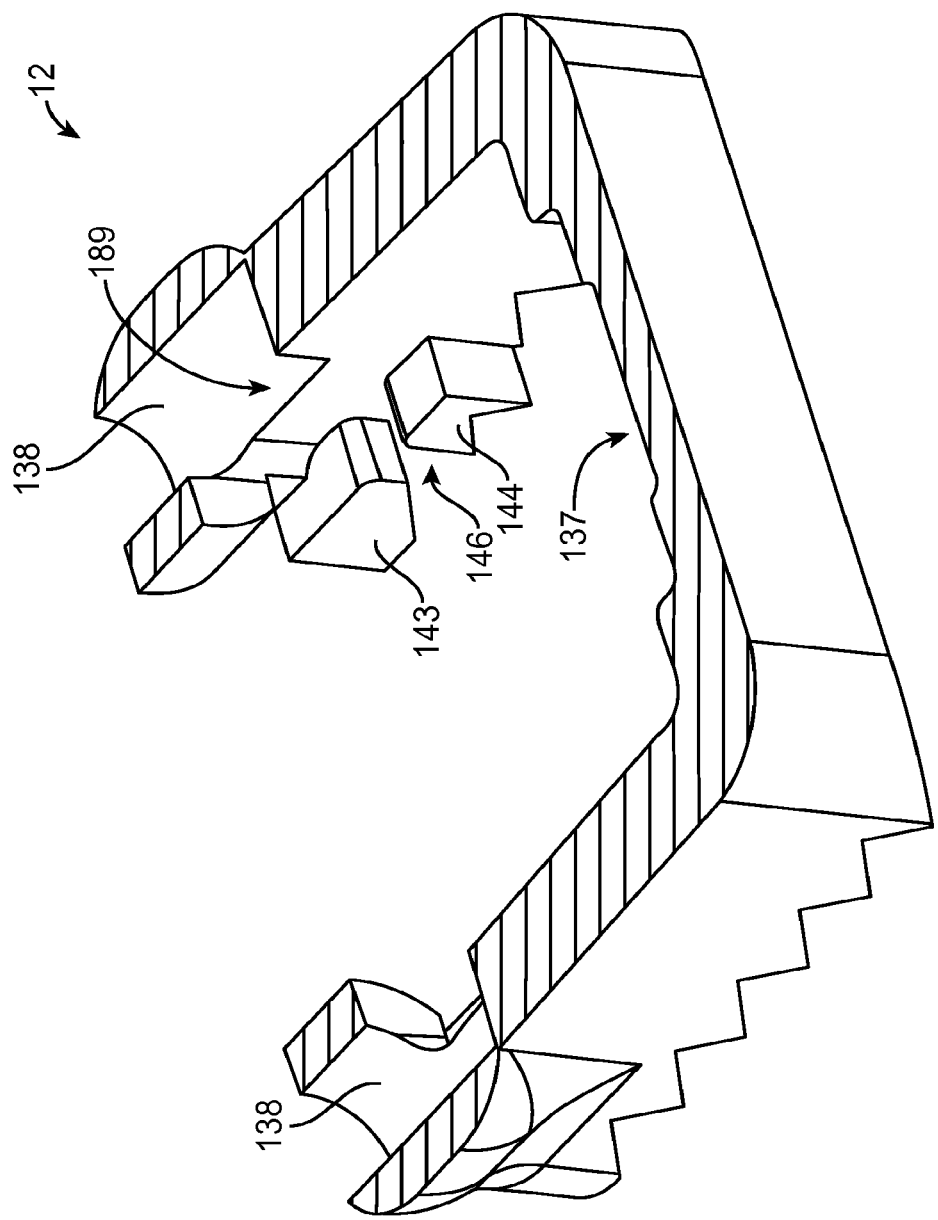
FIG. 37 is the same lateral cross section of the cage as in FIG. 36, except shown in distal isometric view.
Figure 39:
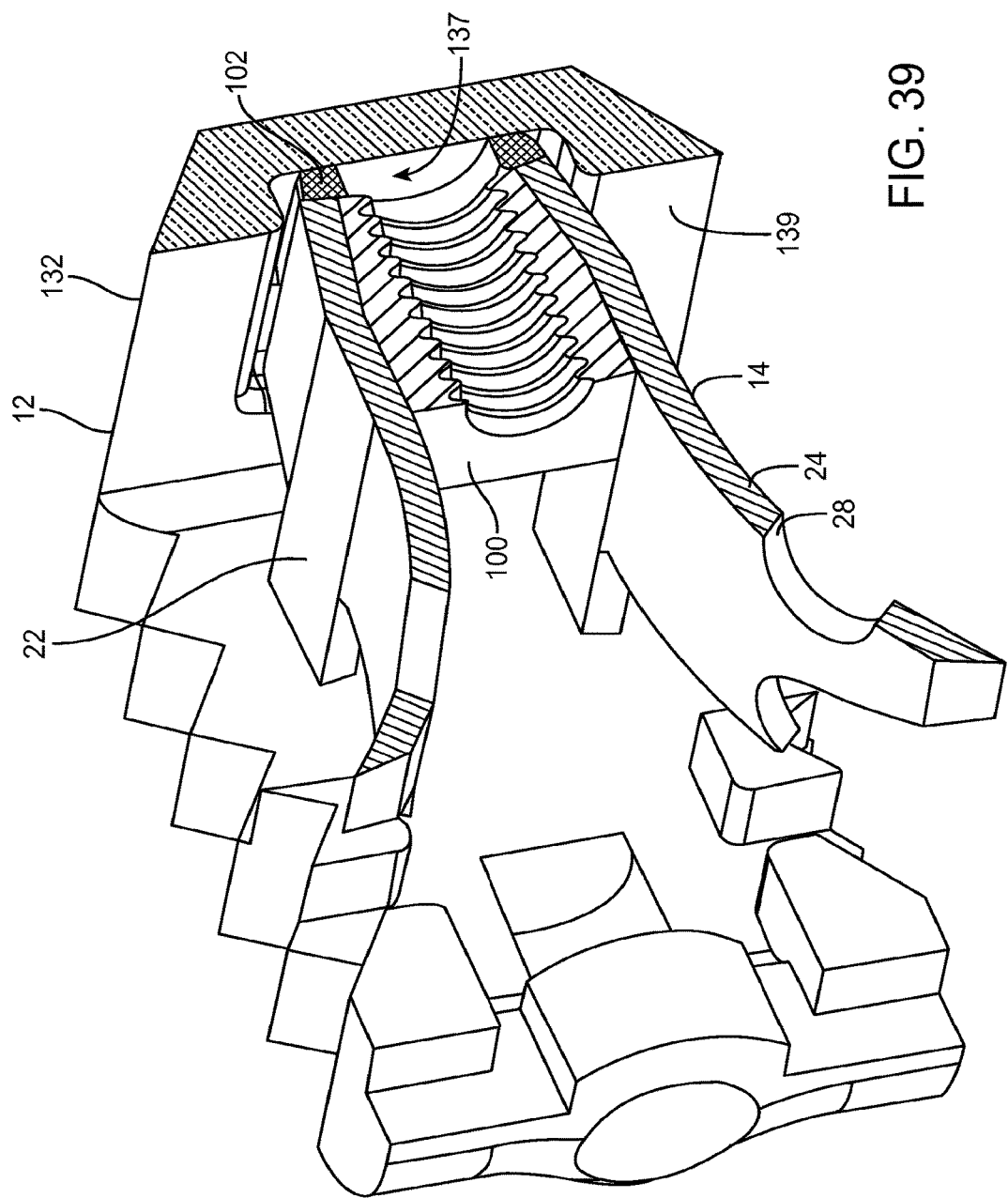
FIG. 39 is generally the same cross section view as illustrated in FIG. 35, except showing the plate and drive nut in the non-deployed state within the cage.
Figure 40:
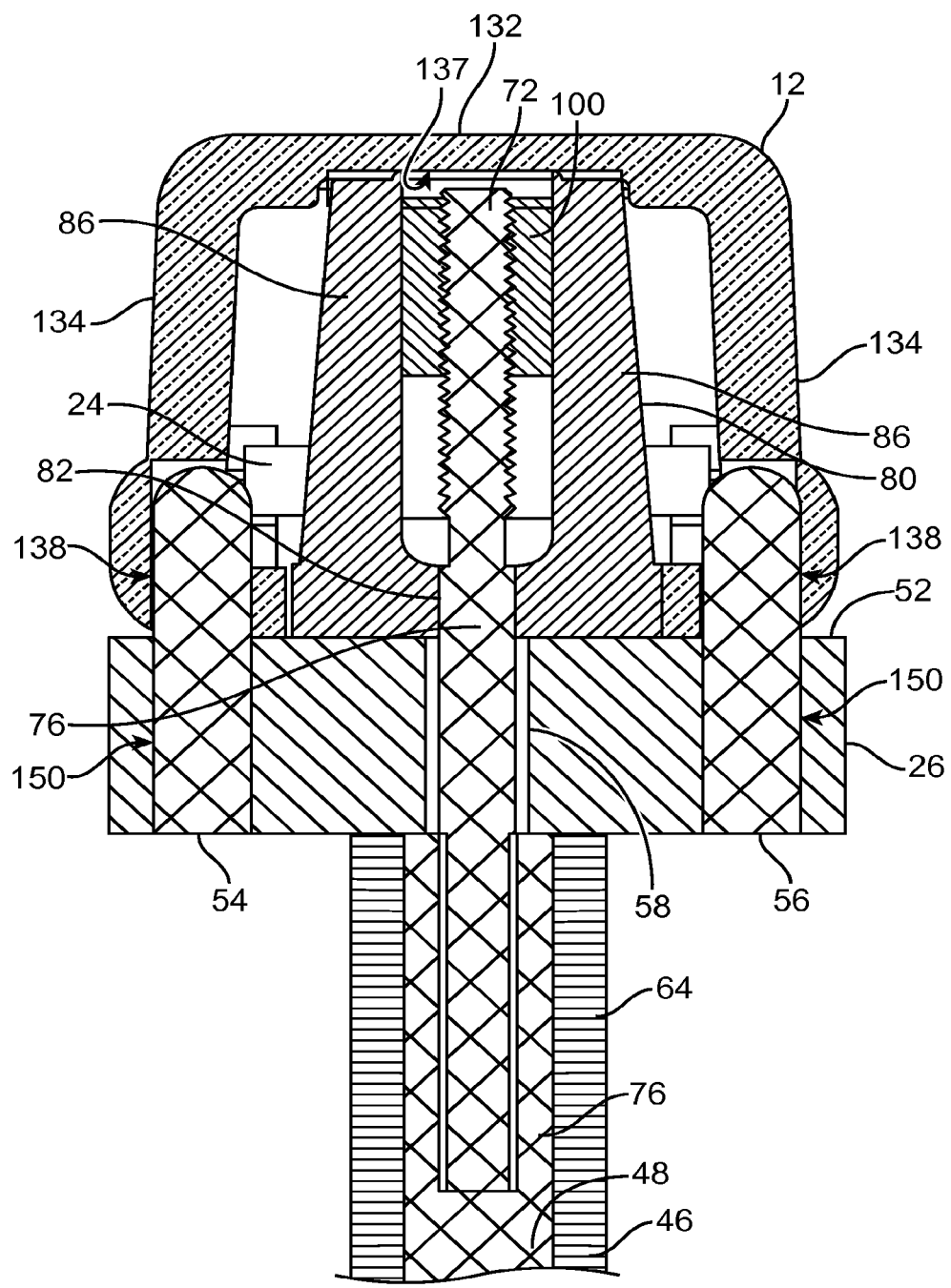
FIG. 40 is an enlarged plan view cross section of the entire distal region of the system, as taken along section line 40-40 in FIG. 1.

As depicted in FIGS. 32, 36, and 37 and further illustrated in FIG. 35, which is a longitudinal cross section of the cage 12 in a proximal isometric view as taken along section line 35-35 in FIG. 32, the distal wall section 132 includes a rectangular recess 137 defined in an inner surface 139 of the distal wall section 132. As can be understood from FIG. 39, which is generally the same cross section view as illustrated in FIG. 35, except showing the plate 14 and drive nut 100 in the non-deployed state within the cage 12, the recess 137 receives the extreme distal ends of the plate 14 and the drive nut 100. Also, as can be understood from FIG. 40, which is an enlarged plan view cross section of the entire distal region of the system 6 as taken along section line 40-40 in FIG. 1, the recess 137 can be seen to receive the extreme distal ends of the threaded distal termination 72, the ramp arms 86 and the plate intermediate portion 102.

Figure 38:
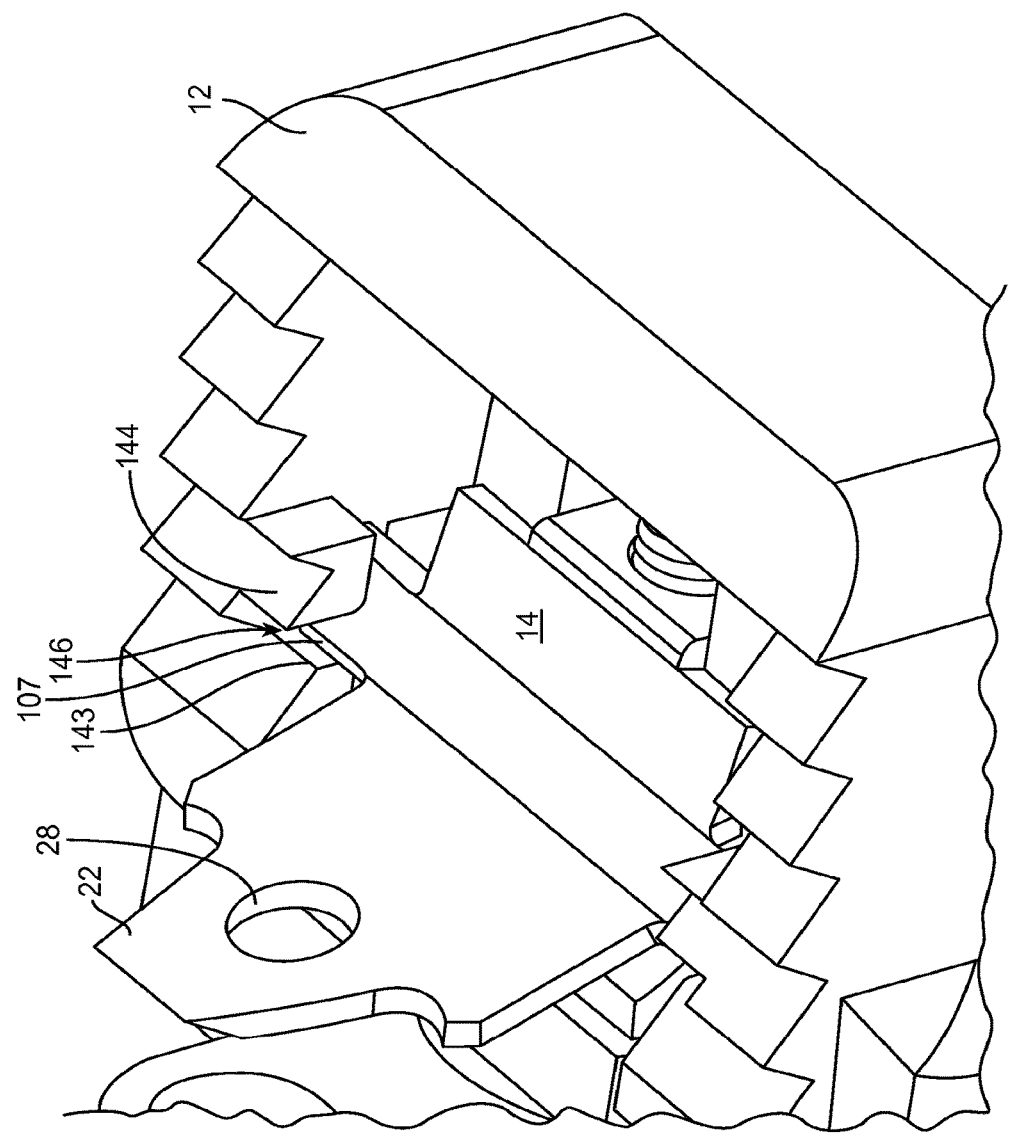
FIG. 38 is an enlarged distal isometric view of one of the extreme lateral wings of a plate blade being received in the space defined by the pair of inward projections of a side wall of the cage, according to one embodiment.

As shown in FIGS. 32-34, the superior and inferior surfaces of the side walls 134 include a series of saw teeth or peaks 140. Also, as indicated in FIGS. 32-37, the interior surfaces 142 of the side walls 134 include superior and inferior paired lock tabs in the form of inward projections 143, 144 that define a slot, notch, grove or other type of space 146 through which the extreme lateral wings 107 extend when the plate 14 is in the deployed state. This locking arrangement, as best depicted in FIG. 38, which is an enlarged distal isometric view of one of the extreme lateral wings 107 being received in the space 146 defined by the pair of inward projects 143, 144, locks the plate 14 and cage 12 together to prevent anterior-posterior and lateral displacement of the cage 12 and fixation plate 14 relative to each other when the plate 14 is in the deployed state.

Figure 9:
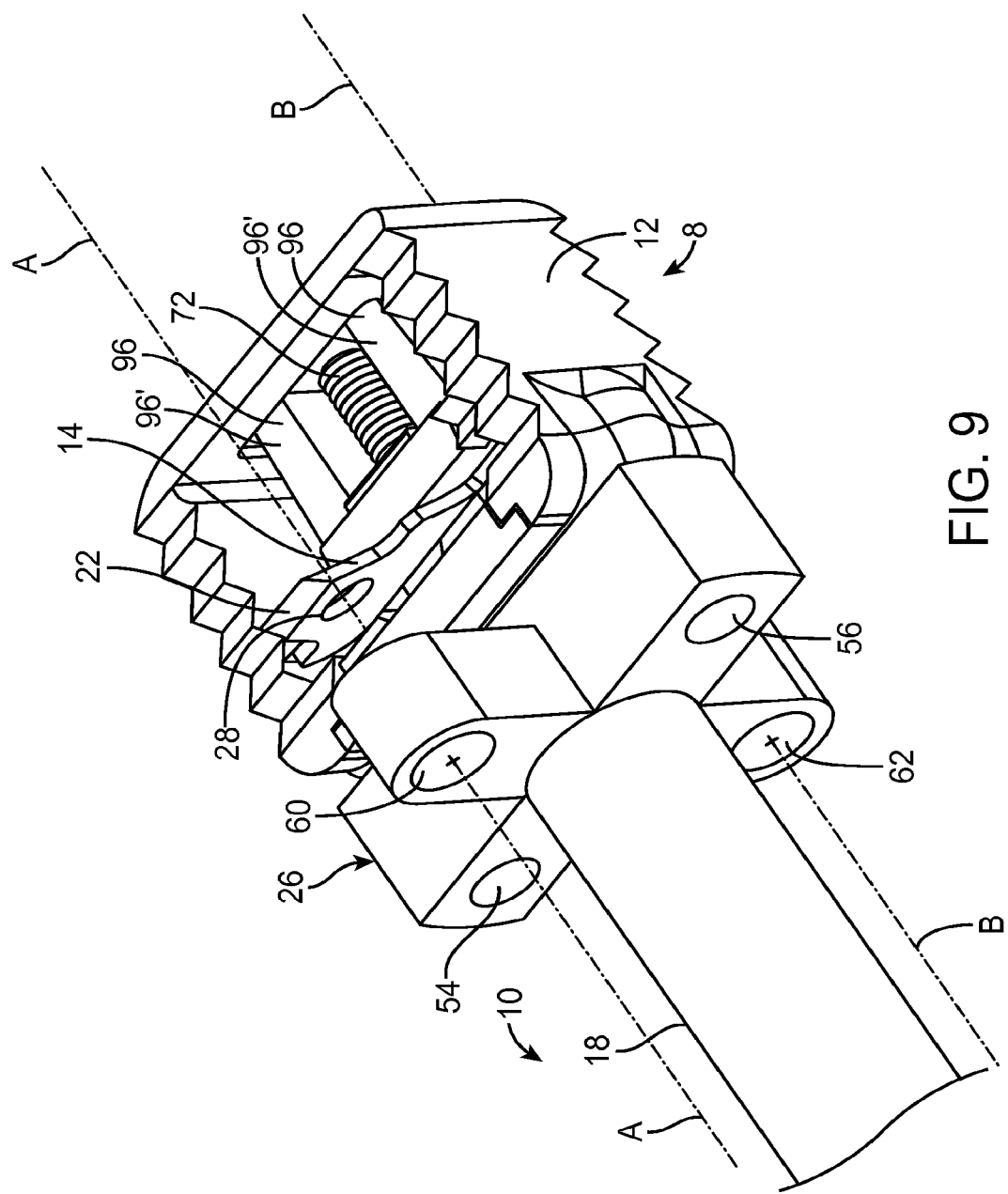
FIG. 9 illustrates the same aspects as FIG. 8, except in an enlarged proximal isometric view.

In one embodiment, as can be understood from FIGS. 9, 12 and 13, the projections 54, 56 extend through the distal end 26 of the implanter 18, in addition to projecting into the pin receiving holes 138 of the cage 12. As more clearly depicted in FIG. 40, projections 54, 56 may simply be received in the corresponding pin receiving holes 138 in an interference or friction fit arrangement. However, in other embodiments, the projections 54, 56 may be in the form of threaded members 54, 56 that are rotated via a rotation force applied to their respective proximal ends to thread the threaded members 54, 56 into the pin receiving holes 138, which have complementary threaded arrangements. To facilitate the application of a rotational force to the threaded members 54, 56 and their rotation about their respective longitudinal axes within the distal end 26 of the implanter 18, only the portions of the members 54, 56 distal of the implanter distal end 26 would be threaded, the portions of the members 54, 56 within the distal end 26 having smooth bearing surfaces in smooth bearing surfaced holes 150, the proximal end of each member 54, 56 having a knob for grasping or a feature that facilitates mechanical engagement via a tool such as, e.g., a screw driver head, Allen wrench or other type of wrench. After full deployment of the implant 8, the members 54, 56 could be reverse rotated to disengage the members 54, 56 from the cage holes 138 to release the implanter distal end 26 from the cage 12.

Figure 41:
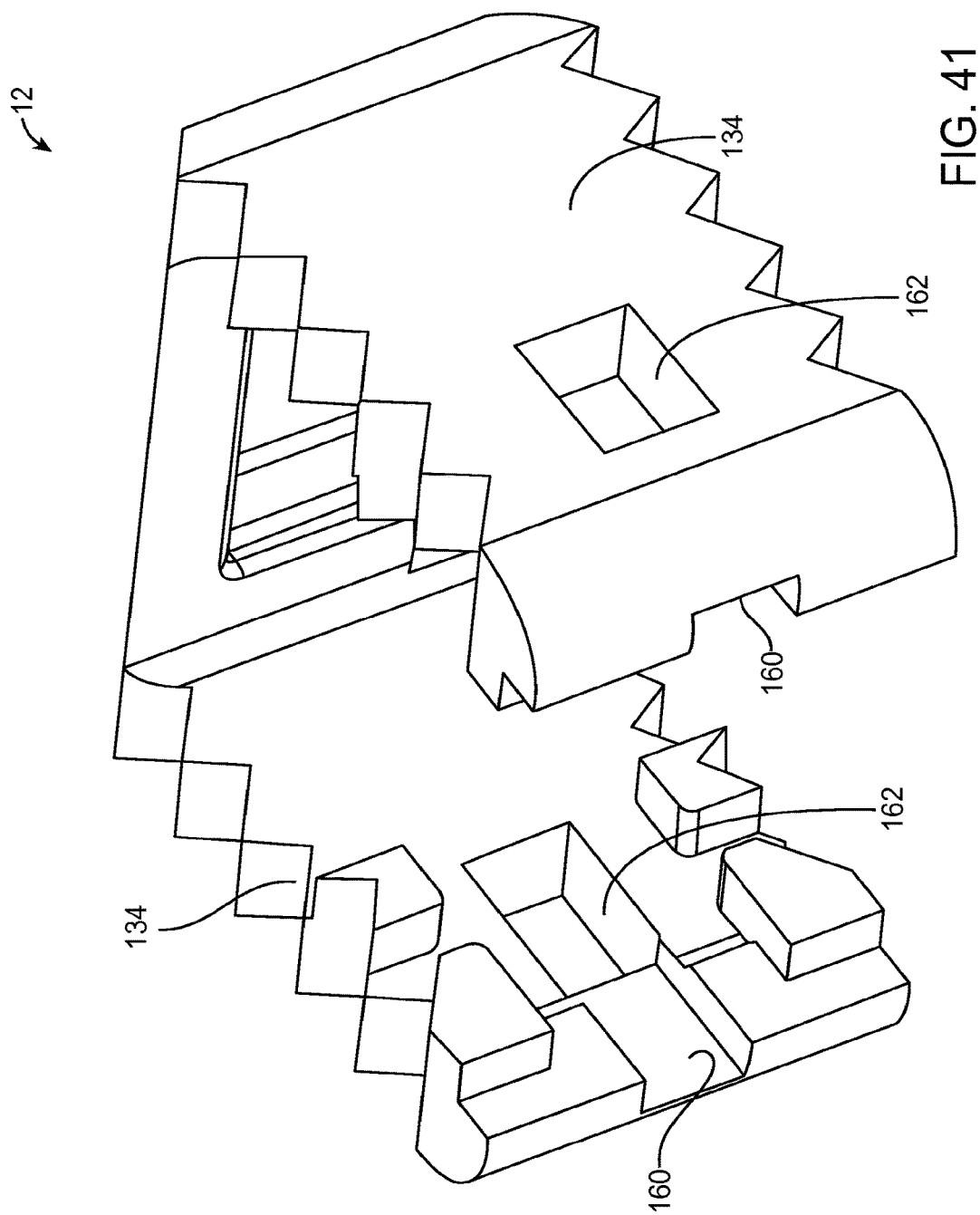
FIG. 41 is a proximal isometric view of an interbody fusion cage, according to an alternative embodiment.
Figure 42:
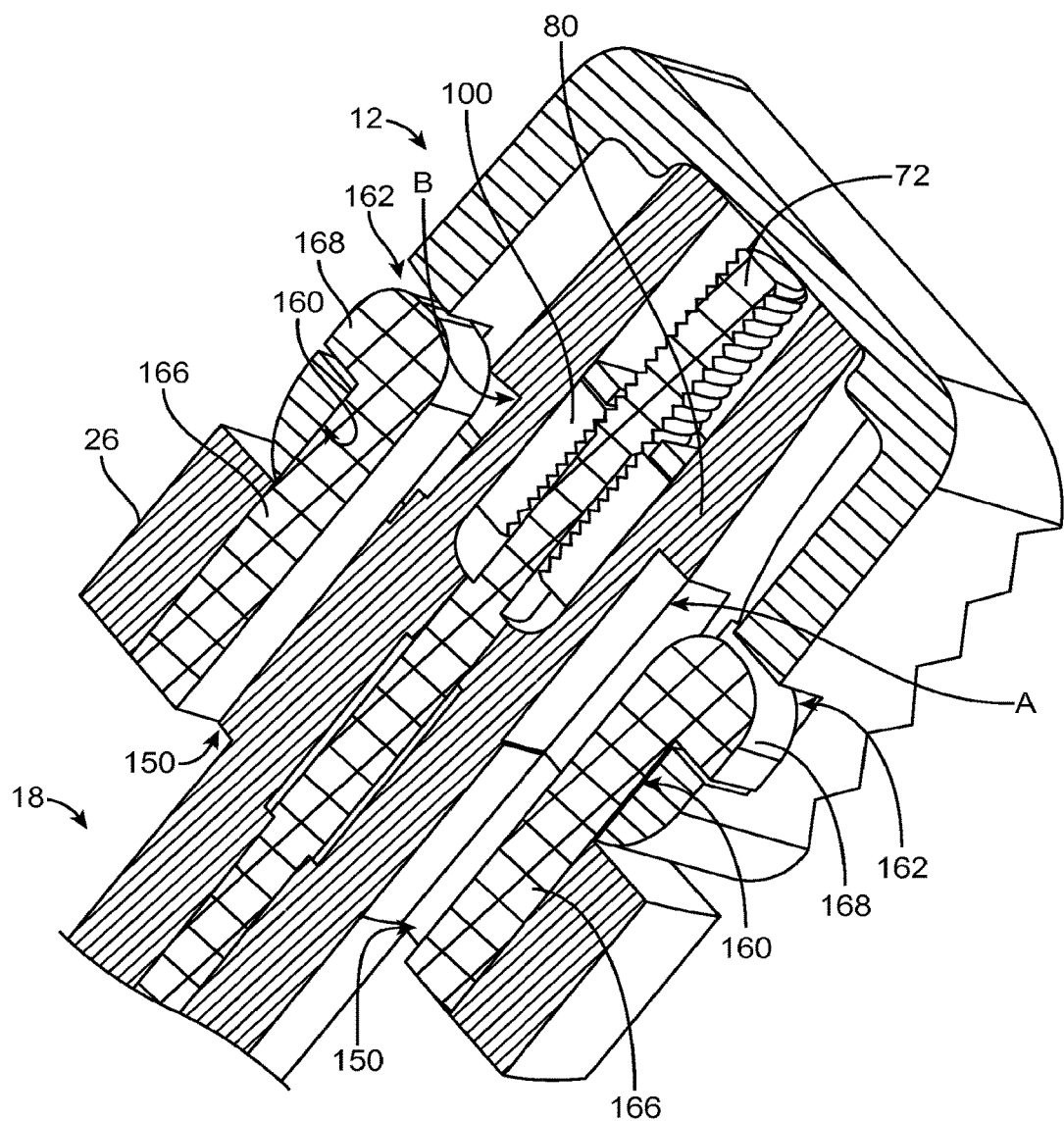
FIG. 42 is a proximal cross section of the distal region of the system, as taken along section line 42-42 in FIG. 41.

In another embodiment, as depicted in FIGS. 41 and 42, which are, respectively, a proximal isometric view of another embodiment of the cage 12 and a proximal cross section of the distal region of the system 6 as taken along section line 42-42 in FIG. 41, the pin retaining arrangement discussed above with respect to member 54, 56 being received in cage holes 138 may be replaced with a hook/window engagement arrangement. For example, as shown in FIG. 41, the cage may have slots 160 defined in an interior surface 142 of the sidewalls 134, and these slots 160 lead to windows 162 extending completely through the sidewalls 134. As indicated in FIG. 42, hook-latches 166 extend distally from the implanter distal end 26 and distally terminate in hook features 168. When the implanter distal end 26 is coupled to the cage proximal end, the hook-latches 166 distally displace along the slots 160 and then moved outward until the hook features 168 are received in the windows 162. The process is reversed to achieve removal of the hook-latches 166. The hook-latches 166 may have a variety of mechanisms for moving the hook-latches inward and outward. For example, such as scissor-like mechanisms, wedge type mechanisms, etc.

For example, wedge-type components can be advanced axially next to the latch 166 to push them outward. The latches in this case can be spring-loaded to bias them toward the "retracted" position, so that when the wedges are removed the latches 166 will go back to the retracted position for cage release.

As shown in FIG. 42, the openings 150 in the implanter distal end 26 are sufficiently large to allow the passage of the hook features 168 there through and their movement inward and outward to engage or disengage from the windows 162. Similarly, the ramp 80 is notched out on its proximal lateral sides to provide sufficient space for the hook features 168 to move inward and outward, as called out in FIG. 42 by arrows A and B.

In one embodiment, the interbody fusion cage 12 is formed of biocompatible materials, such as, e.g., PEEK, titanium, stainless steel, etc. In one embodiment, the proximal side of the cage 12 is completely open, resulting in a horseshoe shape. In other embodiments, the cage 12 is closed such that it is contiguous around its perimeter, although a large proximal opening may be defined in the perimeter to facilitate loading of the plate 14 and bone growth promoting material into the cage 12. In one embodiment, the cage 12 has a lateral width of approximately 17 mm, a distal-proximal depth of approximately 14 mm depth, and a superior-inferior height of approximately 8 mm. In other embodiments, the dimensions of the cage 12 will be greater or smaller. For example, the cage widths may be 12 mm, 14 mm, 17 mm, etc., the cage depths may be 12 mm, 14 mm or etc., and the cage heights may be 5 mm, 6 mm, 7 mm, 8 mm, 9 mm, 10 mm, 11 mm, or etc. The cage 12 may have 5-7 degrees of lordotic angle and/or an anatomic shape to fit the superior vertebra endplate. Also, in some embodiments, the cage 12 may have configuration with parallel lateral sides. The cage 12 and the corresponding aspects of the implanter 18 may be configured to have features that interact with each other to enhance the attachment of the cage 12 to the distal end 26 of the implanter 18.

In one embodiment, the fixation plate 14 and the cage 12 are separate elements that are fitted or otherwise applied together in a prep or operating room in a surgical facility or otherwise independently deployable from each other. In other embodiments, the fixation plate 14 and cage 12 are a signal integral unit from the manufacturer so no assembly is required in the field. In other words, the cage 12 and anterior plate 14 may be supplied separately, but pre-assembled prior to insertion. It is also possible for the cage 12 and plate 14 to be deployed separately if desired. The interior void region of the cage 12 in which the plate 14 is located is additionally adapted for the receipt of bone growth promoting material and forms a closed graft space.

The plate 14 includes a superior blade 22 and an inferior blade 24. The plate 14 is designed to be located within the boundaries of the cage 12 and delivered into the disc space with the cage 12 via the implanter 18. When located both within the boundaries of the cage 12 and the confines of the disc space, the plate 14 is deployed via action of the implanter 18 to penetrate from the disc space into the superior and inferior vertebra, thereby spanning the two vertebral sections bordering the disc space in which the cage 12 is implanted and preventing the cage 12 from displacing anterior-posterior or medial-lateral. When the plate 14 is deployed to extend into the superior and inferior vertebra, the superior blade 22 and the inferior blade 24 respectively extend superior and inferior from the boundaries of the cage 12 to respectively penetrate the superior and inferior vertebra.

In one embodiment, the system 6 may further include a trail/sizer tool including a set of trial/sizer instruments. Such instruments may incorporate a pre-scoring blade to break the vertebral endplate prior to insertion of the spinal implant 8 into the disc space.

d. Spinal Fusion Methodology Employing Spinal Fusion System

To begin a discussion of the details of the methodology of employing the components of the spinal fusion system 6, reference is made to FIGS. 43-46, which are, respectively, a proximal isometric view of the system 6 adjacent a superior vertebra 200 and an inferior vertebra 202, a vertical cross section through the two vertebra 200, 202 with the fixation plate 14 in the fully deploy state, a proximal isometric view of the bone screws 16 being implanted, and a proximal isometric view of the finished implantation of the implant 8 with the vertebra 200, 202 shown in phantom.

Initially, as discussed above with respect to FIGS. 28, 29 and others, the anterior fixation plate 14 is loaded onto the ramp 80 in a non-deployed state. The combined ramp 80 and plate 14 are then coupled to the implanter distal end 18 via the threaded distal termination 72 being threaded into the drive nut 100, as discussed above with respect to FIGS. 26 and 40, and further via the pins 54, 56 or latches 166 being received in the cage 12 as respectively depicted in FIGS. 40 and 42. The system 6 is now assembled as depicted in FIGS. 1 and 7.

Figure 7:
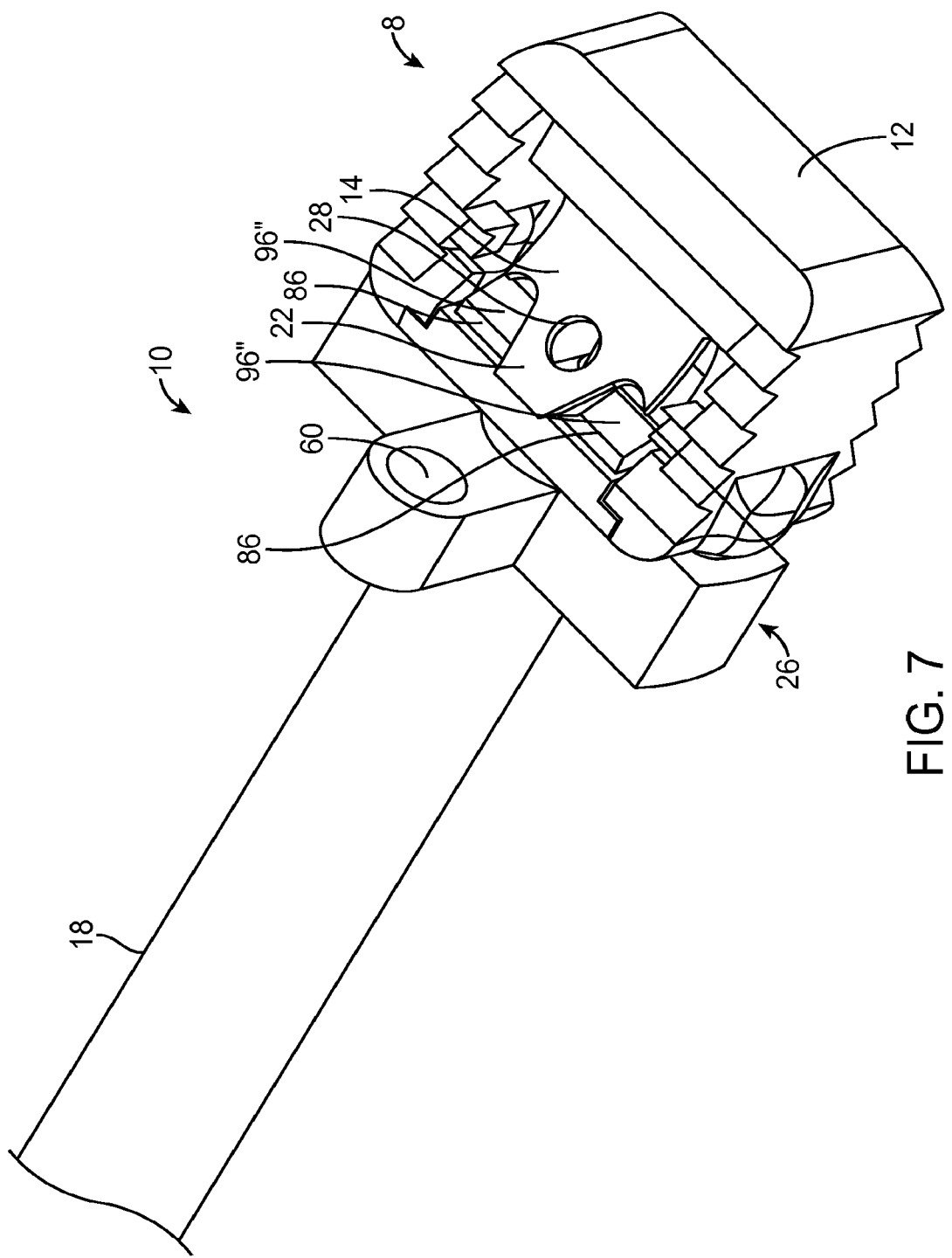
FIG. 7 is an enlarged distal isometric view of the distal end of the spinal fusion system of FIG. 1, showing the spinal implant supported on the distal end of the implanter, with the anterior fixation plate in a non-deployed state, such that the fixation plate is substantially, if not entirely, located within the confines of the exterior boundaries of the interbody fusion cage.
Figure 43:
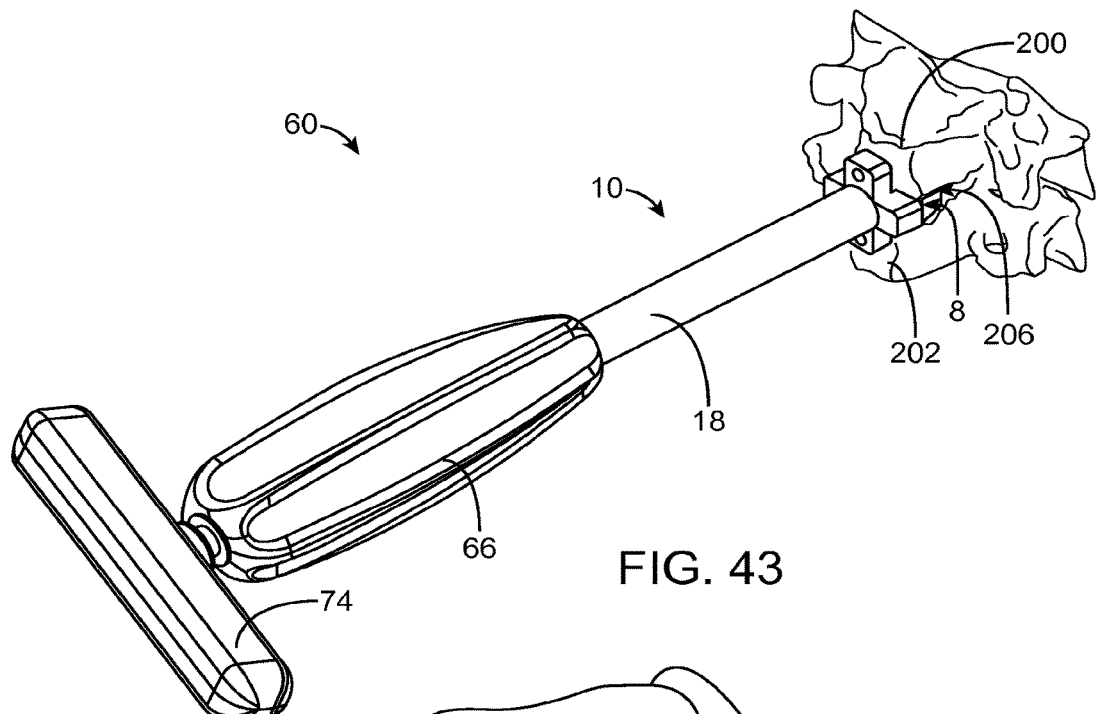
FIG. 43 is a proximal isometric view of the system adjacent a superior vertebra and an inferior vertebra.
Figure 44:
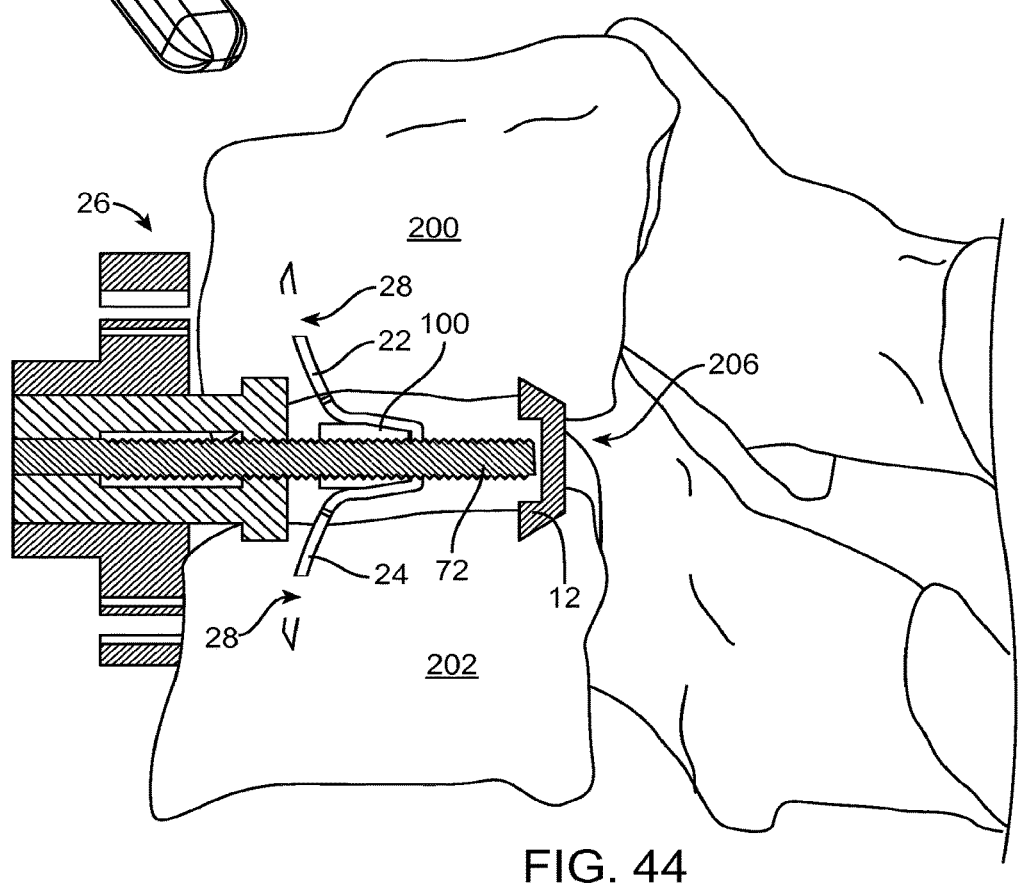
FIG. 44 is a vertical cross section through the two vertebrae with the fixation plate in the deployed state.
Figure 45:
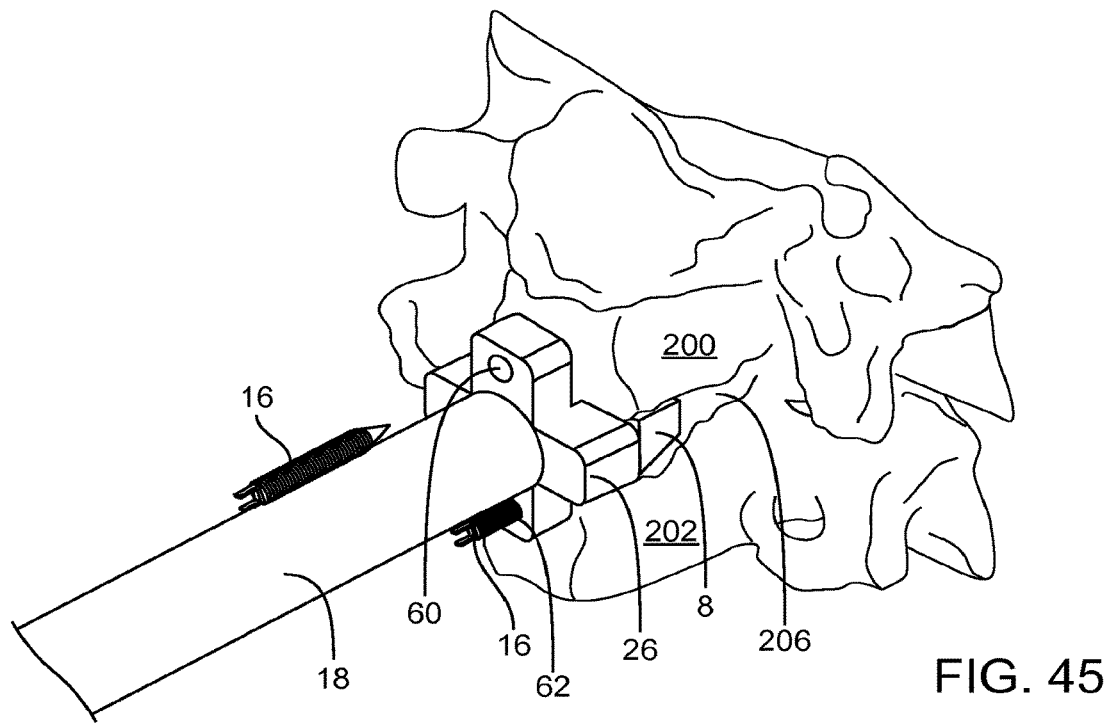
FIG. 45 is a proximal isometric view of the bone screws being implanted.

With the system 6 assembled as depicted in FIGS. 1 and 7, the implant 8 is inserted via the implanter distal end 26 into the disc space 206 defined between superior and inferior vertebra 200, 202 via an anterior approach, as indicated in FIG. 43. The handle 74 is then rotated relative to the handle 66 of the implanter 18 to cause the drive nut 100 to proximally displace along the threaded distal termination 72 to bring the plate 14 from the non-deployed state (see FIG. 29) to the deployed state (see FIG. 31), thereby driving the plate blades 22, 24 deep into their respective vertebra 200, 202, as shown in FIG. 44. The blade openings 28 are now aligned with the axes AA and 88, which are coaxial with the distal end guides 60, 62 and the handle guides 70, as illustrated in FIGS. 1, 6, 8, 9, 10, 12, and 14 discussed above. With the alignment of the guides 60, 62, 70 and the blade holes 28 generally coaxial with the axes AA and 88, the bone screws 16 can be delivered "blind" to be received in the blade holes 28 embedded deep in the vertebra 200, 202 as indicated by FIG. 45 and discussed above with respect to FIGS. 1, 2, 10, and 14. The result of the delivery of the bone screws 16 into the holes 28 of the blades 22, 24 embedded in the respective vertebra 200, 202 can be seen in FIG. 46.

Figure 46:
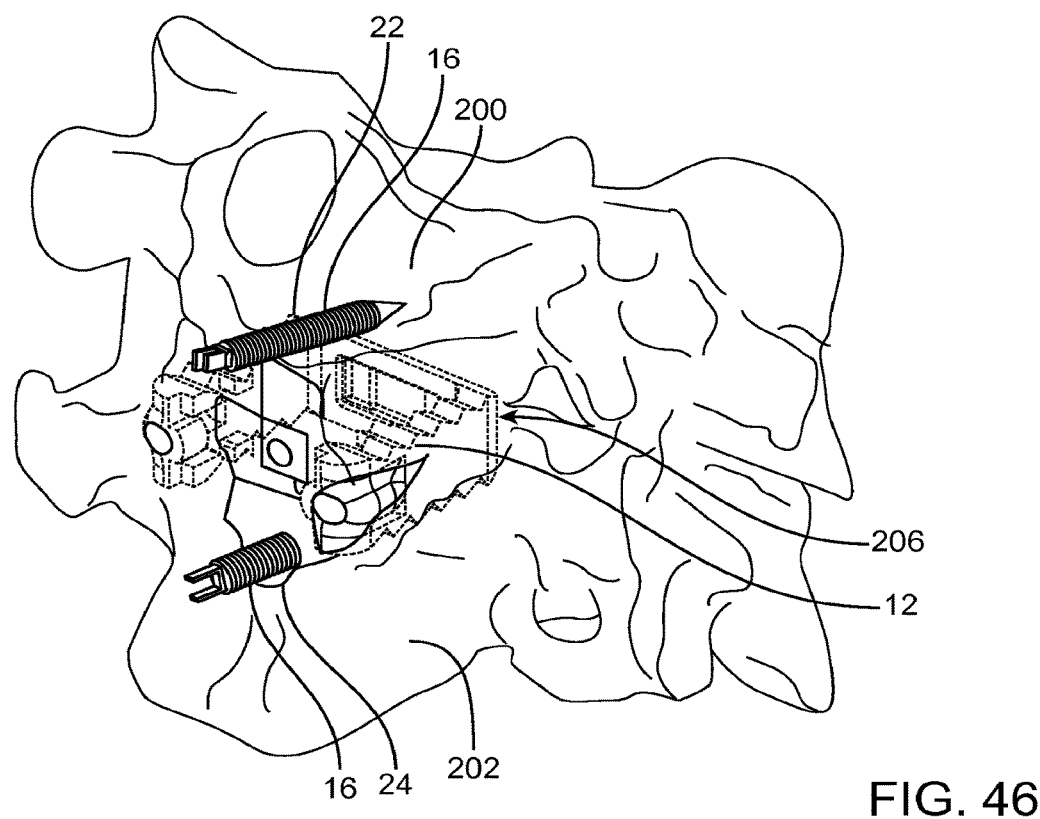
FIG. 46 is a proximal isometric view of the finished implantation of the implant with the vertebrae shown in phantom.

With the implant 8 implanted as depicted in FIG. 46, the implanter 18 and ramp 80 can be decoupled from the implanted implant 8 and withdrawn from the surgical site. Demineralized bone matrix or other paste-like bone graft material can then be injected into the interior volume 124 of the cage 12 via proximal opening 130 in the cage.

In one embodiment, the spinal fusion system 6 disclosed herein facilitates the safe and efficient delivery of a spinal implant 8 into a disc space of a patient via an implantation tool set 6 that allows for the "blind" delivery of a bone screw 16 through a vertebral body and into an opening 28 in the blade 22, 24 of a fixation plate 14 located within the confines of a cage 12, said blade 22, 24 projecting a substantial distance from the cage 12 into the vertebral body. Further, the spinal implant 8 is such that the fixation plate 14 is first deployed after which the bone screws 16 are caused to extend through both the vertebral body and the blade 22, 24 extending into said vertebral body, resulting in a plate-to-bone screw engagement. While the system 6 describes using bone screws 16 delivered through a vertebral body and into an opening 28 in the blade 22, 24 of a fixation plate 14, in certain embodiments, the system may function without delivering the bone screws 16 through the opening 28 in the blade 22, 24 of the fixation plate 14. Both types of systems are contemplated and within the scope of the present disclosure.

Referring now to FIGS. 47A-47E, any embodiment of the spinal fusion system 6 and methods described above may optionally also include a trial device 300 (or "sizer" or "sizing device"). (trialTrial device 300 may also be provided separately and not as part of a system). Trial device 300 may be used to assess a space between two vertebrae, for example. In some embodiments, trial device 300 may also include one or more blades 306 or other cutting devices, which may be used to cut cortical bone and thus prepare one or more bone surfaces for insertion of an interbody fusion cage or other implant. In the embodiment illustrated, best seen in FIGS. 47A-47, trial device 300 includes a body 302 and multiple, circular blades 306, which extend through an opening 304 in body 302. Blades 306 are coupled with an actuator 308, which may be rotated to cause blades 306 to rotate. Body 302 includes two channels 310a, 310b, into which prongs of an insertion device 312 may be inserted for delivery of trial device 300 to a position between two vertebrae. Any of the components of trial device 300 may be made of any suitable materials, such as but not limited to any suitable metals, polymers and/or any of the materials described above.

Figure 47A:
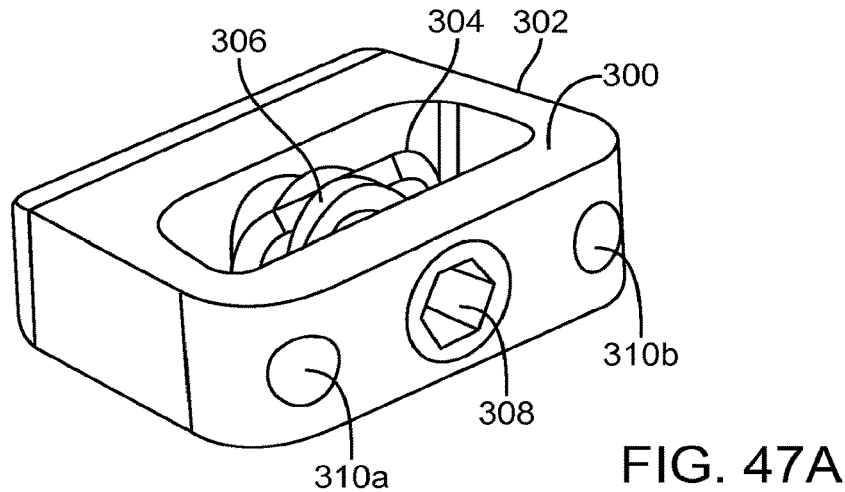
FIGS. 47A-47C are perspective, top and perspective view, respectively, of a trial implant device with rotating cutting blades, according to one embodiment.
Figure 47B:
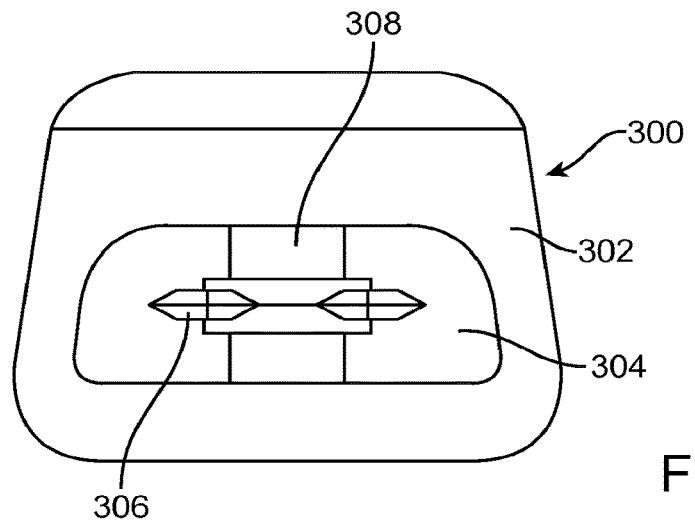
Figure 47C:
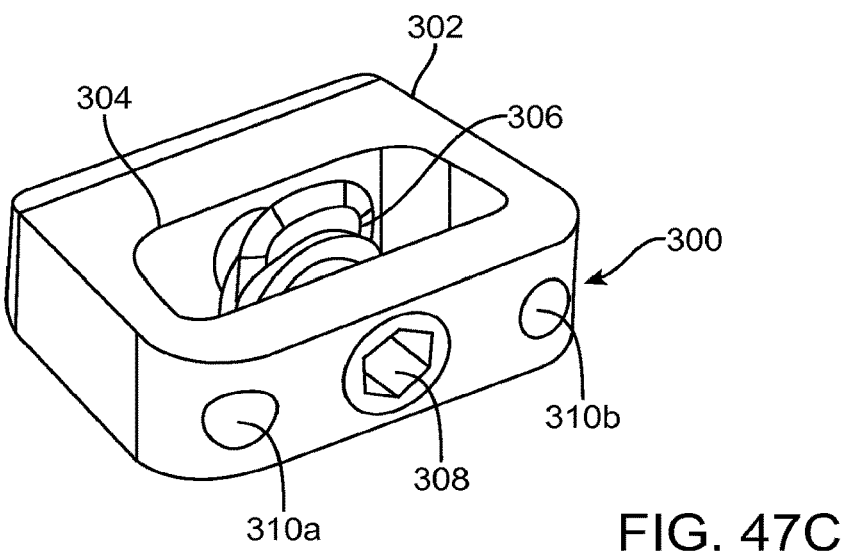
Figure 47D:
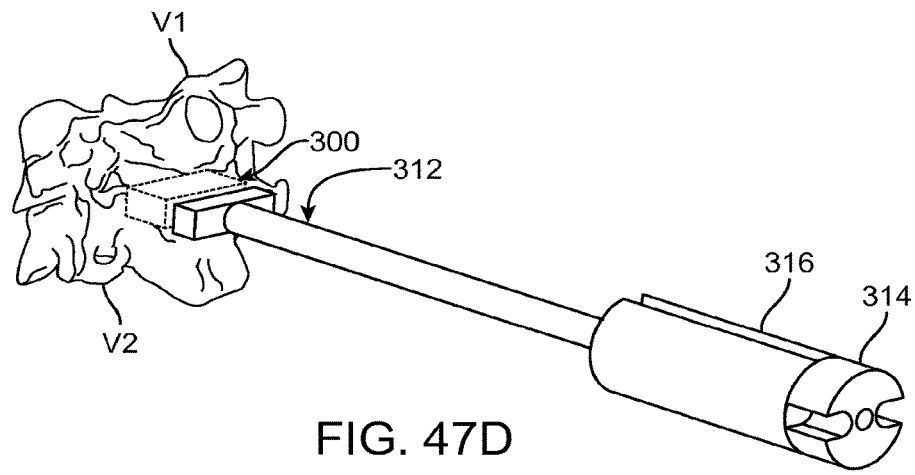
FIGS. 47D and 47E are perspective view of a system and method for using the trial implant device of FIGS. 47A-47C, according to one embodiment.
Figure 47E:
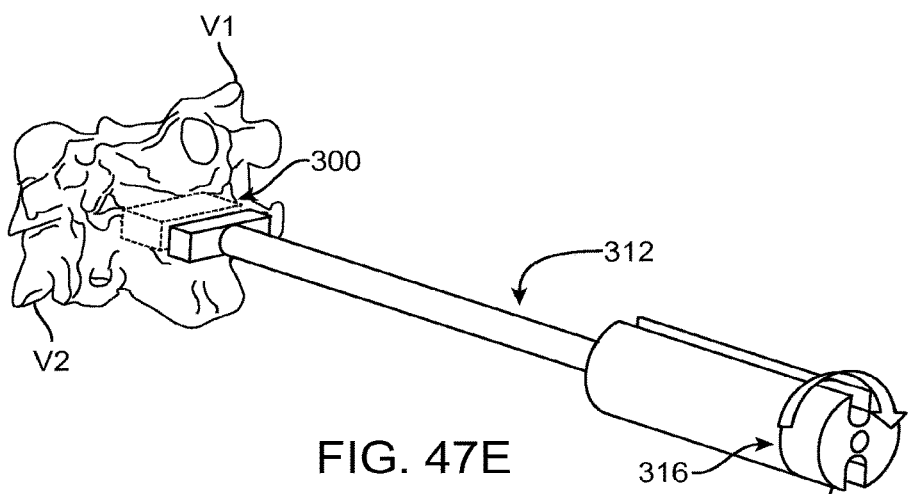

As illustrated in FIGS. 47D and 47E, a distal end of insertion device 312 may be coupled with trial device 300 and used to advance trial device 312 into a position between a superior vertebra V1V1 and an inferior vertebra V2V2. Insertion device 312 may include a handle 316 and an acutator knob 314, the latter of which may extend distally to a blade actuator, which fits within actuator 308 of trial device 300. Thus, after insertion of trial device 300 between the two vertebrae V1, V2V1, V2, as shown in FIG. 47D, knob 314 may be turned, as illustrated in FIG. 47E, to actuate blades 306 and thus cut cortical bone of the vertebrae V1, V2.V1, V2. Thus, trial deice 300 may serve two purposes—to test a size for a potential interbody fusion cage implant and to prepare one or more bone surfaces for receiving the implant. In alternative embodiments, trial device 300 may not include blades 306 and thus may simply be configured for sizing.

Figures 48A, 48B:
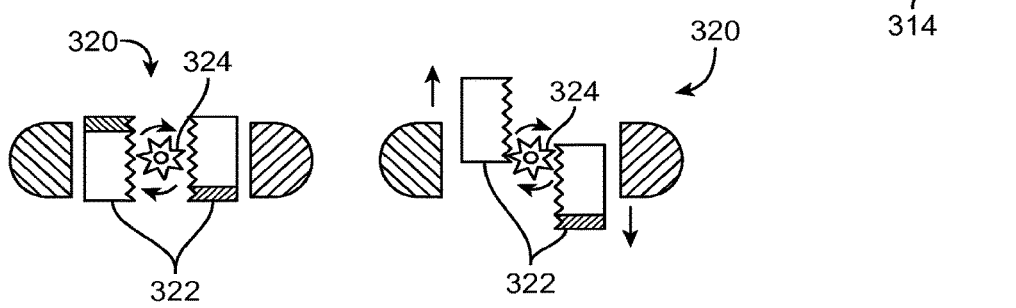
FIGS. 48A and 48B are cross-sectional, end-on views of a trial implant device with linear cutting blades, according to an alternative embodiment.

With reference now to FIGS. 48A and 48B, in an alternative embodiment, a trial device 320 may include linear-travel blades 322, rather than the rotating blades 306 of the previously described embodiment. Linear-travel blades 322 may be driven by an actuator 324, which when activated causes blades 322 to move up and down. Actuator 324 may be a drive gear, which is rotated using insertion device 312 (or an alternative insertion device) and which translates rotational motion into linear motion of blades 322.

Figures 49A, 49B:
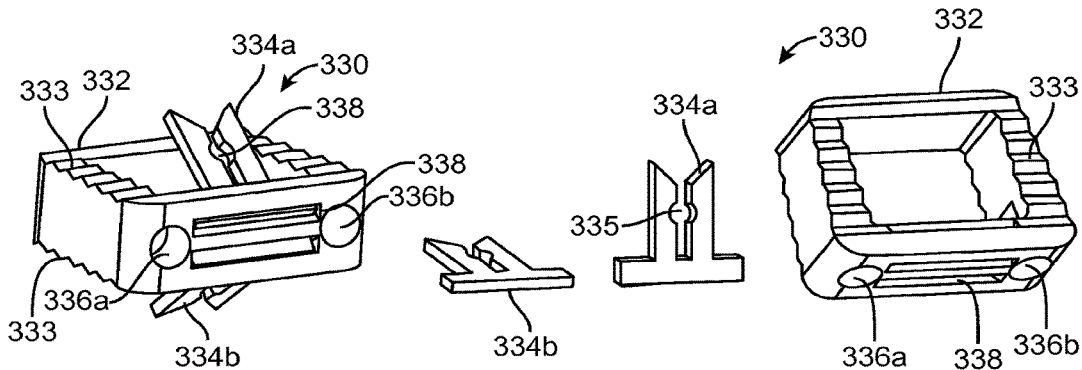
FIGS. 49A and 49B are perspective and exploded view, respectively, of an interbody fusion cage with anchoring plates, according to another embodiment.
Figure 49C:
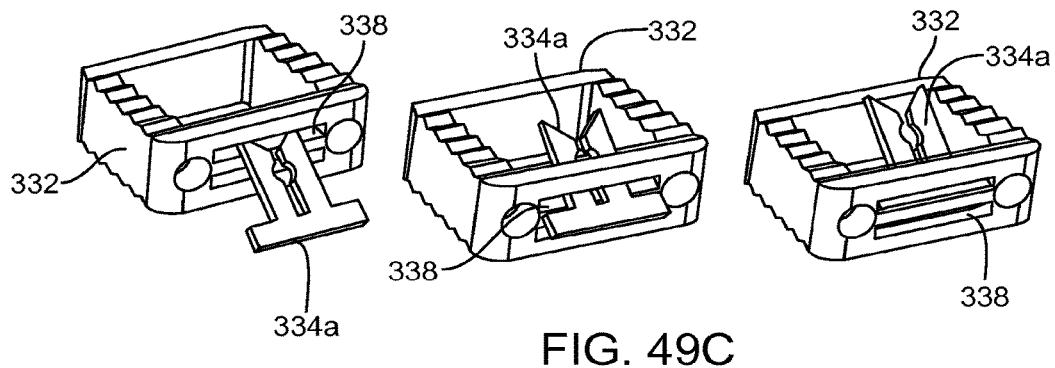
FIG. 49C illustrates a method for inserting an anchoring plate into an interbody cage, according to one embodiment.

Referring now to FIGS. 49A-49C, another embodiment of a cervical fusion cage implant 330 is illustrated. In this embodiment, implant 330 includes a body 332, which includes multiple contoured surfaces 333, two channels 336a, 336b for receiving prongs of an insertion device, and two angled slots 338. Implant 330 also includes two anchoring plates 334a, 334b (or "staples" or "anchoring blades"), which are configured to fit into angled slots 338, and which include sharp tips for anchoring into vertebral bone. In some embodiments, each anchor plate 334a, 334b may also include a feature 335 for engaging with a bone screw (not shown), after deployment. Anchoring plates 334a, 334b are incorporated into implant body 302 and are typically deployed by a drive mechanism, after body 302 is positioned between two vertebrae. Anchoring plates 334a, 334b generally serve to provide resistance to vertical separation of the vertebral sections. In various embodiments, anchor plates 334a, 334b may be straight or curved sharp-tripped blades with a thin profile. In the embodiment shown, anchor plates 334a, 334b are shaped as two thin prongs, for ease of insertion into bone.

FIG. 49A is a perspective view of implant 330 completely assembled, FIG. 49B is an exploded view of implant 330, and FIG. 49C illustrates insertion of one anchor plate 334a into one of the slots 338 of implant body 302. Upon insertion into one of the angled slots 338, each anchor plate 334a, 334b extends away from the insertion tool, toward the posterior side of the vertebrae. The insertion tool sues an impact-based driving mechanism, rather than a screw drive.

Figure 50A:
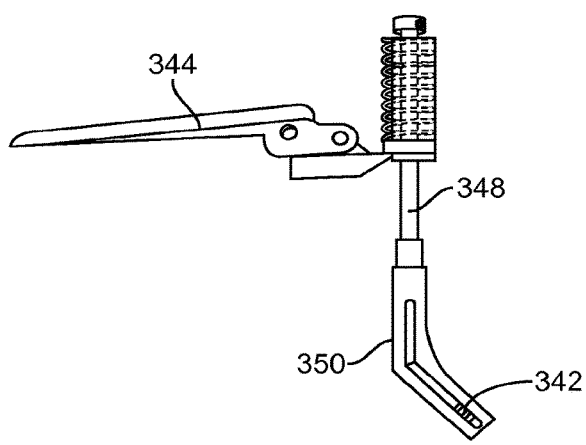
FIGS. 50A-50C are side view of a device for implanting the interbody fusion cage and anchoring plates of FIGS. 49A-49C.
Figure 50B:
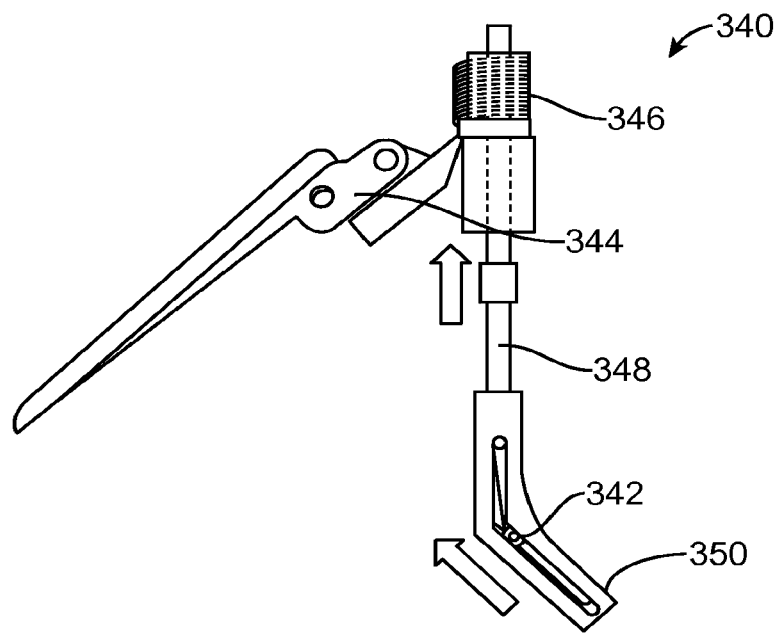
Figure 50C:
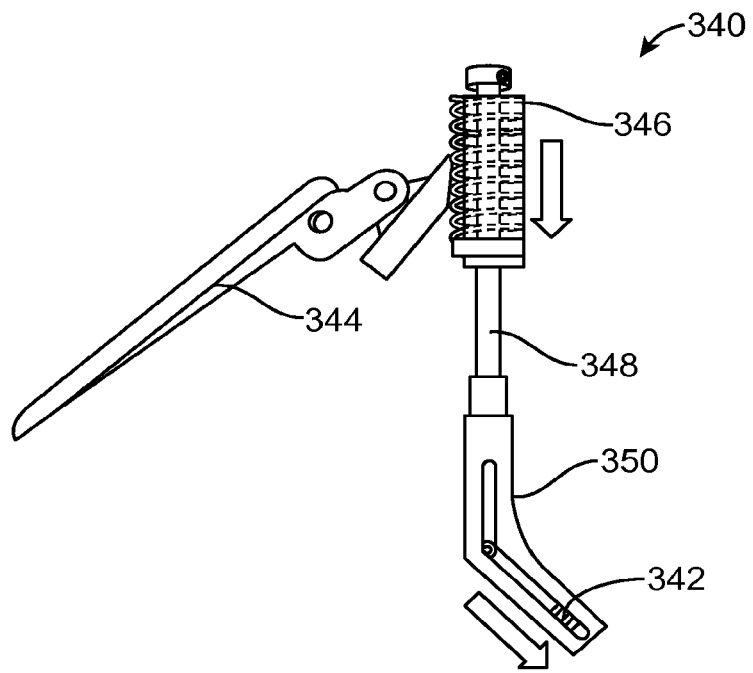

Referring now to FIGS. 50A-50C, a portion of an insertion device 340 for inserting implant 330 is illustrated in side view. Referring first of FIG. 50A, insertion device 340 may include a distal portion 350, which includes a staple driver 342 (or "anchor plate driver"), a shaft 348, a trigger 344 and a spring 346. Staple driver 342 may be used to provide impact force onto each anchor plate 334a, 334b, in sequence, to convert axial motion into the appropriate angle to drive each anchor plate 334a, 334b into the bone. FIG. 50A shows insertion device 340 in a pre-deployment positon.

FIG. 50B illustrates insertion device 340 with trigger 344 partially actuated, spring 346 compressed, and staple driver 342 retracted. FIG. 50 illustrates insertion device 340 with trigger 344 fully actuated, spring 346 release, and staple driver 342 fired. This mechanism of action may be used to advance anchor plates 334a, 334b into slots 338 on implant 330.

The foregoing merely illustrates various exemplary embodiments in detail. Various modifications and alterations to the described embodiments may be made within the spirit and scope of the present disclosure. Thus, the particular embodiments shown and described are for purposes of illustrations only and are not intended to limit the scope of the present disclosure. References to details of particular embodiments are not intended to limit the scope of the disclosure. The present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A method for fusing a superior vertebra to an inferior vertebra, the method comprising:
    coupling an implanter to a proximal region of an interbody fusion cage, the implanter comprising a ramp having opposed sloped surfaces distally projecting from a distal end of the implanter;
    inserting said interbody fusion cage by said implanter into a disc space defined by an inferior endplate of the superior vertebra and a superior endplate of the inferior vertebra;
    moving an inferior blade of a fixation plate located in an open volume of the interbody fusion cage into abutting engagement with one sloped surface of said ramp to cause said inferior blade to penetrate the superior endplate and extend at least half a vertical distance of a vertebral body of the inferior vertebra into the vertebral body of the interior vertebrae; and
    moving a superior blade of the fixation plate into abutting engagement with an opposing sloped surface of said ramp to cause said superior blade to penetrate the inferior endplate and extend at least half a vertical distance of a vertebral body of the superior vertebra into the vertebral body of the superior vertebra.

2. The method of claim 1, further including the steps of:
    causing a first bone screw to penetrate an anterior face of the vertebral body of the inferior vertebra and extend into the vertebral body of the inferior vertebra to be received in an opening defined in the inferior blade embedded in the vertebral body of the inferior vertebra; and
    causing a second bone screw to penetrate an anterior face of the vertebral body of the superior vertebra and extend into the vertebral body of the superior vertebra to be received in an opening defined in the superior blade embedded in the vertebral body of the superior vertebra,
        wherein causing the first and second bone screws to penetrate comprises using a blind delivery of the bone screws via an implanter coupled to a proximal region of the interbody fusion cage.

3. A method for fusing a superior vertebra to an inferior vertebra, the method comprising:
    introducing a disc preparation device into a disc space defined by an inferior endplate of the superior vertebra and a superior endplate of the inferior vertebra, said disc preparation device comprising a body including a superior surface, an inferior surface and an interior opening extending through the superior surface and the inferior surface, and at least one cutting device moveably disposed in the opening of the body, such that the at least one cutting device can be moved in such a way as to extend at least one of superiorly above the superior surface of the body or inferiorly below the inferior surface of the body;
    moving said at least one cutting device to extend at least one of superiorly above the superior surface of the body or inferiorly below the inferior surface of the body to cut into at least one of said inferior endplate or said superior endplate;
    removing said disc preparation device from said from said disc space;
    introducing an interbody fusion cage comprising a superior surface, an inferior surface, a distal region and a proximal region, and an opening extending through said superior surface and said inferior surface, said interbody fusion cage comprising a deployable fixation plate supported within said cage, said fixation plate comprising at least one blade disposed in the opening of said cage in such a way as to extend at least one of superiorly above the superior surface of said cage or inferiorly below the inferior surface of said cage; and
    moving said fixation plate toward said proximal region to deploy said at least one blade into the inferior or superior endplate cut into by the at least one cutting device of said disc preparation device.

4. The method of claim 3, wherein the proximal region of said interbody fusion cage comprises an open configuration, and wherein said deployable fixation plate is delivered into the opening of said interbody fusion cage through said open configuration.

5. A method for fusing a superior vertebra to an inferior vertebra, the method comprising:
    introducing a trial device into a disc space defined by an inferior endplate of the superior vertebra and a superior endplate of the inferior vertebra, said trial device comprising a body including a superior surface, an inferior surface and an interior opening extending through the superior surface and the inferior surface, and a rotatable blade disposed in the opening of the body, such that a first portion of said rotatable blade can be moved to extend superiorly above the superior surface of the body and a second portion of said rotatable blade can be moved to extend inferiorly below the inferior surface of the body, said body being of size and configuration similar to that of an interbody fusion cage implant;
    rotating said blade to extend said first portion superiorly above the superior surface of the body and said second portion inferiorly below the inferior surface of the body to cut into said superior endplate and said inferior vertebrae;
    removing said trial device from said from said disc space;
    selecting an interbody fusion cage to be of size and configuration similar to that of said trial device body, said interbody fusion cage comprising a superior surface, an inferior surface, a distal region, a proximal region, and an opening extending through said superior surface and said inferior surface, said interbody fusion cage comprising a deployable fixation plate supported within said cage, said fixation plate comprising a pair of movably deployable blades disposed in the opening of said cage, a first blade being movable to extend superiorly above the superior surface of said cage a second blade being movable to extend inferiorly below the inferior surface of said cage;

introducing said interbody fusion cage into said disc space; and deploying said fixation plate to move said first deployable blade toward said proximal region into said superior endplate cut into by the first portion of said trial device rotatable blade and said second deployable blade toward said proximal region into said inferior endplate cut into by the second portion of said trial device rotatable blade.

6. The method of claim 5, wherein the proximal region of said interbody fusion cage comprises an open configuration, and wherein an implanter is coupled to proximal region of the interbody fusion cage, and wherein the implanter comprises a ramp projecting distally from a distal end of the implanter, and wherein the method further includes the step of abutting the deployable blades against sloped surfaces of said ramp to cause said deployable blades to respectively penetrate said superior and inferior endplates.

7. The method of claim 6, further including the step of introducing said ramp into the opening of said cage through the open configuration of said proximal region of said cage.

8. The method of claim 6, wherein said rotatable blade comprises multiple rotatable blades, and wherein said first portion is on one rotatable blade and said second portion is on another rotatable blade.

* * * * *

UNITED STATES PATENT AND TRADEMARK OFFICE
CERTIFICATE OF CORRECTION

| | | |
|---|---|---|
| PATENT NO. | : 10,219,916 B2 | Page 1 of 1 |
| APPLICATION NO. | : 15/975267 | |
| DATED | : March 5, 2019 | |
| INVENTOR(S) | : Shigeru Tanaka et al. | |

It is certified that error appears in the above-identified patent and that said Letters Patent is hereby corrected as shown below:

In the Specification

At Column 3, Line 50, should read --…vertebra (step e).--.

At Column 6, Line 1, should read --…are perspective views of a…--.

At Column 6, Line 13, should read --…are side views of a device…--.

At Column 7, Line 5, should read --…implanted cage 12,…--.

At Column 10, Line 9, should read --…as indicated in FIG 15, the notches…--.

At Column 12, Line 52, should read --…slot, notch, groove or other type…--.

At Column 14, Line 57, should read --…in the fully deployed state,…--.

At Column 15, Line 55, should read --Trial device 300…--.

At Column 16, Line 10, should read --…vertebra V1 and an inferior…--.

At Column 16, Line 10, should read --…inferior vertebra V2.--.

At Column 16, Line 15, should read --…two vertebrae V1, V2, as shown…--.

At Column 16, Line 18, should read --…vertebrae V1, V2.--.

At Column 16, Line 60, should read --…insertion tool uses an…--.

Signed and Sealed this
Twenty-first Day of May, 2019

Andrei Iancu
*Director of the United States Patent and Trademark Office*